United States Patent [19]

Henkin et al.

[11] Patent Number: 4,991,576
[45] Date of Patent: Feb. 12, 1991

[54] ANESTHESIA REBREATHING SYSTEM

[76] Inventors: Melvyn L. Henkin, 5011 Donna Ave., Tarzana, Calif. 91356; Jordan M. Laby, 3038 Bayshore, Ventura, Calif. 93001

[21] Appl. No.: 255,372

[22] Filed: Oct. 11, 1988

[51] Int. Cl.$^5$ .................... A61M 16/00; A62B 9/02
[52] U.S. Cl. .................... 128/203.28; 128/205.13; 128/205.15; 128/205.17; 128/205.24; 128/202.27; 128/911; 128/912; 128/909
[58] Field of Search ............. 128/202.22, 202.27, 128/205.13, 205.14, 205.15, 909, 910, 911, 205.17, 205.24, 203.28

[56] References Cited

U.S. PATENT DOCUMENTS

| Re. 25,871 | 10/1965 | Andreasen | 128/205.15 |
|---|---|---|---|
| 3,046,979 | 7/1962 | Andreasen | 128/205.16 |
| 3,467,092 | 9/1969 | Bird et al. | 128/205.15 |
| 3,537,450 | 11/1970 | Fox | 128/205.16 |
| 3,721,238 | 3/1973 | Wise et al. | 128/909 |
| 3,794,026 | 2/1974 | Jacobs | 128/202.22 |
| 3,814,091 | 6/1974 | Henkin | 128/202.22 |
| 3,815,596 | 6/1974 | Keener et al. | 128/909 |
| 3,831,595 | 8/1974 | Valenta et al. | 128/202.22 |
| 3,867,934 | 2/1975 | Ollivier | 128/202.22 |
| 3,901,230 | 8/1975 | Henkin | 128/909 |
| 3,938,551 | 2/1976 | Henkin | 128/909 |
| 4,020,834 | 5/1977 | Bird | 128/205.14 |
| 4,051,847 | 10/1977 | Henkin | 128/202.22 |
| 4,067,328 | 1/1978 | Manley | 128/205.14 |
| 4,067,329 | 1/1978 | Winicki | 128/202.22 |
| 4,111,197 | 9/1978 | Warncke et al. | 128/202.27 |
| 4,323,064 | 4/1982 | Hoenig et al. | 128/202.22 |
| 4,333,451 | 6/1982 | Paluch | 128/911 |
| 4,603,833 | 8/1986 | Christianson | 128/202.27 |
| 4,637,384 | 1/1987 | Schroeder | 128/911 |
| 4,825,802 | 5/1989 | Le Bec | 128/202.22 |
| 4,838,258 | 6/1989 | Dryden et al. | 128/205.23 |

*Primary Examiner*—Clifford D. Crowder
*Assistant Examiner*—Kimberly L. Asher
*Attorney, Agent, or Firm*—Freilich Hornbaker Rosen

[57] ABSTRACT

An anesthesia rebreathing system including a single use structural portion and a reusable structural portion configured so as to be readily latched together to automatically couple respective fresh gas interface ports and patient overflow ports. The single use portion includes a patient bag which is mounted in a closed rigid container in the reusable portion. Gas pressure in the container is controlled by an anesthetist squeezing an outside bag or by a mechanical ventilator, as determined by the setting of a user operable control knob subassembly, which also functions to establish gas pressure and volume in both the patient circuit and the control circuit.

102 Claims, 30 Drawing Sheets

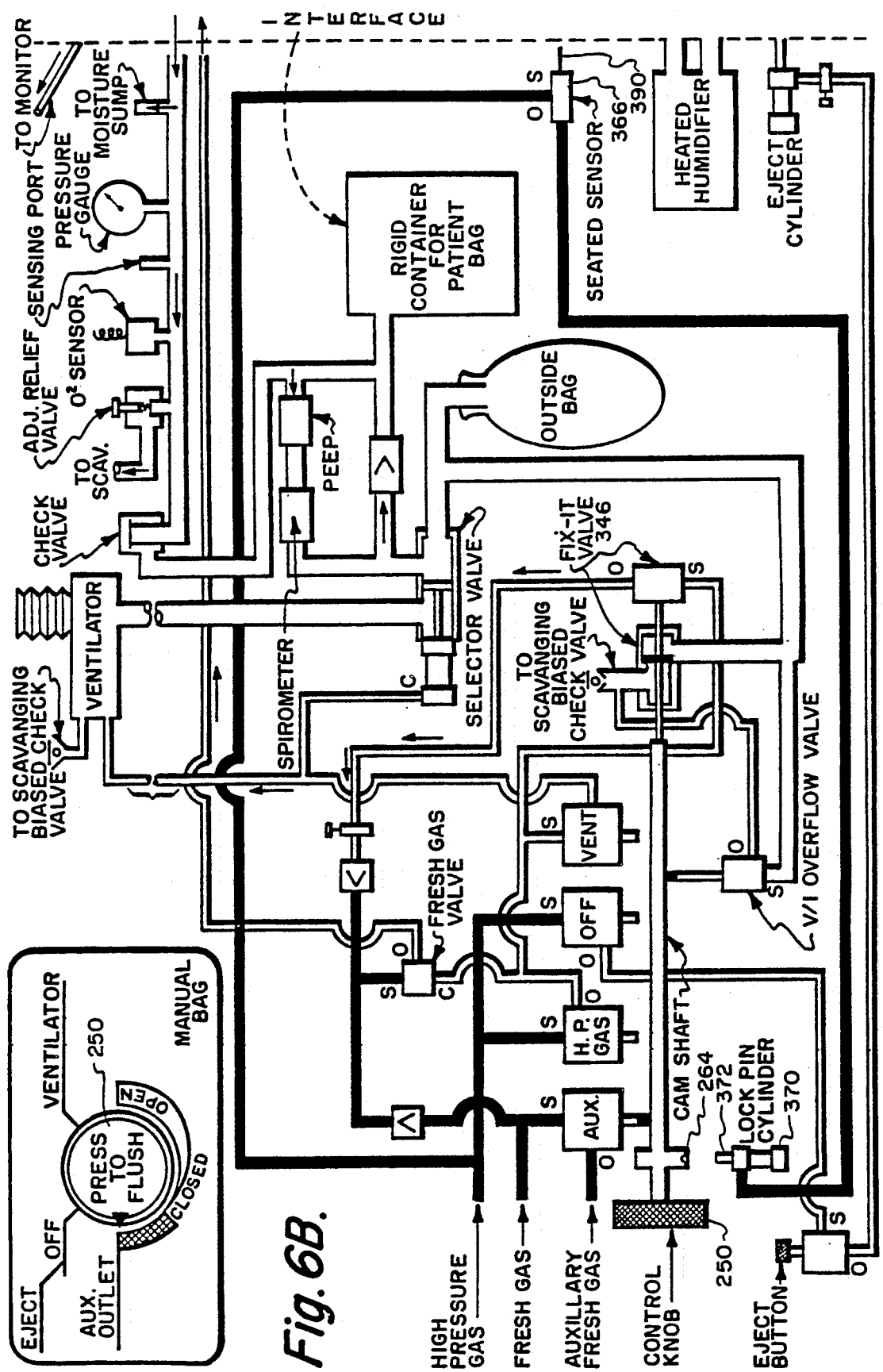

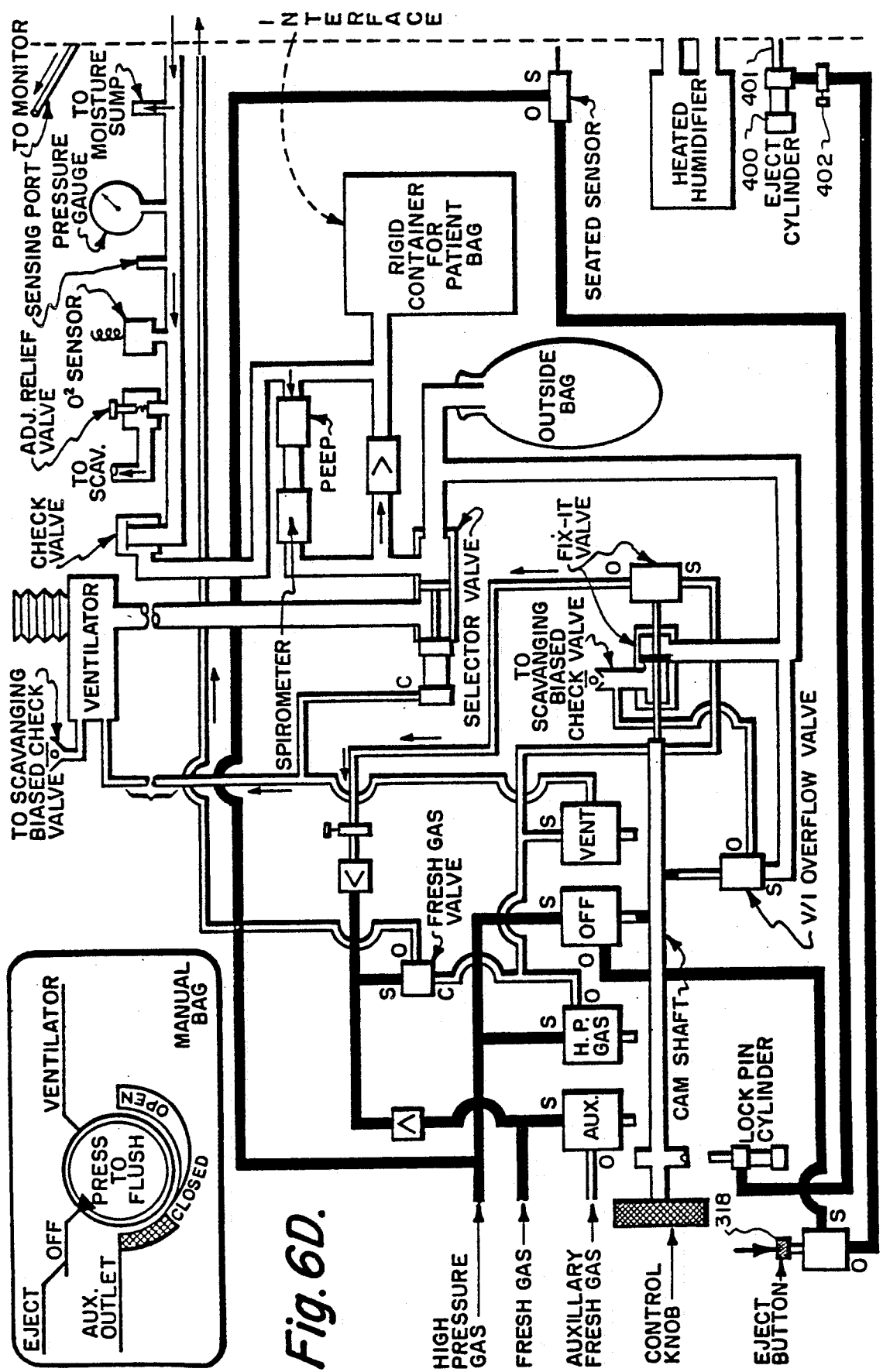

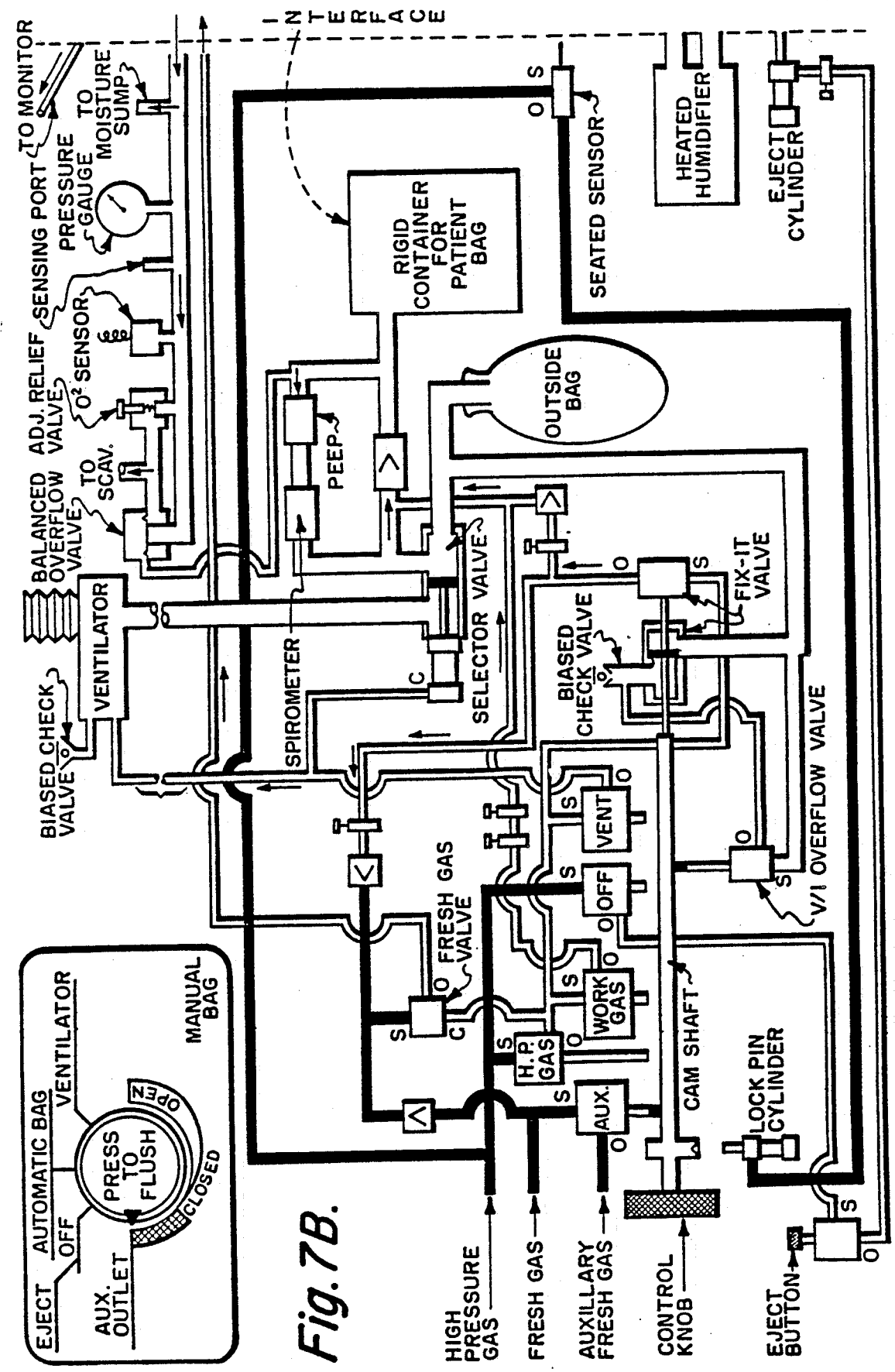

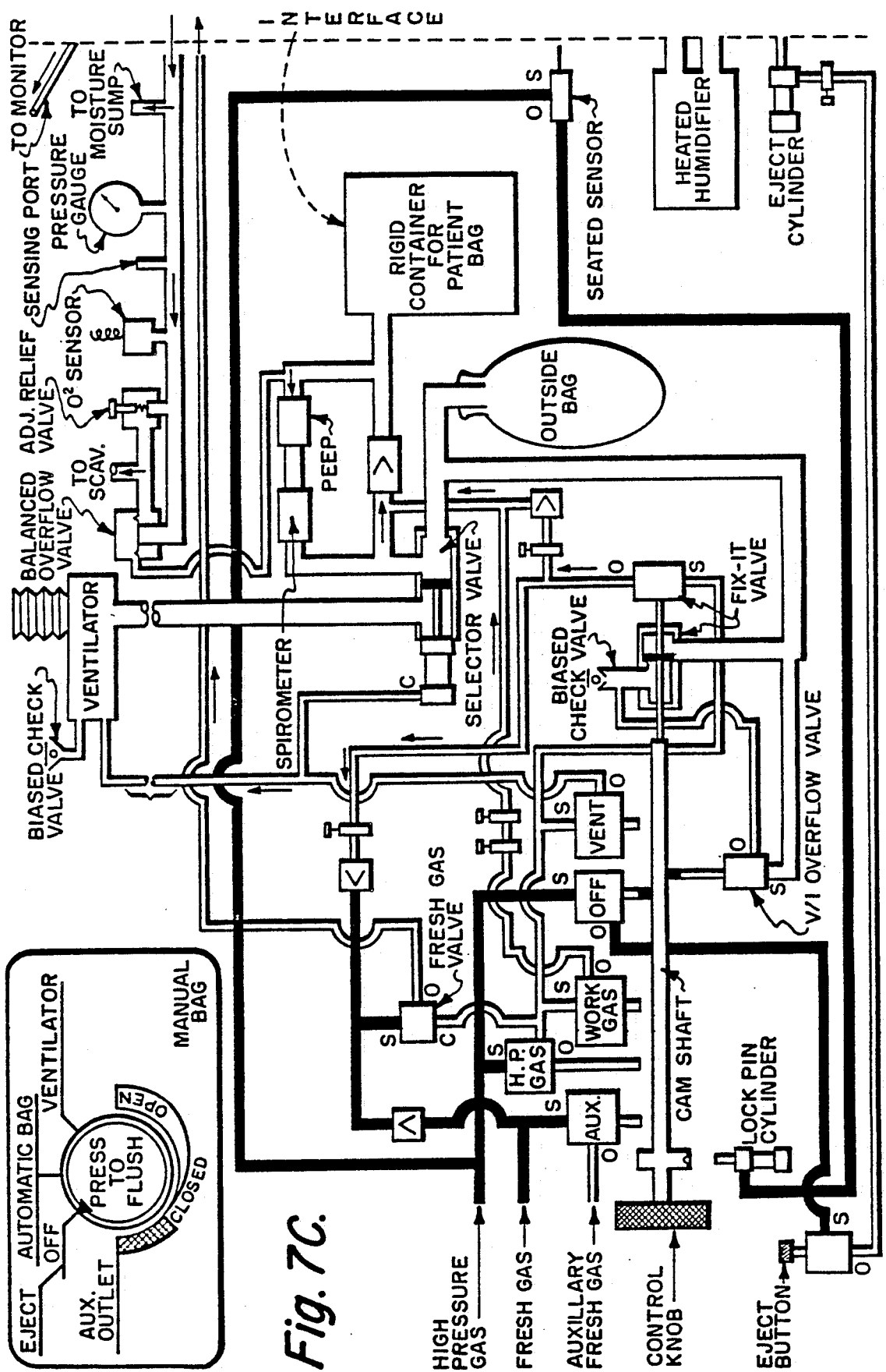

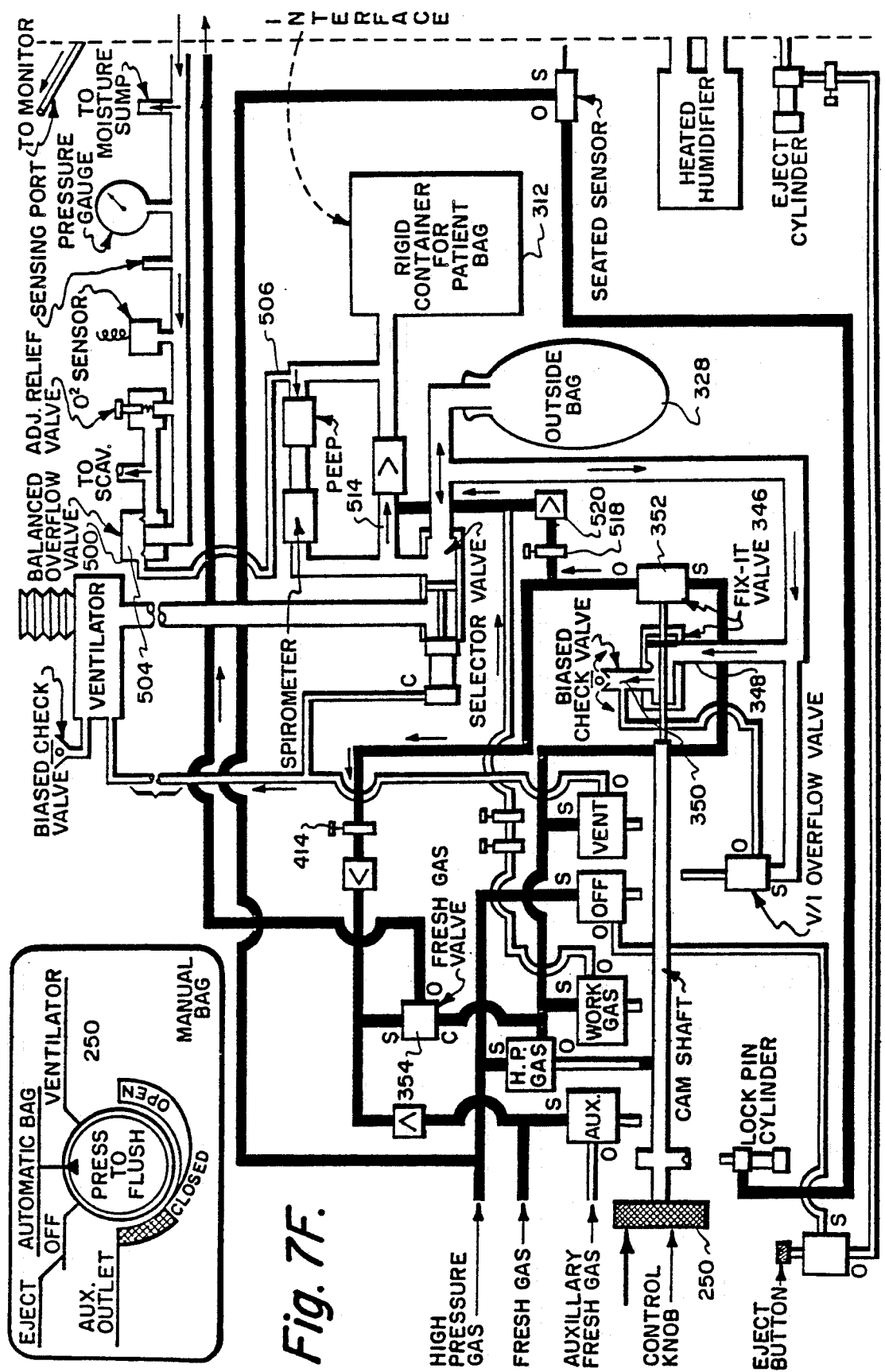

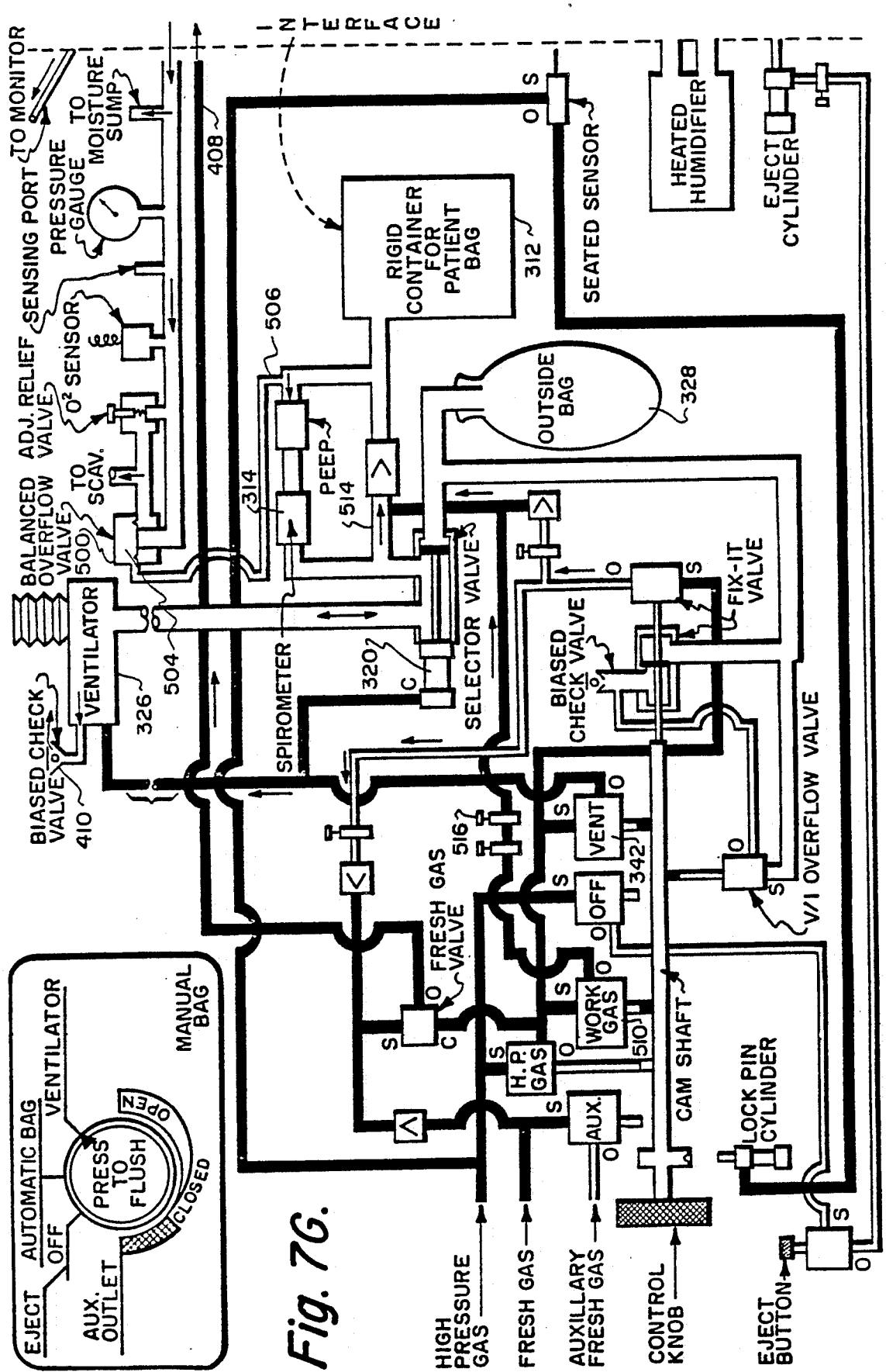

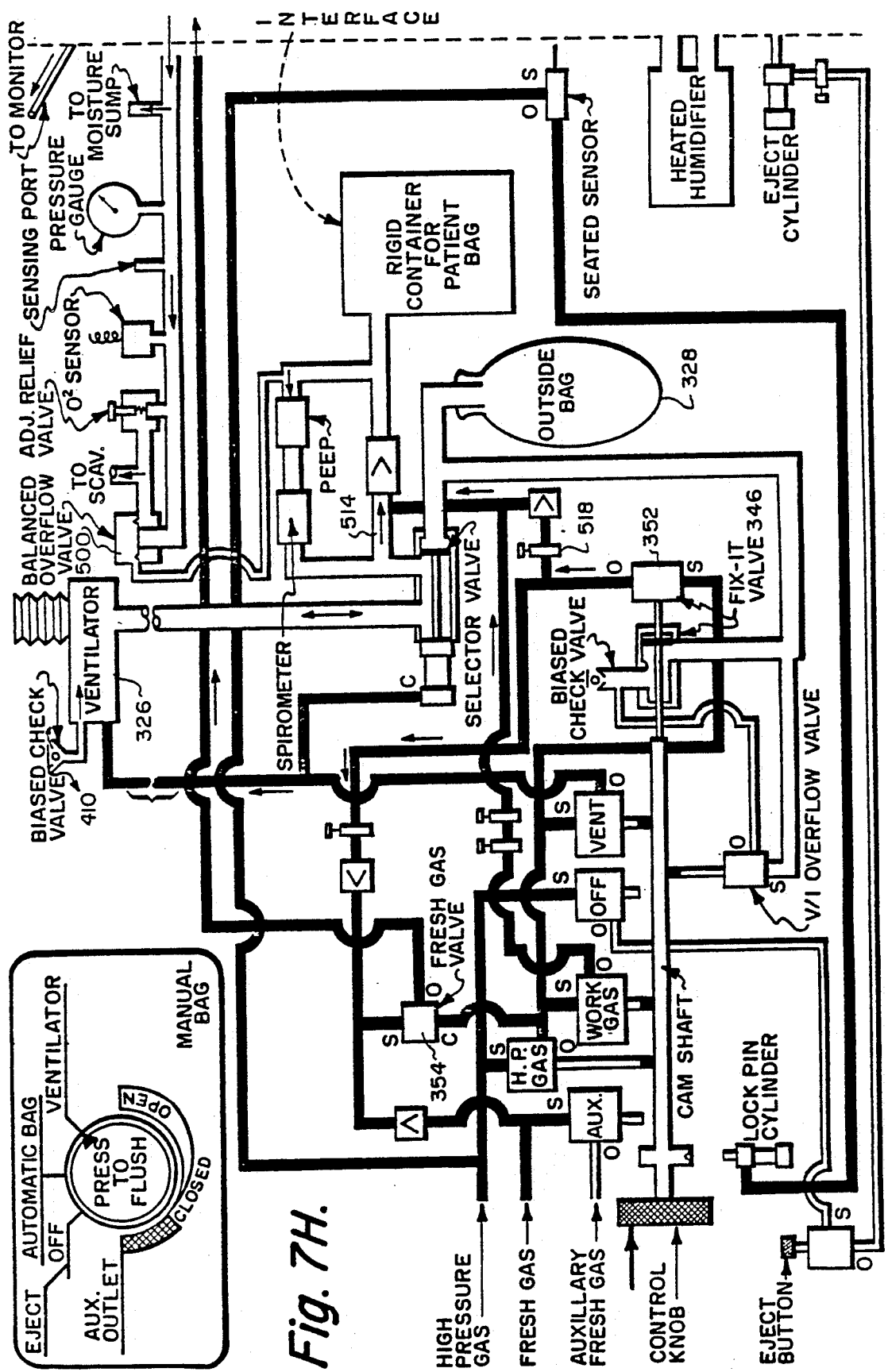

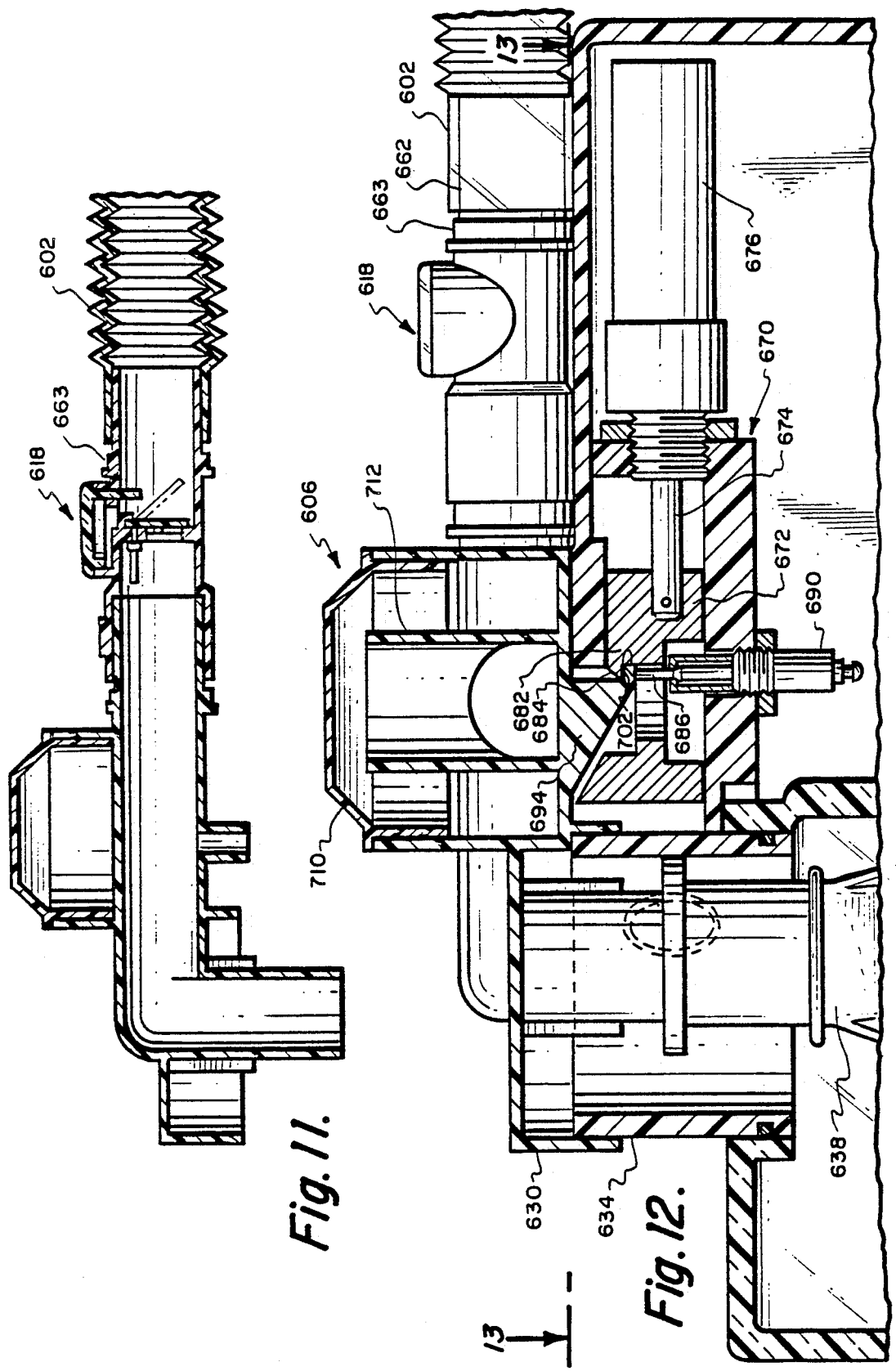

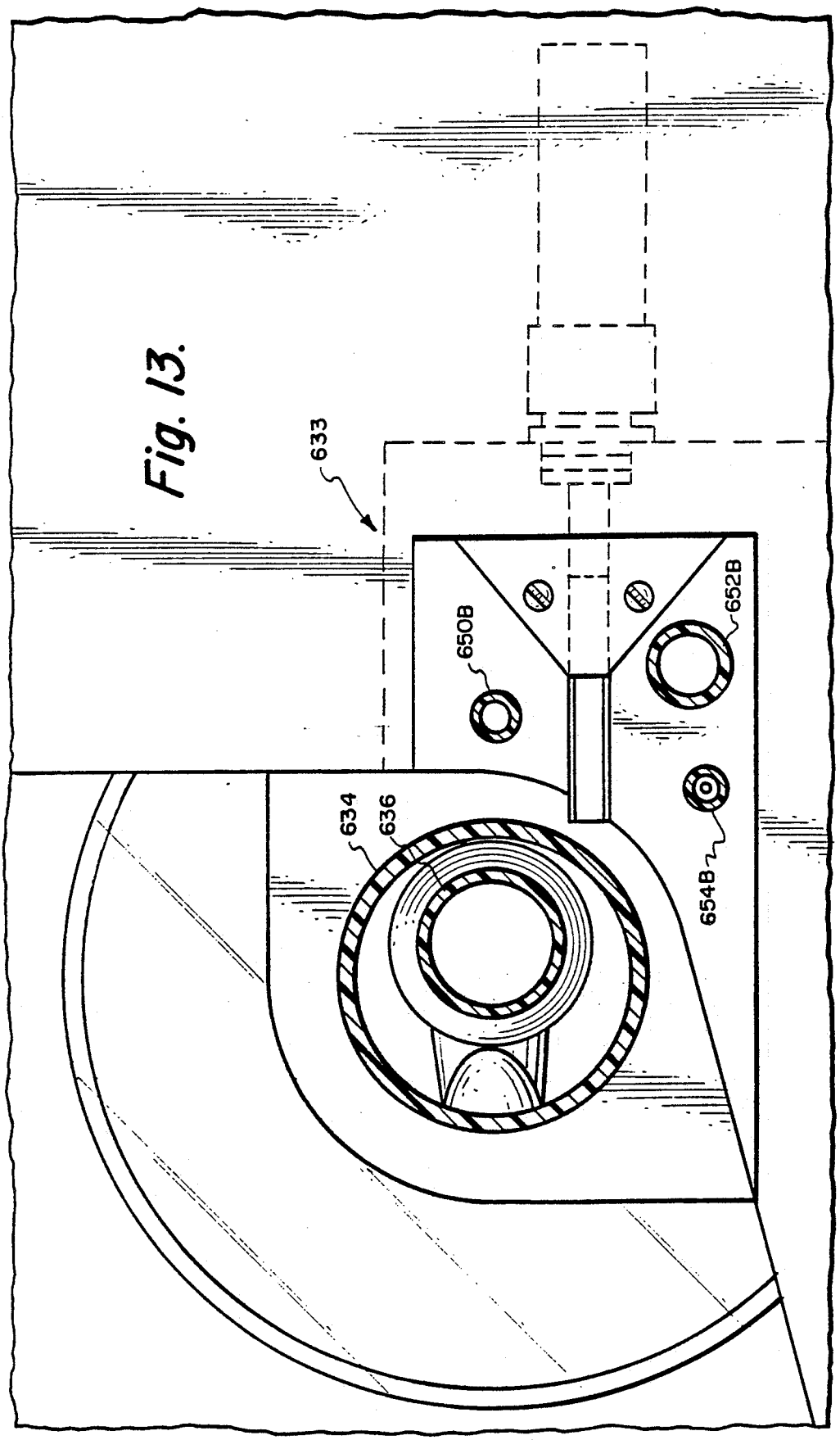

ANESTHESIA REBREATHING SYSTEM

BACKGROUND OF THE INVENTION

This invention relates generally to a system for administering general anesthetics in the gaseous state and more particularly to an anesthesia rebreathing system, comprised of a permanent (or reusable) structural portion and a disposable (or single use) structural portion.

U.S. Pat. Nos. 3,814,091 and 3,901,230 disclose an anesthesia rebreathing system comprised of a reusable structural portion and a single use structural portion cooperatively configured to minimize the possibility of crosscontamination between patients. The system is characterized by a geometry which preferentially vents expired alveolar gas, rich in $CO_2$, while preserving initially expired dead space gas to thus minimize the need for $CO_2$ absorption.

In one embodiment disclosed in U.S. Pat. No. 3,814,091, the single use portion comprises a patient circuit generally referred to as a circle including both inspiratory and expiratory patient breathing tubes. In a second disclosed embodiment, the patient circuit comprises a single breathing tube alternately used for inspiration and expiration. Each circuit embodiment also incorporates an overflow tube whose entrance is located very close to the patient. The overflow tube exits at a reusable patient overflow (commonly referred to as "pop-off") valve which is located close to an anesthesia machine where it can be conveniently controlled by an attending anesthetist. By locating the overflow tube entrance close to the patient, it functions to preferentially vent alveolar gas through the overflow valve and save dead space and unbreathed gas within the tubing and reservoir of the patient circuit. The patient reservoir is disclosed as comprising one chamber of a dual chamber bag. The overflow valve is disclosed as being operable in two different modes, i.e. (1) as a manually controlled variable orifice for spontaneous ventilation and (2) as an automatically controlled valve responding to a positive control pressure for manually assisted or mechanically controlled ventilation.

U.S. Pat. No. 3,901,230 discloses an enhanced system characterized by the inclusion of an improved subsystem for controlling the gas volume and pressure in the patient circuit. The subsystem (which has since become known as a "ventilator/isolator" circuit) includes a rigid container (forming part of the system's reusable portion) within which a single chamber patient breathing bag (forming part of the single use portion) is accommodated. The pressure within the rigid container is controlled (1) during manually assisted or controlled ventilation, by an attending anesthetist squeezing an outside bag and (2) during mechanically controlled ventilation by a conventional mechanical ventilator. The pressure variations in the rigid container are applied to the patient circuit via the flexible walls of the patient breathing bag. Crosscontamination is eliminated in such a system because the patient expired gas cannot come into contact with reusable portion components exposed to inspired gas.

More specifically, the enhanced system of U.S. Pat. No. 3,901,230 can be functionally viewed as including a patient circuit and a ventilator/isolator circuit for controlling gas volume and pressure in the patient circuit. The system can be structurally viewed as including a single use portion and a reusable portion. The system is configured so that the single use portion forms most of the patient circuit with the reusable portion forming the ventilator/isolator circuit and part of the patient circuit, e.g. the adjustable patient overflow valve.

The inventions disclosed in said U.S. Pat. Nos. 3,814,091 and 3,901,230 have been embodied in an anesthesia system marketed commercially since about 1976 as the ANTROL system by Diamed, a division of Illinois Tool Works, Inc. The ANTROL system with ventilator/isolator includes the following independently operable user controls:

1. Patient pop-off valve, variably adjustable between open and closed positions and having a ventilator position at which the pop-off valve is controlled by the pressure in the rigid container;
2. Ventilator/isolator selector valve, movable between first and second positions for respectively coupling either the outside bag or mechanical ventilator to the rigid container;
3. Ventilator/isolator fill valve for selectively filling the ventilator/isolator circuit; e.g. the ventilator bellows or the outside bag; and
4. Ventilator/isolator dump valve for selectively relieving pressure from the ventilator/isolator circuit; e.g. the ventilator bellows or the outside bag.

The foregoing user controls are used by the attending anesthetist in conjunction with anesthesia machine controls (e.g. flush valve) to maintain proper gas volume and pressure in the patient and ventilator/isolator circuits.

SUMMARY OF THE INVENTION

The present invention is directed to an improved anesthesia rebreathing system which retains many of the advantageous characteristics of the systems disclosed in U.S. Pat. Nos. 3,814,091 and 3,901,230 and which additionally incorporates several new features to significantly enhance the ease of use and safe operation of the system. More specifically, embodiments of the present invention similarly include a patient circuit implemented primarily as a single use structure and a ventilator/isolator circuit, implemented primarily as a reusable structure, for controlling gas volume and pressure in the patient circuit.

In accordance with a significant aspect of the invention, instead of using the aforementioned multiple independently operable user controls, embodiments of the present invention employ an integrated user control means comprising a control knob whose position determines the system operating mode. Thus, in a first preferred embodiment, the user control knob can be rotated to any one of the following mutually exclusive positions:

1. auxiliary outlet
2. off
3. mechanical ventilator mode
4. manual bag mode

Positions 3. and 4. comprise the positions for respectively ventilating the patient either with a mechanical ventilator (i.e. position 3.) or with manual assistance or spontaneously (i.e. position 4.). In a second preferred embodiment, the four aforementioned positions are supplemented by an automatic bag mode position (i.e. position 5.) at which the system is properly controlled without manual adjustment.

The first and second embodiments of the invention additionally differ in that in the first embodiment, the gas flow from the patient circuit overflow tube is used as working gas for the ventilator/isolator circuit. In the second embodiment, ventilator/isolator circuit working gas is derived from a high pressure gas supply (preferably dry medical grade oxygen).

In accordance with a further aspect of the invention, adjustable overflow valve means for controlling outflow from the patient circuit is located in the ventilator/isolator circuit (as contrasted with its being in the patient circuit in prior systems). In both disclosed embodiments, this overflow valve means can be selectively adjusted by the user by rotating the control knob, while in the manual bag position, to vary the flow rate out of the ventilator/isolator circuit.

The single use patient circuit includes a connector body appropriately configured to be mated to tubular fittings on the reusable portion. In accordance with the preferred embodiments of the invention, latching means are provided for latching the connector body in place when it is properly seated on the reusable portion.

In accordance with a significant feature of the preferred embodiments, sensor means are provided for indicating when the connector body is properly seated. The sensor means are coupled to the aforementioned control knob for preventing it from being moved to any of the ventilating positions (i.e. 3, 4, 5) unless the connecting body is properly seated. This feature assures that the patient circuit is properly connected before an anesthesia procedure can begin.

In accordance with a further feature of the preferred embodiments, the latching means is configured to allow the connector body to be readily manually seated onto the reusable portion but preventing it from being inadvertently unseated while the system is in a ventilating mode. More specifically, in order to unseat the latched connector body, the preferred embodiments include unlatching means operably coupled to the control means and actuatable only when the control knob is not in a ventilating mode position, e.g. the off position, to both unlatch and eject the connector body.

In accordance with a further aspect, in lieu of providing independently operable user fill and dump valve controls for the ventilator/isolator circuit and a flush valve control for the patient circuit, systems in accordance with the invention are configured so that actuation of a common control member automatically adjusts the gas volume and pressure to a predetermined set of initial conditions in each circuit regardless of whether the circuit was previously too empty or too full. In accordance with a related feature of the preferred embodiments, the user control means is configured so that the common control member is actuated by pressing the rotatable control knob. In accordance with an additional feature of the preferred embodiments, means are provided for automatically initializing (i.e. establishing said initial conditions) said circuits whenever said control knob is used to change into or out of any ventilating position.

In accordance with a still further feature of the invention, means are incorporated in the ventilator/isolator circuit for enabling the user to set a pressure against which the patient breathes out, i.e. positive end expiratory pressure.

Systems in accordance with the invention are compatible with various types of patient circuits including those having separate inspiratory and expiratory tubes and those having common inspiratory and expiratory tubes. Inasmuch as such systems require a separate overflow tube, they are respectively implemented as 3-tube or 2-tube structures. In a preferred 3-tube implementation, the overflow tube is threaded through the expiratory tube. In a preferred 2-tube implementation, the overflow tube is threaded through the single breathing tube.

In accordance with a preferred single use patient circuit structure, an end expiratory monitoring tube is threaded through the expiratory tube from the mask elbow to the connector body for automatically interfacing with the reusable structure.

BRIEF DESCRIPTION OF THE FIGURES

FIGS. 6A-6H comprise a series of schematic flow diagrams showing the first system embodiment of FIG. 2 in greater detail, and wherein each of the FIGS. 6A-6H depicts a different system condition and the active flow paths for both the fresh gas and the high pressure gas for each such condition;

FIGS. 7A-7J comprise a series of schematic flow diagrams showing the first system embodiment of FIG. 3 in greater detail, and wherein each of the FIGS. 7A-7J depicts a different system condition and the active flow paths for both the fresh gas and the high pressure gas for each such condition;

FIG. 11 is a sectional view taken substantially along the plane 11—11 of FIG. 10 showing the proximal end of the inspiratory tube;

FIG. 12 is a sectional view taken substantially along the plane 10—10 showing the connector body of the single use patient circuit latched to the structural mounting interface of the reusable system portion;

FIG. 13 is a sectional view taken substantially along the plan 13—13 of FIG. 12;

DESCRIPTION OF THE PREFERRED EMBODIMENT

Figure 1:
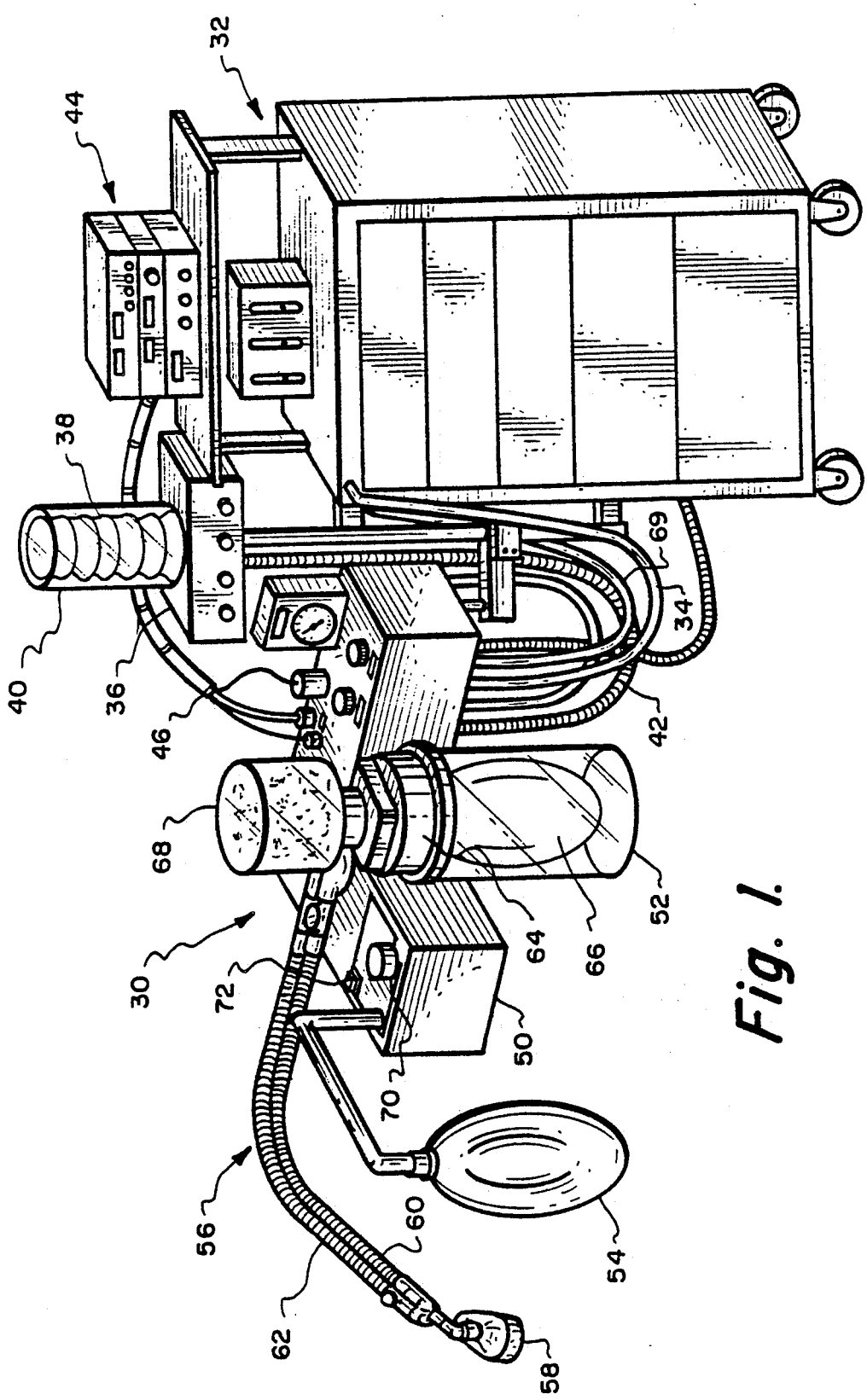
FIG. 1 is an isometric view depicting the structure of an anesthesia rebreathing system in accordance with the present invention.

Attention is initially directed to FIG. 1 which generally depicts the structure of an anesthesia rebreathing system 30 in accordance with the present invention. The system 30 is compatible with a conventional anesthesia machine 32 capable of supplying fresh anesthesia gas via tube 34 to the system 30. Also shown in FIG. 1 is a conventional mechanical ventilator 36 which may include a bellows 38 housed in a transparent cylinder 40. The ventilator 36 can be mounted externally and coupled, as shown, via tube 42 to the system 30 or alternately can be internal to the system. Conventional analyzer equipment 44, e.g. gas analyzer, oxygen sensor, are provided and coupled to the system 30 by various tubes generally shown as 46.

The system 30 as generally depicted in FIG. 1 is comprised of a reusable structural portion generally including a control arm 50, a transparent rigid container 52, and an outside bag 54 conveniently mounted so that it can be squeezed by an attending anesthetist. The system 30 also includes a disposable or single use structural portion 56 generally shown as including a patient airway communication means, e.g. mask 58, inspiratory and expiratory tubes 60, 62, a connector body 64, and a patient breathing bag 66.

As will be discussed in detail hereinafter, in the use of the system 30, the patient bag 66 is inserted into and sealed within the rigid container 52 as a consequence of seating the connector body 64 onto the structural mounting interface of the reusable portion. A single use $CO_2$ absorber canister 68 can be mounted on the connector body 64, if desired, for anesthesia procedures using lower fresh gas inflow.

The control arm 50 houses the tubing and valving of a ventilator/isolator circuit, comprising a subsystem for controlling the gas volume and pressure within the patient circuit. The patient circuit is defined by the aforementioned single use patient circuit portion 56 and also by certain reusable portions of the patient circuit, to be discussed. In addition to the fresh gas supplied to the control arm 50 from the anesthesia machine 32, high pressure gas, preferably dry medical grade oxygen, is also supplied to the control arm via tube 69.

The control arm 50 in accordance with the present invention is characterized by the use of a single selector control knob 70 which as will be discussed hereinafter, is available to the anesthetist to control various functions of the system, such as to establish predetermined gas volume and pressure (hereinafter referred to as "initial" conditions) in both the ventilator/isolator and patient circuits and also to select various operating modes such as the manual bag mode and the ventilator mode. As will be seen, in the manual bag mode, a patient can breathe spontaneously or his breathing can be manually assisted or controlled by the anesthetist squeezing the outside bag 54. In the ventilator mode, the patient's breathing is assisted or controlled by the action of the mechanical ventilator 36. As will be discussed hereinafter in connection with FIG. 7A–7J, the second system embodiment can additionally be operated in an automatic bag mode in which the system automatically maintains the initial conditions without user intervention.

The control arm 50 is further illustrated as including an eject button 72 which is used to unlatch and eject the connector body 64 after it has been latched on to the structural mounting interface.

In common with the system disclosed in aforementioned U.S. Pat. No. 3,901,230 the primary functions of the system 30 are:

1. to supply anesthesia gas to the patient via the mask 58 in sufficient volume and at a safe pressure;
2. to serve as a reservoir between the varying flow of fresh anesthesia gas into and out of the patient and the normally constant rate of anesthesia gas supply;
3. to eliminate excess gas from the system;
4. to reduce the inspired concentration of $CO_2$ to acceptable levels; and
5. to enable the patient's rebreathing to be assisted or controlled by manual or mechanical means.

Figure 2:
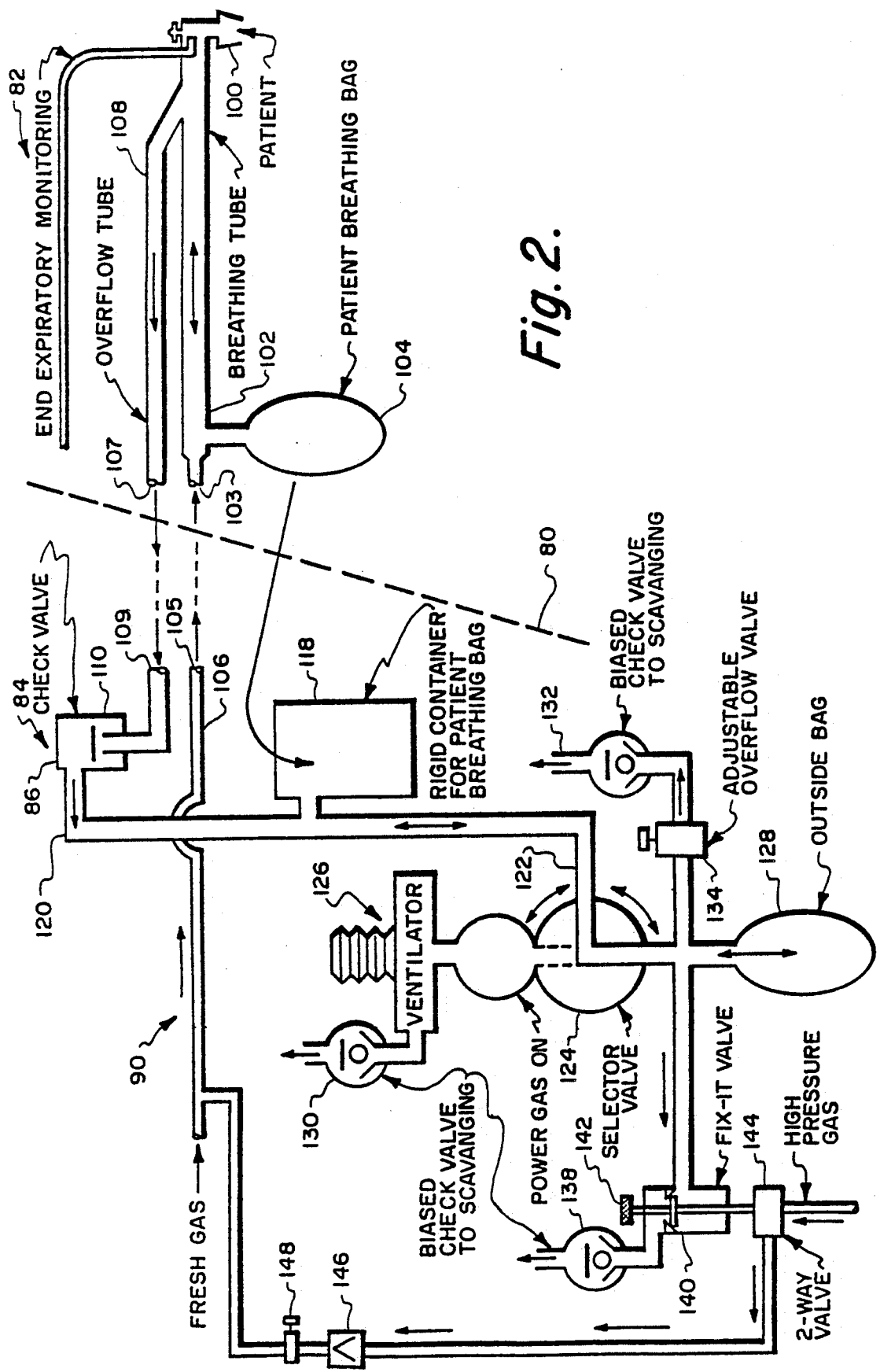
FIG. 2 is a generalized block diagram of a first system embodiment in accordance with the present invention which is represented in greater detail in FIGS. 6A-6H.

Attention is now directed to FIG. 2 which depicts a first embodiment of a system 30 in accordance with the present invention. Note that the dashed line 80 is intended to represent the interface between the system's single use portion 82 and reusable portion 84. The single use portion 82 includes the major portion of the patient circuit, depicted in FIG. 2 as a 2-tube circuit. The reusable portion 84 preferably includes certain structural members, e.g. check valve 86, which may be functionally viewed as part of the patient circuit. However, the reusable portion 84 primarily comprises the ventilator/isolator subsystem for controlling the gas volume and pressure in the patient circuit. Safe and reliable control of the patient circuit involves several aspects. Firstly, it is extremely important for the patient circuit to be controlled so as to avoid overpressurization which could damage a patient's lungs. Secondly, it is also essential that a sufficient supply of gas of the proper composition always be available for patient inspiration. Thirdly, it is important that the control subsystem for the patient circuit, i.e. the ventilator/isolator, provide the anesthetist with a means for rapidly initializing or readjusting the gas volume and pressure in the patient circuit if either of the two aforementioned conditions begins to develop. Fourthly, it is important that operation of the ventilator/isolator be easy and safe to use to avoid user error damaging the patient and lastly, it is important that the ventilator/isolator provide the mechanism whereby the patient circuit can be operated either in a spontaneous, a manually assisted or controlled, or a mechanical ventilator ventilation mode. The ventilator/isolator subsystem 90 of FIG. 2 has been designed to effectively handle all of these functions.

The single user portion depicted in FIG. 2 is comprised of a mask elbow fitting 100 adapted to be coupled to a patient mask or endotracheal tube. The fitting 100 communicates with a breathing tube 102 which is shown as including a single limb for both expiratory and inspiratory gas movement but which can comprise separate inspiratory and expiratory tubes. The distal end of the breathing tube 102 is connected to the elbow fitting 100. The proximal end of the breathing tube 102 defines a fresh gas interface port 103 which is connected to a fresh gas interface port on the reusable portion across the interface 80. A patient breathing bag 104 communicates with breathing tube 102 close to the interface port 103. The reusable portion fresh gas interface port 105 opens to a fresh gas supply line 106. The single use patient circuit additionally includes an overflow tube 108 having a tube entrance located close to the patient, i.e. fitting 100. The proximal end of the overflow tube 108 at interface port 107 is connected to a reusable interface port 109 across the interface 80. Interface port 109 opens to inlet port 110 of check valve 86 which controls the gas outflow from the patient circuit. As will be seen, the check valve 86 and the pressure which is applied to the patient bag 104 are controlled by the ventilator/isolator subsystem 90 as determined by the attending anesthetist.

The ventilator/isolator subsystem 90 includes a rigid container 118 in which the patient bag 104 is accommodated. Changes in pressure within the container 118 are transferred to the patient circuit via the flexible walls of the patient bag. Increases or decreases in gas volume within the patient bag are reflected by gas movement out of or in to the rigid container 118.

Whereas the gas inlet to the check valve 86 comprises the proximal end of the overflow tube 108, the check valve gas outlet 120 is coupled to the ventilator/isolator subsystem 90 communicating with the opening to rigid container 118 and to a port 122 of a selector valve 124. The selector valve 124 is operable to connect either a mechanical ventilator 126 or an outside bag 128 to the port 122. The mechanical ventilator 126 has a biased check valve 130. The mouth of the outside bag 128 is coupled to a biased check valve 132 via adjustable overflow valve 134. The mouth of outside bag 128 also communicates with a biased check valve 138 via the "dump" portion 140 of a "fix-it" valve which can be operated by the user by pressing a control knob 142 to initialize gas volume and pressure conditions in both the ventilator/isolator and patient circuits. Pressing of the control knob 142 also operates the "fill" portion 144 of the fix-it valve which permits high pressure gas (preferably medical grade oxygen) to flow into the fresh gas line 106 via check valve 146 and needle valve 148.

In the operation of the system of FIG. 2, the selector valve 124 will be in the position shown for manually assisted or controlled ventilation or spontaneous ventilation. In spontaneous ventilation, fresh gas will continually be supplied via tube 106 to the patient bag 104 and breathing tube 102. Initially expired patient dead space gas will be returned to the reservoir, i.e. patient bag 104, and alveolar gas will flow through tube 108 past the check valve 86 to the ventilator/isolator circuit. Thus, the expired gas going past the check valve 86 will, in the embodiment of FIG. 2, function as working gas for the ventilator/isolator subsystem. For manually assisted or controlled ventilation, with the selector valve 124 in the position shown, the anesthetist will squeeze the outside bag thus closing the check valve 86 to increase the pressure within the rigid container 118 which will be reflected against the walls of the patient bag 104. Thus, the squeezing of the outside bag 128 has a directly corresponding effect on the patient bag 104. Thus, the setting of the adjustable overflow valve 134 and biased check valve 132 determine the pressure in both the ventilator/isolator circuit and the patient circuit. The outside bag 128 will provide the anesthetist with the same tactile feedback he would get if he were squeezing the patient bag 104 directly.

If an overpressure condition develops either in the patient or ventilator/isolator circuit or a gas insufficiency occurs in either circuit, the user can press the control knob 142 to flush the patient circuit, i.e. produce a rapid high flow rate from the high pressure gas source into the fresh gas line 106. For example, whereas the fresh gas flow is typically less than 10 liters per minute, the flush flow of the patient circuit is preferably 50-70 liters per minute. This action also flushes the ventilator/isolator circuit via check valve 86. Additionally, both the patient circuit (via check valve 86) and the ventilator/isolator circuit via the biased check valve 138 are vented via dump portion 140 of the fix-it valve. The fix-it valve is preferably configured so that the dump portion 140 opens earlier and closes later than fill portion 144. As a consequence, the initialized condition is established by the biased check valve 138.

In order to operate in the mechanical ventilator mode, the position of the selector valve 124 is changed to disconnect the outside bag 128, (as shown in dashed lines) and connect the ventilator 126, to the rigid container. The mechanical ventilator 126 will then control the pressure on the patient circuit as a consequence of gas movement past port 122 and in to and out of the rigid container 118. Overpressurization in the patient and ventilator/isolator circuits will be avoided by the action of the biased check valve 130 during the expiration phase of the ventilator cycle. An insufficiency of gas volume in the patient and ventilator/isolator circuits can be immediately rectified by the anesthetist pressing control knob 142 to open valve 144 to flush fresh gas line 106 with high pressure gas.

The system embodiment of FIG. 2 will be discussed in greater detail in connection with FIGS. 6A-6H which depict how the selector valve 124 and control knob 142 are integrated into a single user control for enhancing safe and reliable operation.

Figure 3:
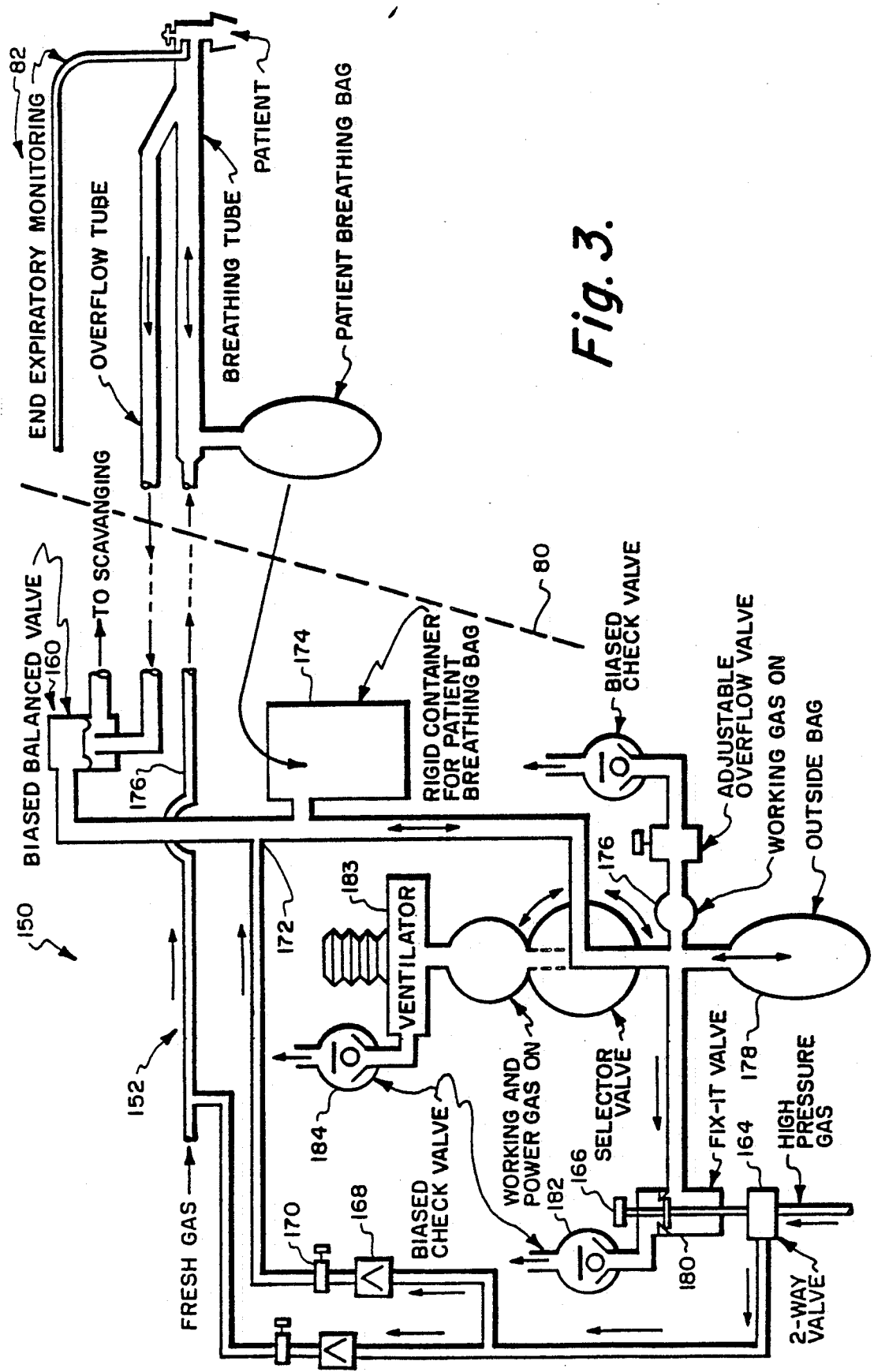
FIG. 3 is a generalized block diagram of a second system embodiment in accordance with the invention which is represented in greater detail in FIGS. 7A-7J.

Attention is now directed to FIG. 3 which illustrates a second system embodiment in accordance with the present invention. The single use portion 82 of FIG. 3 (which is identical to the corresponding portion of FIG. 2) communicates across interface 80 with a reusable portion 150. The reusable portion 150 differs from the reusable portion 84 of FIG. 2 primarily as a consequence of the ventilator/isolator circuit 152 using dry medical grade oxygen for working gas (i.e. to fill the rigid container and outside bag) whereas the ventilator/isolator circuit 90 of FIG. 2 used patient expired gas from the overflow tube 108. Use of patient expired gas as working gas (FIG. 2) does not present a cross contamination risk inasmuch as gas flow through the overflow tube 108 can only occur in one direction past the check valve 86 and there is no path in FIG. 2 for the ventilator/isolator working gas to enter the patient circuit. However, a disadvantage of using patient expired gas for ventilator/isolator circuit working gas is that such gas is generally of high humidity and may have impurities, such as blood or phlegm which could, over extended periods, affect the reliability of valving and flows in the ventilator/isolator circuit as well as the mechanical ventilator. Although this risk is minimal if the reusable portion is properly maintained, the system of FIG. 3 avoids this likelihood by using the high pressure gas supply to provide working gas.

Thus, it will be noted that the system of FIG. 3 differs from that of FIG. 2 in that instead of the check valve 86 coupled to the proximal end of overflow tube 108, a biased balanced overflow valve 160 is used. FIG. 3 further differs in that high pressure gas valve 164, operable by control knob 166, is coupled to an additional path comprised of check valve 168 and needle valve 170 to port 172 communicating with the upper chamber of the balanced overflow valve 160 and the entrance to the rigid container 174. Additionally, note that high pressure working gas is supplied to port 175 in the limb of the adjustable overflow valve and also to the mechanical ventilator to accommodate leaks.

Operation of the system of FIG. 3 is similar to that described for FIG. 2 except that it should be noted that when the control knob 166 is depressed, with the selector valve in the outside bag position, not only will high pressure gas be supplied to the fresh gas line 176 for flushing the patient circuit, but in addition high pressure gas will be supplied via port 172 to the ventilator/isolator circuit including rigid container 174 and outside bag 178. At this time, inasmuch as the pressing of the control knob 166 opened fix-it valve dump portion 180, the gas volume in the ventilator/isolator circuit will either increase (as a consequence of flow into port 172) or decrease (as a consequence of outflow through check valve 182) to thus establish the gas volume and pressure in the ventilator/isolator circuit at a level established by biased check valve 182. When the control knob 166 is depressed with the selector valve in the mechanical ventilator position, the high pressure gas, in addition to being supplied to fresh gas line 176, will be supplied to the ventilator 183 to fill its bellows. In this case, the ventilator check valve 184, rather than check valve 182, will establish the gas volume and pressure in the ventilator/isolator circuit. The ventilator/isolator circuit pressure typically set at 1-2 cm of water, the minimum necessary to keep the patient and outside bags full, will also establish the pressure in the patient circuit via the balanced overflow valve 160. It should be noted in the systems of FIGS. 2 and 3 that out flow from the patient overflow tube 108 does not occur during inspiration. That is, on inspiration, check valve 86 and balanced valve 160 are always closed. Therefore the system preferentially vents alveolar gas and preserves dead space and fresh gas to enhance efficiency.

Figure 4B:
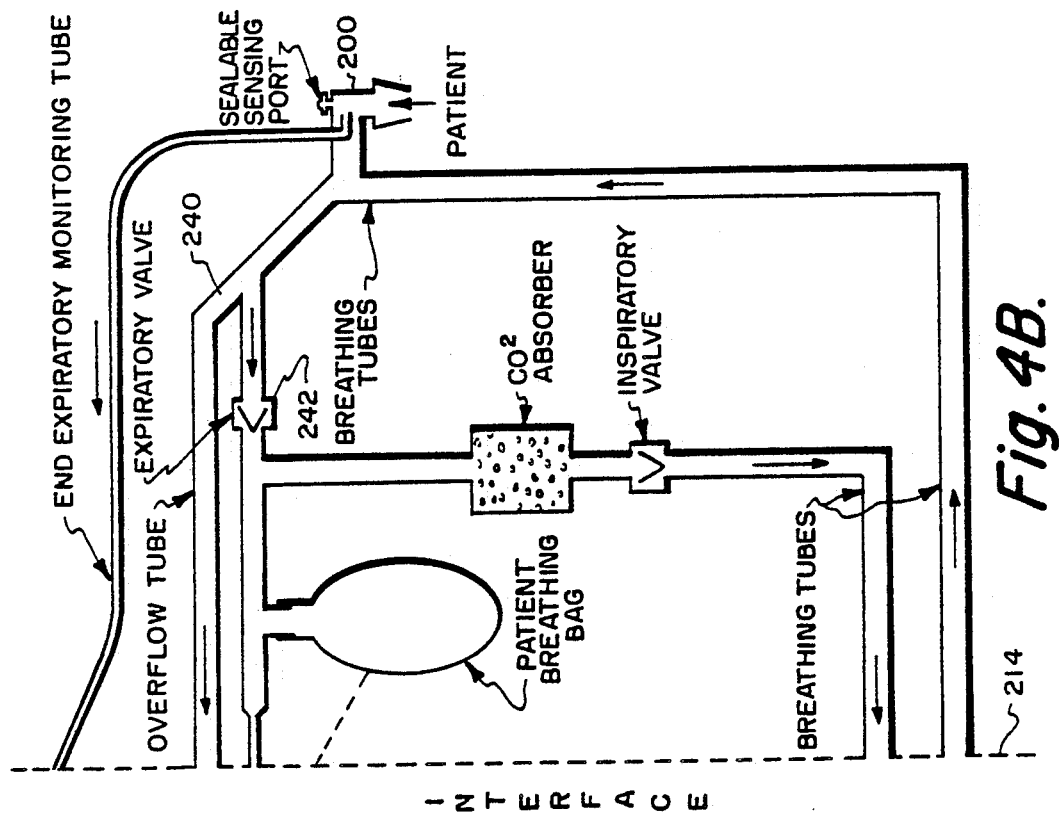
FIGS. 4A and 4B are schematic diagrams of alternative 3-tube patient circuits in accordance with the invention.
Figure 4A:
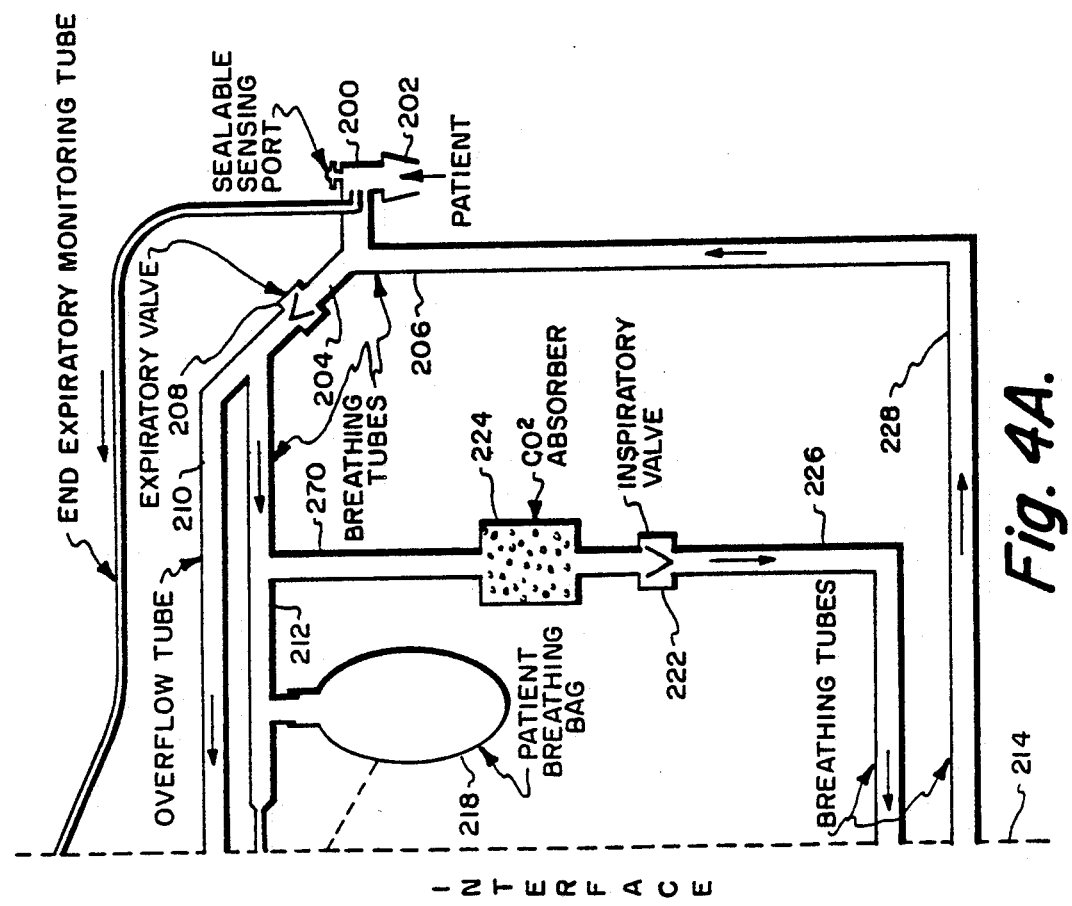

The block diagrams of FIGS. 2 and 3 illustrate identical single use structural portions 82 comprised of 2-tube patient circuits. As will be recalled, 2-tube patient circuits include a single breathing tube without inspiratory or expiratory check valves and a single overflow tube. Because of their simplicity, many anesthetists prefer this type of breathing circuit. However, 3-tube circuits in which separate inspiratory and expiratory breathing tubes or limbs can also be used in accordance with the invention. FIGS. 4A and 4B respectively illustrate different variations of such 3-tube circuits.

The patient circuits of FIGS. 4A and 4B includes a mask elbow fitting 200 having an exit nipple 202 intended to be connected to a patient mask or endotracheal tube. The nonpatient end of the fitting 200 is typically connected through a Y-piece to nipples 204 and 206. Nipple 204 is then coupled through an expiratory valve 208, thereafter branching into overflow tube 210 and expiratory tube 212. The overflow tube 210 extends to an interface line 214 shown in FIGS. 4A and 4B which is intended to mate with a corresponding interface line shown in each of FIGS. 6A-6H and 7A-7G. Similarly, the expiratory tube 212 extends to the interface line 214 for mating with the reusable structural portion shown to the left of interface line 214 in FIGS. 6A-6H and 7A-7J. Connected to the expiratory tube 212 is a patient breathing bag 218, identical to the breathing bag 104 discussed in connection with FIG. 2, and which is intended to be received in a rigid container in the reusable structural portion to the left of the interface line 214, as will be discussed hereinafter. Additionally, the expiratory path 212 branches at 220 to an inspiratory valve 222. An optional $CO_2$ absorber 224 can be incorporated between the expiratory path and the inspiratory valve 222. Tube 226 extends to the interface 214 and as will be discussed in connection with FIGS. 6A-6H and 7A-7J, is coupled to a heated humidifier to the left of the interface line 214 within the reusable structural portion. Inspiratory tube 228 emerges from the interface line 214 and then is coupled back to the Y-piece nipple at 206. Thus very simply, on inspiration, gas from the patient reservoir 218 flows past the inspiratory valve 222 and through the optional heated humidifier (FIGS. 6A-6H and 7A-7J), through tube 228 and to the elbow fitting 200. On expiration, the patient will expire gas past the expiratory valve 208, initially into the patient reservoir 218 and after the reservoir is full, along the overflow tube 210, past the interface 214 to the reusable structural portion to be discussed.

The single use patient circuit of FIG. 4B is very similar to that depicted in FIG. 4A except that in lieu of the expiratory valve 208 being connected between the elbow 200 and the entrance to overflow tube 210, in FIG. 4B the entrance 240 to the overflow tube is placed between the expiratory valve 242 and elbow fitting 200. The circuit of FIG. 4B may be preferred because in systems in accordance with the invention, it exhibits the same efficiency as the circuit of FIG. 4A and yet the expiratory valve 242 can be located close to the anesthesia machine where it's operation can be more readily observed by the anesthetist. Additionally, by not requiring that it be located close to the mask elbow, a larger, more reliable, lower pressure drop valve can be used.

Figures 5A, 5B, 5C:
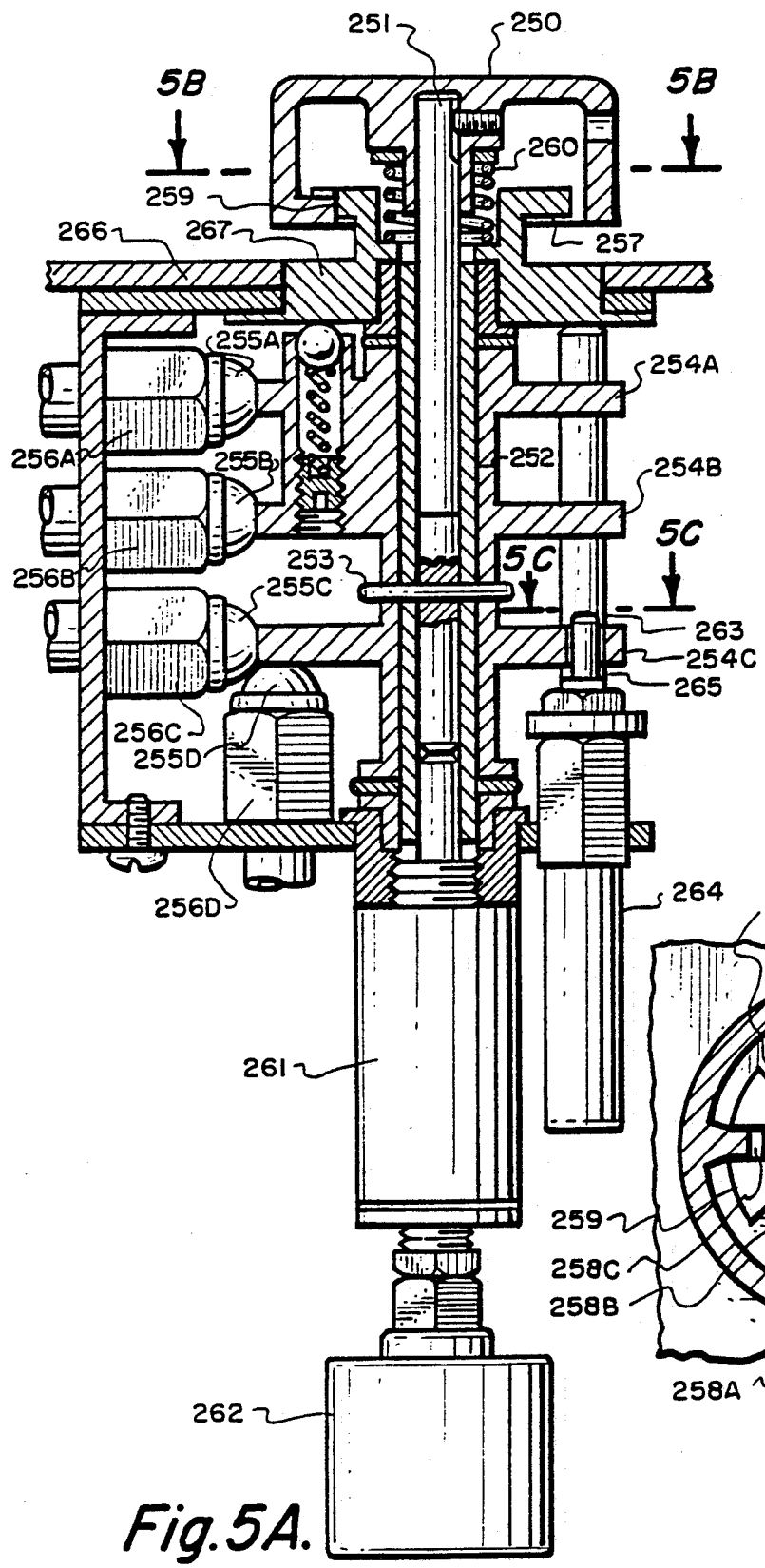
FIG. 5A is a sectional view illustrating a preferred control knob subassembly useful in the system embodiments of FIGS. 6A-6H and 7A-7J and FIGS. 5B and 5C are sectional views respectively taken along the planes 5B—5B and 5C—5C of FIG. 5A.

Prior to describing the detailed operation of system embodiment one (FIGS. 6A-6H) and system embodiment two (FIGS. 7A-7J), attention is directed to FIG. 5A which illustrates an exemplary control knob subassembly useful in both system embodiments. The control knob subassembly of FIG. 5A comprises a control knob 250 terminally secured to a central shaft 251 mounted for both rotational and axial movement. A hollow camshaft 252 is fitted around the shaft 251 and attached thereto by pin 253. Pin 253 is secured to camshaft 252 and extends through an axial slot in shaft 251. Thus, shaft 251 is able to move axially with respect to camshaft 252 but the shafts are secured together for rotation.

A plurality of cam members 254A, 254B, 254C extend radially from the camshaft 252. One or more cam followers 255A, 255B, 255C, 255D engage and follow the surfaces of the cams 254. Each cam follower is respectively coupled to a valve actuator 256A, 256B, 256C, 256D for controlling the ventilator/isolator functions as will be described hereinafter in connection with FIGS. 6A-6H and 7A-7J.

FIG. 5A further includes a fixedly mounted disc 257 having radial slots 258A, 258B, 258C, 258D, 258E, formed therein as shown in FIG. 5B. The control knob 250 includes an underhanging finger 259 located so as to normally be received in one of the slots 258 as a consequence of spring 260 urging the control knob 250 axially (upwards in FIG. 5A). As a consequence of the engagement between finger 259 and the slots 258A, 258B, 258C, 258D the control knob is normally detented in a fixed rotational position requiring that the user press the control knob inwardly to disengage finger 259 in order to change from certain rotational positions to other rotational positions. However, it should be noted that slot 258E defines an arcuate dimension much greater than that of the finger 259. Thus, when finger 259 is in slot 258E, the control knob 250 can be rotated through the arc of slot 258E. As will be seen hereinafter, this position is used in a manual bag mode to vary the opening of a overflow valve.

As depicted in FIG. 5A, valve bodies 261, 262 are located in line with shaft 251 so as to be actuated whenever the shaft 251 is pressed inwardly (downwardly in FIG. 5A). Valve bodies 261, 262 respectively comprise the dump valve and fill valve portions of the fix-it valve whose function will be discussed in significant detail in FIGS. 6A–6H and 7A–7J.

Attention is further called to arcuate slot 263 formed in cam 254C as shown in FIG. 5C. A pneumatic cylinder 264 is mounted so that cylinder lock pin 265 can extend through slot 263. With lockpin 265 engaged in slot 263, the control knob 252 can only be rotated through the limited arc defined by the slot 263. As will be understood in conjunction with FIGS. 6A–6H and 7A–7J, slot 263 permits the control knob 250 to be moved between the auxiliary outlet and off positions while 265 is engaged. When cylinder 264 is actuated to withdraw from slot 263, then the user is able to rotate the knob 250 to other rotational positions used for ventilating a patient. One of those positions is defined by the slot 258E which is used to variably control an overflow valve, as will be discussed, when operating in a manual bag mode.

The control knob subassembly further preferably includes a spring urged ball 266, rotatable with camshaft 252, for extending into shallow depressions 267 located in fixed relationship with respect to the disc 257. The shallow depressions 267 correspond to the slots 258. The ball/depression engagement provides the user with a better tactile feedback when the knob 250 moves into a detented position.

Attention is now directed to FIGS. 6A–6H which respectively depict the active structure and operation for each of multiple positions of the control knob 250 for system embodiment one. More specifically, the reader should understand that FIGS. 6A–6H are identical except that each depicts the flow paths made active at each different position of the camshaft 252, as represented in the upper left corner of each Figure by the position of the control knob pointer relative to a fixedly mounted escutcheon 275 bearing position labels. The reader should also understand that FIGS. 6A–6H depict only the reusable portion of the system to the left of interface line 214. The reusable portion is intended to functionally mate with the single use portion shown to the right of line 214 in either FIGS. 4A or 4B. It should also be recalled that although FIGS. 4A and 4B both depict 3-tube patient circuits, the system is also compatible with 2-tube patient circuits, as generally represented in FIGS. 2 and 3, and as will be further discussed hereinafter. It should also be recognized that the interface line 214 depicted in FIGS. 4A, 4B and FIGS. 6A–6H is intended to represent a functional interface. The corresponding structural interface between the single use and reusable structural portions, will be discussed hereinafter in connection with FIGS. 8–16.

Figure 6A:
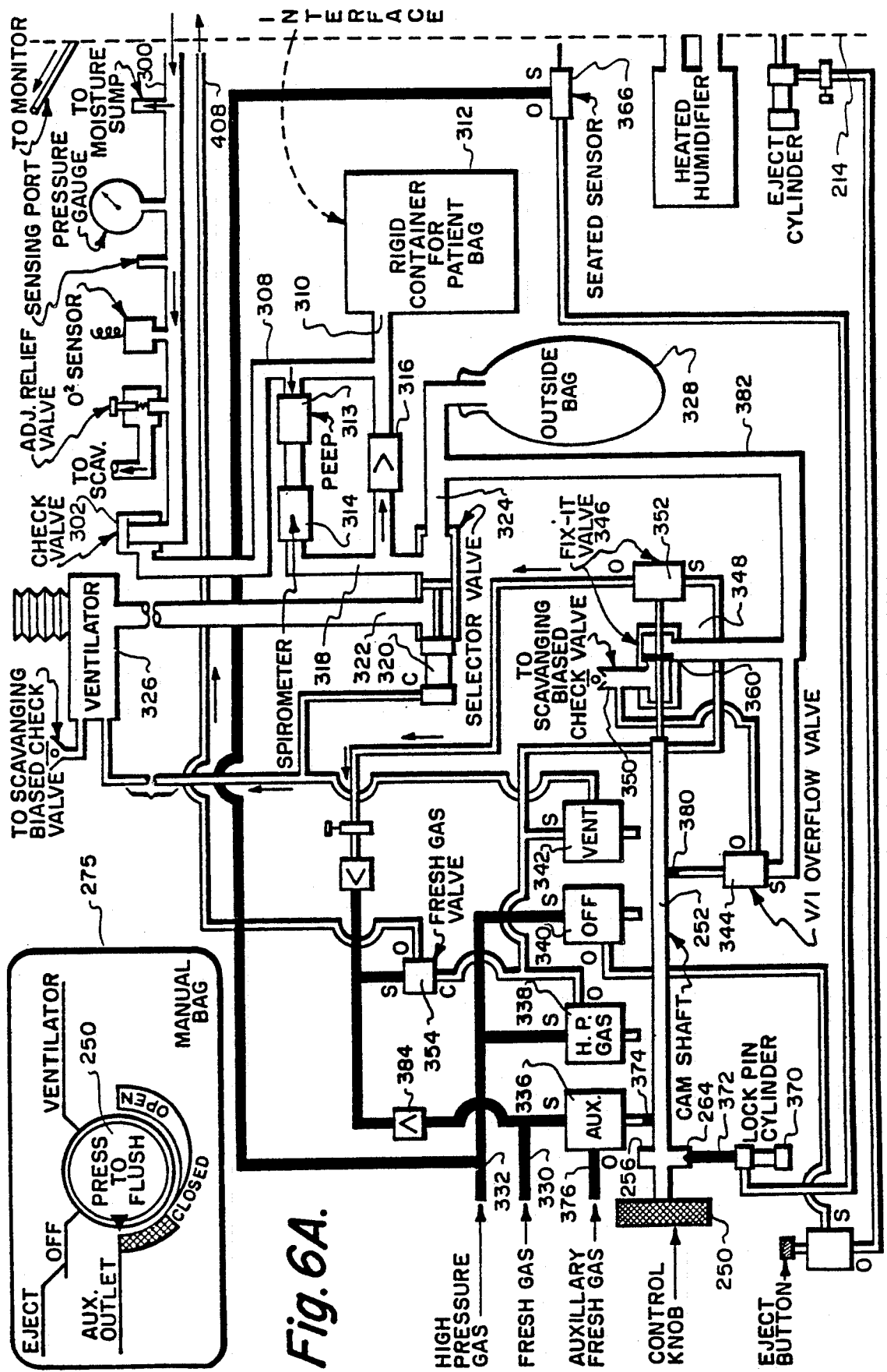

FIG. 6A depicts a tube 300 forming part of the reusable patient circuit portion, intended to be connected to overflow tube 210 of FIG. 4A. Tube 300 communicates with a check valve 302. Additionally a plurality of miscellaneous devices which are essentially conventional and do not uniquely relate to the present invention are depicted as being coupled to the tube 300. These miscellaneous devices include an outlet to a moisture sum, a pressure gauge, a sensing port, an oxygen sensor, and an adjustable relief valve. Similarly, other devices not critical to the novel aspects of the invention could also be connected to the tube 300.

The outlet side of the check valve 302 communicates via tubing 308 with the mouth 310 of rigid container 312 adapted to receive the patient bag 218 (FIG. 4A). Note that the tube 308 is coupled directly to the mouth 310 but that additionally a parallel path exists through an adjustable positive end expiratory pressure (PEEP) control device 313, a spirometer 314, and a check valve 316. A port 318 at the junction between spirometer 314 and check valve 316 communicates with the outlet of a selector valve 320. The selector valve 320 functions to couple either the mechanical ventilator path port 322 or the outside bag port 324 to the port 318. As will be discussed further hereinafter, the selector valve 320 functions to couple either the mechanical ventilator 326 or the outside bag 328 to the rigid container 312.

All of the elements discussed thus far connected to the outlet of the check valve 302 form part of a patient circuit control subsystem, generally referred to as the ventilator/isolator circuit. The ventilator/isolator circuit also includes the control knob 250, camshaft 252, and the various valves and tubing illustrated in FIG. 6A for controlling the flow of fresh anesthesia gas from supply inlet 330 and high pressure gas from supply inlet 332. The primary valves shown in FIG. 6A include a series of camshaft operated valves including auxiliary valve 336, high pressure gas valve 338, off valve 340, ventilator valve 342, an overflow valve 344. Each of these valves are cam controlled and thus are responsive to the rotational position of the camshaft 252. A further very significant valve, referred to as the fix-it valve 346, is actuated in response to the user pressing the control knob 250 axially. The fix-it valve 346 can properly be viewed as having a dump portion for communicating port 348 to biased check valve 350 and a fill portion or valve 352. Other primary valves, not directly operated by the camshaft 252 include a fresh gas valve 354 and the aforementioned selector valve 320. Various other valves and cylinders shown in FIG. 6A will be first mentioned in the course of discussing each operational mode depicted in FIGS. 6A–6H. In the upper left hand corner of each of FIGS. 6A–6H, the rotational position of the control knob 250 is shown. The axial position of the control knob in each of the Figures can be readily determined by the position of valve element 360 of the fix-it valve 346. Thus for example only, note that when the control knob is in its normal unpressed position, the valve element 360 is at its leftmost position. On the other hand, when the control knob 250 is pressed (e.g. FIG. 6F) note that the valve element 360 is at its rightmost position.

FIG. 6A shows the control knob 250 in the auxiliary outlet rotational position. It is assumed that a connector body of the single use portion has not yet been properly physically seated on the reusable portion. Thus the seated sensor 366 is not actuated and likewise the lockpin cylinder 370 is unactuated thereby leaving the lockpin 372 in its quiescent position engaged in aperture 264 of camshaft disc 256. With lockpin 372 so engaged, the control knob can not be rotated into any of the ventilating positions. In this position, the cam 374 opens the auxiliary valve 336 in order to couple the fresh gas supply inlet 330 to an auxiliary fresh gas outlet 376 for incidental use by the anesthetist. Note also that cam 380 opens overflow valve 344 which enables any excess pressure in the ventilator/isolator circuit, particularly the rigid container 312, outside bag 328 and tubing 382 to be evacuated past biased check valve 350. The outlet of biased check valve 350 is preferably coupled to a standard anesthesia scavenging system. FIG. 6A also shows that the fresh gas supply inlet 330 is made available via check valve 384 to the supply inlet of fresh gas valve 354 which at this time is closed. The high pressure gas inlet 338 is made available to the supply inlets of the valves 338 and 340 which at this time are also closed. Additionally, the high pressure gas supply inlet 332 is coupled to the seated sensor valve 366.

FIG. 6B illustrates the control knob 250 in the same rotational position but assumes that the single use connector body has now been properly seated. As a consequence, the pin 390 of the seated sensor valve 366 will be depressed, thus closing the valve 366 and applying high pressure gas to lockpin cylinder 370 to thus withdraw the lockpin 372 from disc aperture 264. This action now frees the control knob 250 enabling the user to rotate it to the ventilator position. It should be recalled that in order to rotate the control knob, it is first necessary to press it, as depicted in FIG. 5.

Figure 6C:
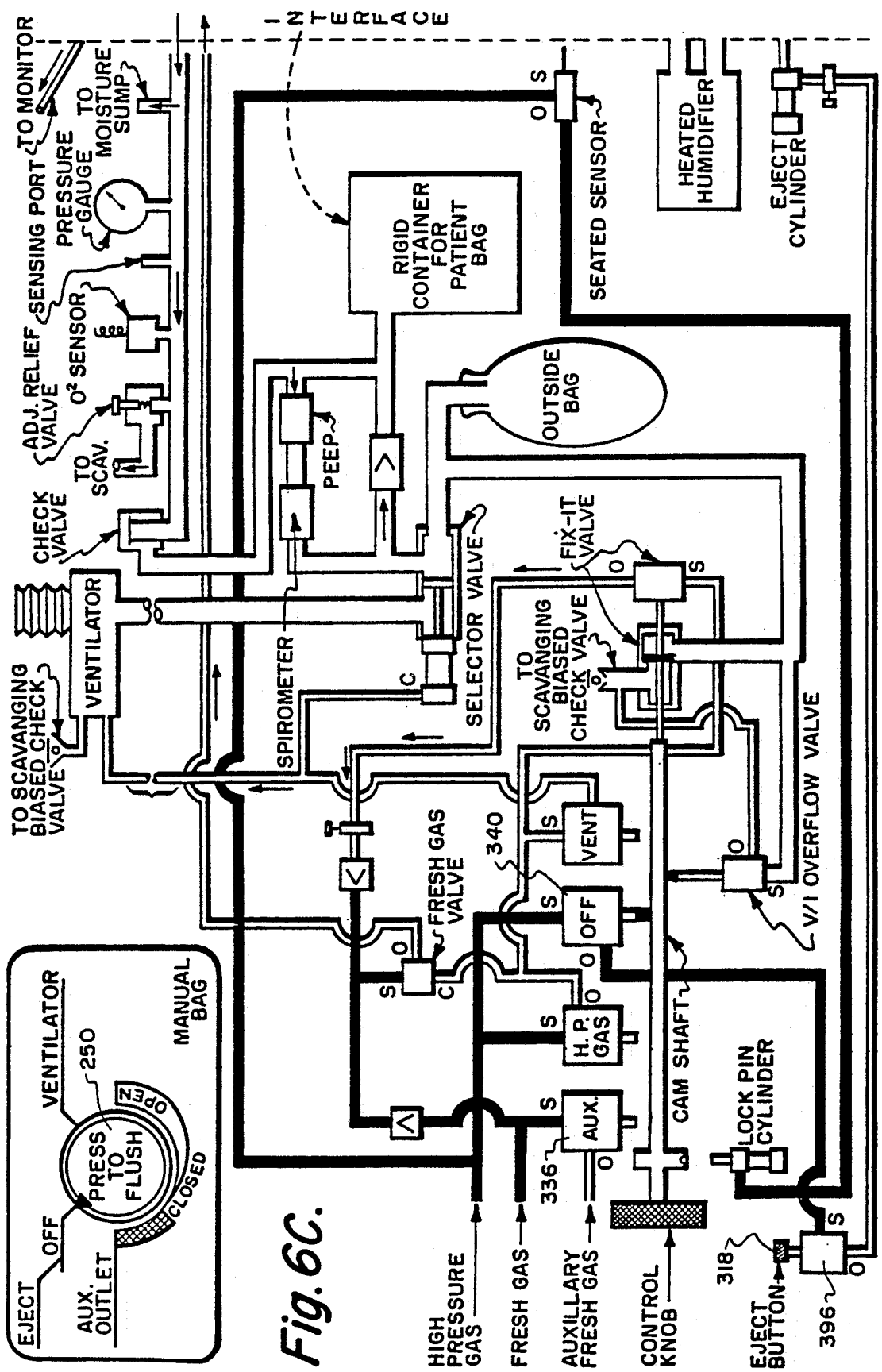

FIG. 6C shows the control knob 250 in the off position. Note in this position that the auxiliary valve 336 is no longer open. However, note that cam 394 has now opened off valve 340 to couple high pressure gas to eject valve 396. A user operable eject button 398 is provided to open the eject valve 396.

FIG. 6D is the same as FIG. 6C except that it represents eject button 398 being pressed to supply high pressure gas to eject cylinder 400, preferably via a needle valve 402. The eject cylinder 400 operates an axially movable pin 401, to be further discussed in connection with FIGS. 8-16, which operates first to unlatch the seated single use connector body and then to eject the connector body from the reusable mounting structure interface.

Figure 6E:
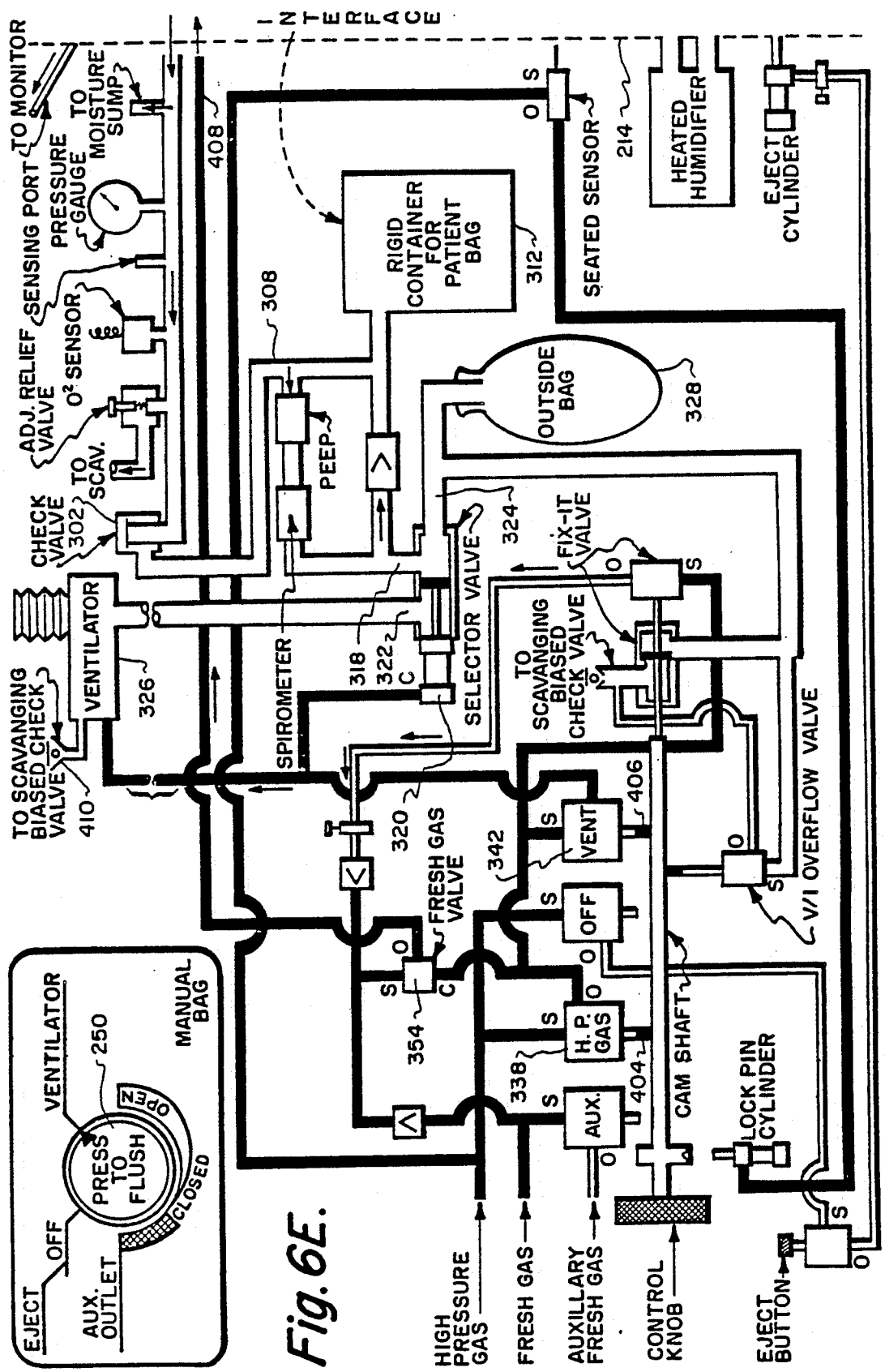

FIG. 6E shows the control knob 250 in the mechanical ventilator position. Note that in this position, cam 404 opens the high pressure gas valve 338 and cam 406 opens the ventilator valve 342. Actuation of the high pressure gas valve 338 supplies high pressure gas (dry medical grade oxygen) to the control port of fresh gas valve 354. As a consequence, fresh anesthesia gas available at the supply port of valve 354 is supplied via tube 408, across the interface 214 to the single use patient circuit (i.e. patient bag 218, tube 212 of FIG. 4A). Additionally, the open ventilator valve 342 supplies high pressure gas to the selector valve 320 to move its valve element to the right thus coupling ventilator port 322 to port 318, and closing port 324 to thus effectively remove the outside bag 328 from the circuit. The high pressure outlet from ventilator valve 342 is also supplied to the ventilator 326 for power. With this configuration, the pressure and volume in the rigid container 312, and as reflected in the patient bag 218, will be determined by the ventilator 326. Note that the patient expired gas exiting the overflow tube 210 (FIG. 4A) will flow past the check valve 302 into the tube 308 for use as ventilator/isolator circuit working gas. In this configuration, the biased check valve 410 of the ventilator 326 will function as the overflow valve for the ventilator/isolator circuit.

Figure 6F:
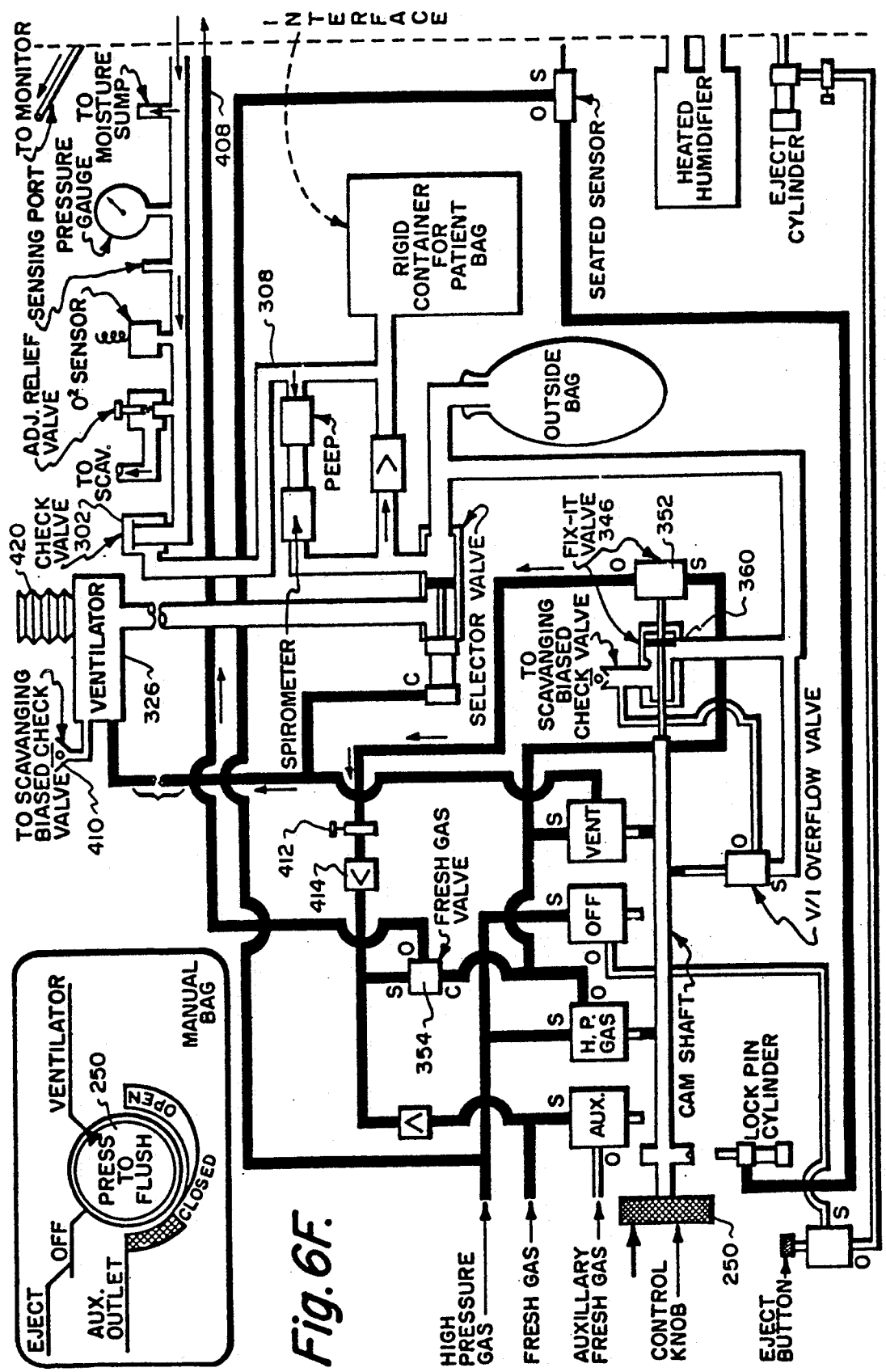
Figure 66:
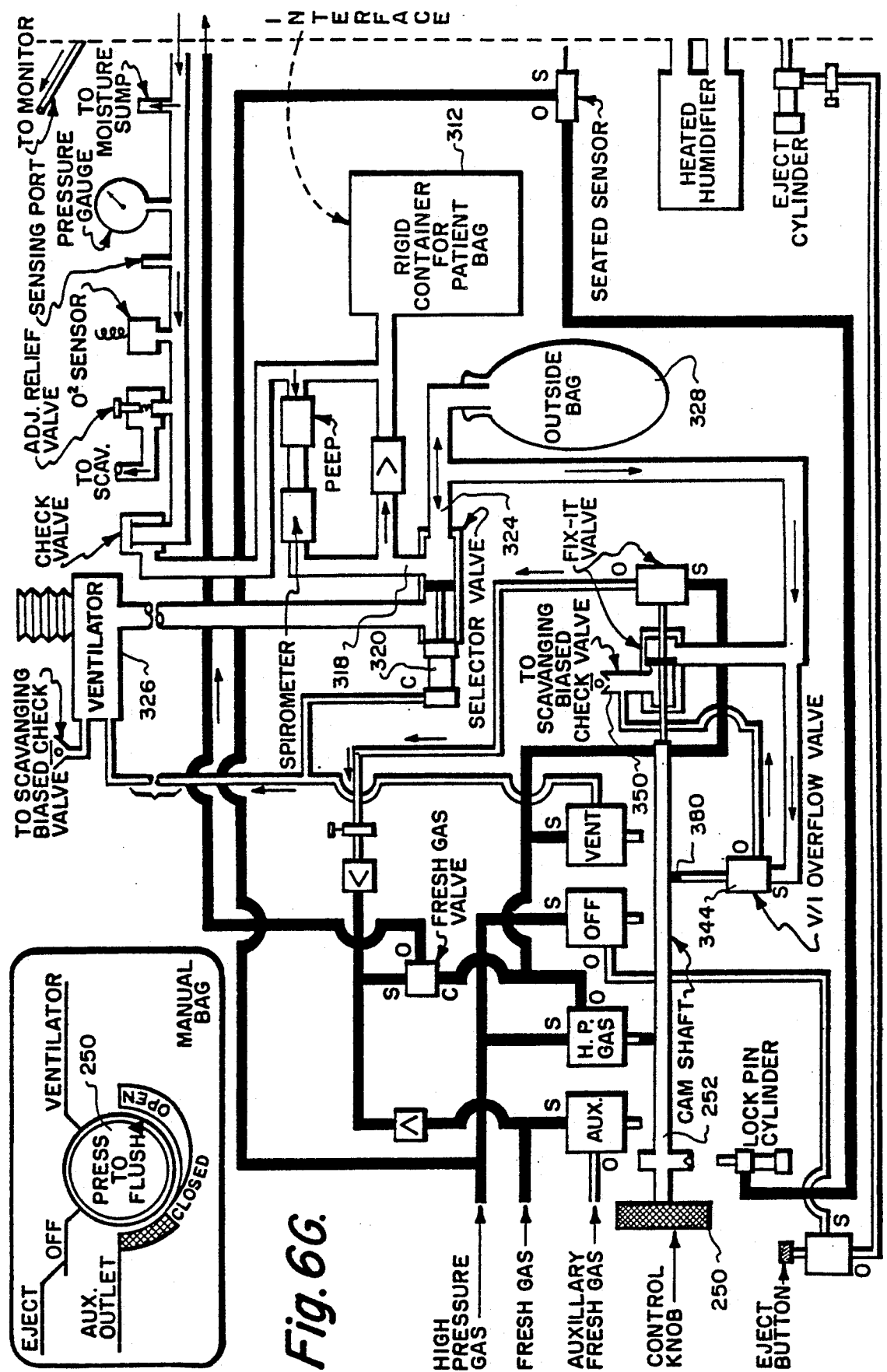

FIG. 6F shows the control knob 250 in the same ventilator position as represented in FIG. 6E but differs from 6E in that now the control knob 250 has been pressed to actuate the fix-it valve 346. Actuation of the fix-it valve in this condition, opens the full valve portion 352 to supply a high flow rate of high pressure gas, via the needle valve 412 and check valve 414 to the fresh gas valve 354. At this time, the fresh gas valve 354 is open and the addition of the high flow rate out of the valve 354 acts to flush both the patient circuit via tube 408 and the ventilator/isolator circuit as a consequence of the high gas flow rate returning via overflow tube 210 and check valve 302. For example only, the high flow rate supplied by fix-it valve 352 through gas valve 354 to the tube 408 can be on the order of 50-70 liters per minute whereas the normal fresh gas flow rate to the tube 408, as in FIG. 6E, is typically less than 10 liters per minute. Note further that as a consequence of the high pressure flow to the patient circuit and to the ventilator/isolator circuit, both circuits will be filled with gas, the ventilator bellows 420 will be inflated and the setting of the ventilator biased check valve 410 will determine the gas volume and pressure in both the patient and ventilator/isolator circuits. Thus, it is important to appreciate that as a consequence of pressing the control knob 250 to actuate the fix-it valve 346, the gas volume and pressure in both circuits can be rapidly adjusted to a predetermined level which, it will be recalled, has been referred to as an initialized condition. This feature of the system is extremely useful to an anesthetist because should any problem develop in the patient circuit or ventilator/isolator circuit, e.g. excessive pressure or insufficient gas volume in either, the condition can be immediately rectified by pressing the single control knob 250.

FIG. 6G shows the control knob 250 moved to the manual bag position. In this position, the cam 380 variably opens the overflow valve 344 as the control knob 250 and camshaft 252 are rotated. Note that in FIG. 6G, the selector valve 320 is in its unactuated position thereby communicating outside bag port 324 with port 318. This action removes the ventilator 326 from the circuit and instead connects the outside bag 328 to the ventilator/isolator circuit for controlling the gas volume and pressure in the rigid container 312. With the conditions shown in FIG. 6G, the anesthetist is now able to squeeze the outside bag 328 while also operating the variable overflow valve 344 (via the control knob 250) to control the pressure and volume in the patient and ventilator/isolator circuits. The outside bag 328 provides a tactile feedback to the user corresponding exactly to the action of the patient bag 218. Thus, as the user squeezes the outside bag 328, gas will be forced into the rigid container 312 and thus out of the patient bag 218. By controlling the overflow valve 344, the user is able to maintain a desired gas volume in the outside bag 328 and thus also the volume in the breathing bag 218. For example, if on patient expiration, the outside bag 328 is not being filled sufficiently, the user will close down the overflow valve 344. The pressure within the outside bag 328, when filled, is determined by the biased check valve 350. Note that when the patient is breathing spontaneously, overflow will occur through the overflow valve 344 and biased check valve 350 on expiration. On the other hand, when the patient is being assisted, i.e. the outside bag 328 is being squeezed, overflow will primarily occur during inspiration. The anesthetist can also operate in the manual bag mode to control, as contrasted with assisting, the patient's breathing, as for example in a situation where the patient is paralyzed. When operating in the manual bag controlled mode, overflow occurs via the overflow valve 344, just as in the manually assisted mode, primarily when the outside bag 328 is squeezed during inspiration by the patient.

It should be noted that overflow from the ventilator-/isolator circuit past overflow valve 344 will occur primarily during the inspiration phase, i.e. when bag 328 is being squeezed. On the other hand, overflow from the patient circuit past check valve 302 occurs only during the expiration phase.

Figure 6H:
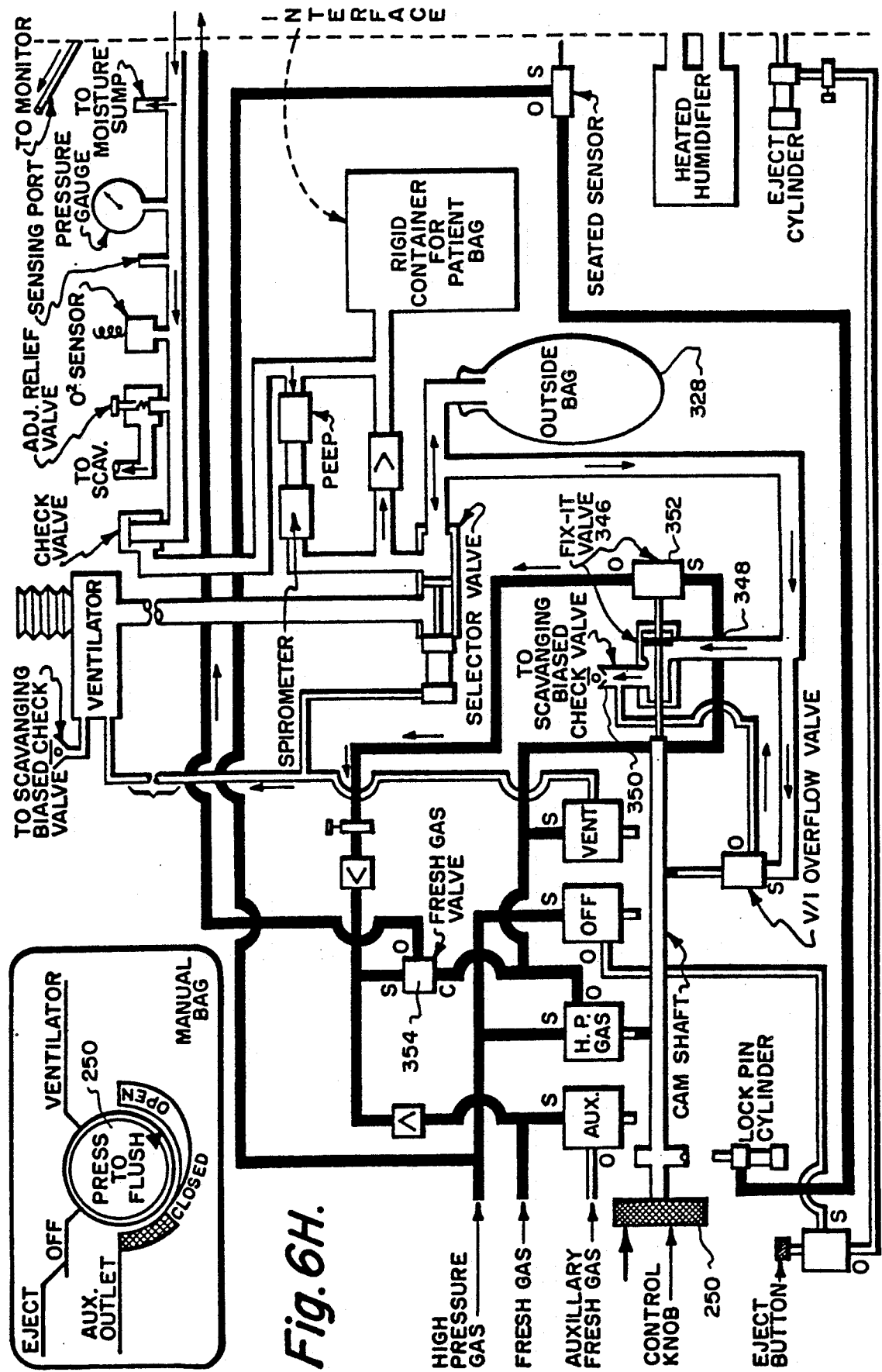

FIG. 6H shows the control knob 250 in the manual bag position, as in FIG. 6G, but with the control knob depressed to actuate the fix-it valve 346 and to open the port 348 to the biased check valve 350. The opening of the fill valve position 352 of the fix-it valve 346 supplies a high pressure flow to the fresh gas valve 354 to flush both the patient and ventilator/isolator circuits as was described in connection with FIG. 6F. Additionally, in the condition of FIG. 6H, the ventilator/isolator circuit, which here includes the outside bag 328, is vented from a port 348 past the dump portion of fix-it valve 346, i.e. open valve element 360, to the biased check valve 350. Consequently, the gas volume and pressure within the ventilator/isolator circuit will adjust to a level defined by the biased check valve 350, provided there is sufficient high pressure flow to the patient circuit via the fresh gas valve 354. Accordingly, it should again be recognized and appreciated that depression of the control knob 250 to actuate the fix-it valve 346 rapidly fills or dumps gas into or out of the patient circuit and ventilator/isolator circuit to adjust it to appropriate predetermined, i.e. initialized, conditions.

The following table I summarizes the valve actions for each of FIGS. 6A–6H.

TABLE I

| | | VENTILATOR-ISOLATOR | | | | |
|---|---|---|---|---|---|---|
| | | FIG. | 6A | 6B | 6C | 6D |
| VALVE AND CYLINDER OPERATION | | CONTROL KNOB POSITION | Auxilliary outlet | Auxilliary outlet | Off | Off |
| | | DISPOSABLE IN PLACE | No | Yes | Yes | Yes |
| NAME | ACTION | FLUSH VALVE PRESSED | | * | * | * |
| Seated Sensor 3-Way Valve | When Disposable Circuit is seated, high pressure gas goes to Lockpin Cylinder. | | | | | |
| Lockpin Cylinder Pneumatic Actuation | Lockpin restricts Control Knob to Auxilliary Outlet and Off Positions. | | in (Locked) | Out | Out | Out |
| Off Valve 3-Way-Cam Actuated | Sends high pressure gas to Disposable Circuit Eject Button. | | | | * | * |
| Eject Button 3-Way Valve Manual Actuation | Sends high pressure gas to the Eject Cylinder. | | | | | * |
| Eject Cylinder Pneumatic Actuation | Unlocks and ejects Disposable Circuit. | | | | | * |
| Auxil. Fresh Gas Valve 2-Way-Cam Actuated | Sends Fresh Gas to the Auxilliary Outlet. | | * | * | | |
| High Press. Gas Valve 3-Way-Cam Actuated | Sends high pressure gas to the Ventilator(s), Fresh Gas(c) & Flush(s) Valves | | | | | |
| Fresh Gas Valve 2-Way Pneumatic | Sends Fresh Gas to Disposable Patient Circuit. | | | | | |
| Flush(Fix-it)Valve. Plunger Actuated. Outside Bag Dump, Check Valve & 2-Way Valve | Sends high pressure gas to: Patient Circuit & opens the Outside Bag Dump Path. | | No Gas Supply | No Gas Supply | No Gas Supply | No Gas Supply |
| Ventilator Valve 3-Way-Cam Actuated | Sends high pressure gas to Ventilator & to move Selector Valve from Bag to Ventilator Position. | | | | | |
| Selector Valve & Cylinder. 2-Way, Pneumatic Actuation | Connects either Outside Bag or the Ventilator to the V/I Circuit. | | Bag | Bag | Bag | Bag |
| V/I Overflow Valve & Biased Check Valve. Manual Actuation | Vents excess gas from the V/I Circuit. Variable-Open to closed. | | Open | Open | Open | Open |

| | | FIG. | 6E | 6F | 6G | 6H |
|---|---|---|---|---|---|---|
| VALVE AND CYLINDER OPERATION | | CONTROL KNOB POSITION | Ventilator | Ventilator Bag | Manual Bag | Manual Bag |
| | | DISPOSABLE IN PLACE | Yes | Yes | Yes | Yes |
| NAME | ACTION | FLUSH VALVE PRESSED | | * | | * |
| Seated Sensor 3-Way Valve | When Disposable Circuit is seated, high pressure gas goes to Lockpin Cylinder. | | * | * | * | * |
| Lockpin Cylinder Pneumatic Actuation | Lockpin restricts Control Knob to Auxilliary Outlet and Off Positions. | | Out | Out | Out | Out |
| Off Valve 3-Way-Cam Actuated | Sends high pressure gas to Disposable Circuit Eject Button. | | | | | |
| Eject Button 3-Way Valve Manual Actuation | Sends high pressure gas to the Eject Cylinder. | | | | | |
| Eject Cylinder Pneumatic Actuation | Unlocks and ejects Disposable Circuit. | | | | | |
| Auxil. Fresh Gas Valve 2-Way-Cam Actuated | Sends Fresh Gas to the Auxilliary Outlet. | | | | | |
| High Press. Gas Valve 3-Way-Cam | Sends high pressure gas to the Ventilator(s), Fresh Gas(c) & Flush(s) Valves | | * | * | * | * |

TABLE I-continued
VENTILATOR-ISOLATOR

| | | | | | |
|---|---|---|---|---|---|
| Actuated Fresh Gas Valve 2-Way Pneumatic | Sends Fresh Gas to Disposable Patient Circuit. | * | * | * | * |
| Flush(Fix-it)Valve. Plunger Actuated. Outside Bag Dump, Check Valve & 2-Way Valve | Sends high pressure gas to: Patient Circuit & opens the Outside Bag Dump Path. | Dump Not in Circuit | * Dump Not in Circuit | | * |
| Ventilator Valve 3-Way-Cam Actuated | Sends high pressure gas to Ventilator & to move Selector Valve from Bag to Ventilator Position. | * | * | | |
| Selector Valve & Cylinder. 2-Way, Pneumatic Actuation | Connects either Outside Bag or the Ventilator to the V/I Circuit. | Ventilator | Ventilator | Bag | Bag |
| V/I Overflow Valve & Biased Check Valve. Manual Actuation | Vents excess gas from the V/I Circuit. Variable-Open to closed. | Open Not in Circuit | Open Not in Circuit | Variable | Variable |

It is pointed out that in order for the system of FIGS. 6A-6H to operate most effectively, the volumes of the outside bag 328 and patient bag 218 should be the same. Additionally, it is preferable that the patient bag 218 be formed of nondistensible material. The outside bag 328 preferably comprises a distensible breathing bag having the same tactile characteristics as conventional bags familiar to anesthetists.

Before proceeding to a discussion of the second system embodiment depicted in FIGS. 7A-7J, attention is directed to the aforementioned path in the ventilator/isolator circuit defined by the adjustable positive end expiratory pressure (PEEP) device 313, the spirometer 314, and the check valve 316. The purpose of the PEEP device 313 is to assure a positive end expiratory pressure in the patient overflow tube 210, and also in the patient bag 218, against which the patient breathes out. The check valve 316 in the lower limb of the parallel path shown in FIG. 6A is provided so that the gas flow into the rigid container 312 is unencumbered. The purpose of the spirometer 314 is to measure the volume of gas either inhaled or exhaled by the patient. Note that by locating the spirometer where indicated in FIG. 6A-6H, it is able to measure the volume of patient expired gas and yet not be crosscontaminated inasmuch as patient inspired gas does not come into contact with the spirometer. In the configuration shown, the spirometer 314 can be considered as measuring two gas component volumes on expiration. First, as the patient expires gas, he fills the patient bag 218, thus displacing some gas from the rigid container 312 through the spirometer. After the patient bag 218 fills, additional expired gas, and also any excess fresh gas, flows through the overflow tube 210, past the check valve 302, and then past the PEEP device 313 and the spirometer 314. The combined flow through the spirometer from the rigid container 312 and the patient overflow tube 210 gives an indication of the volume of expired gas, which in fact is greater than the actual volume of expired gas by the amount of fresh gas supplied during expiration.

In the system of FIGS. 6A-6H, it should be noted that the working gas for the ventilator/isolator circuit is derived via the patient overflow tube 210 and check valve 302. This gas of course includes patient expired gas which is generally humid and contaminated. Accordingly, over an extended period of use, the reliability of the various valve mechanisms, the mechanical ventilator 326, etc. could be adversely effected. Accordingly, the second system embodiment, depicted in FIGS. 7A-7J, uses high pressure dry oxygen for the ventilator/isolator circuit working gas thereby further enhancing system reliability.

Figure 7A:
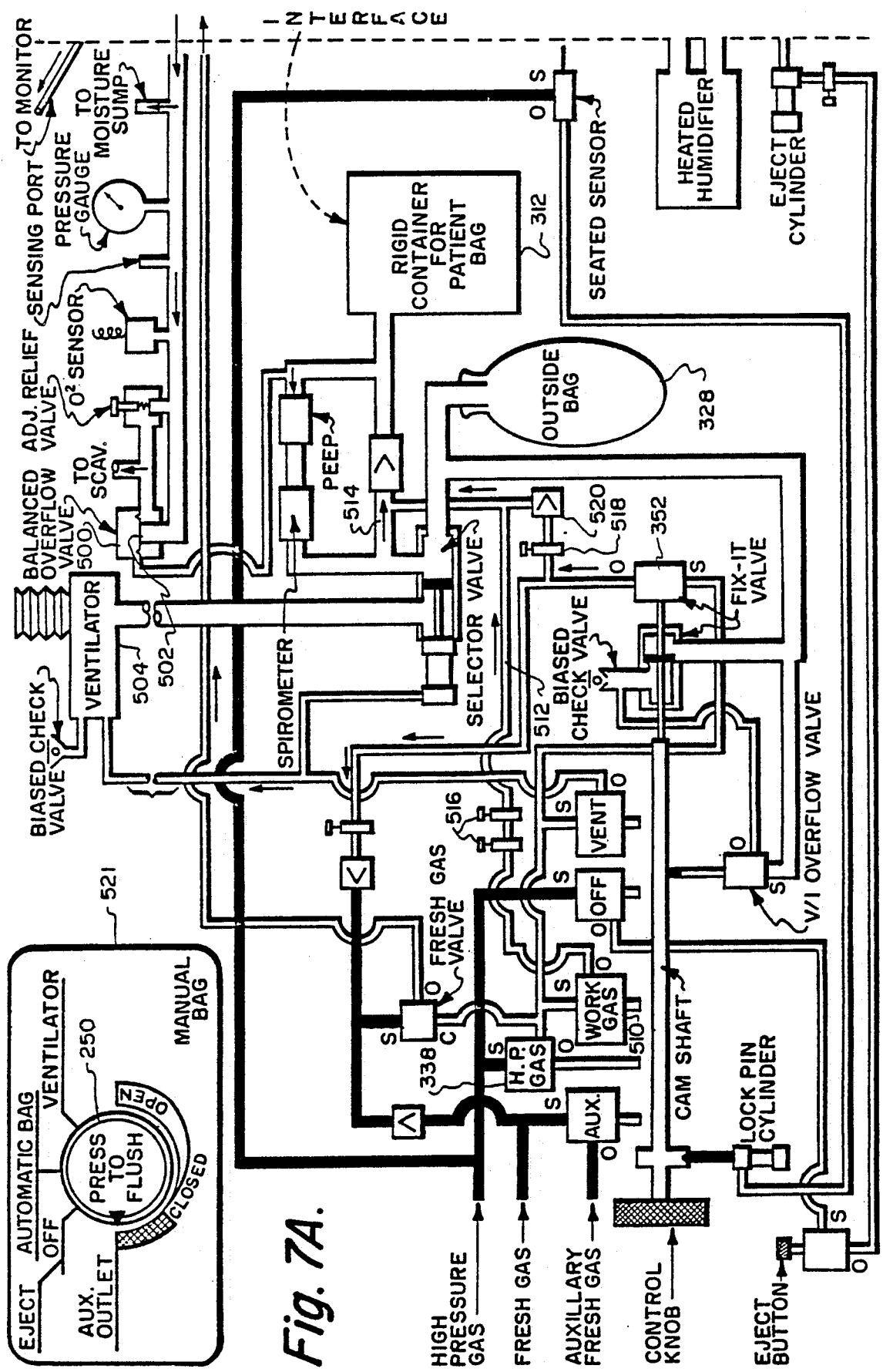
Figure 7D:
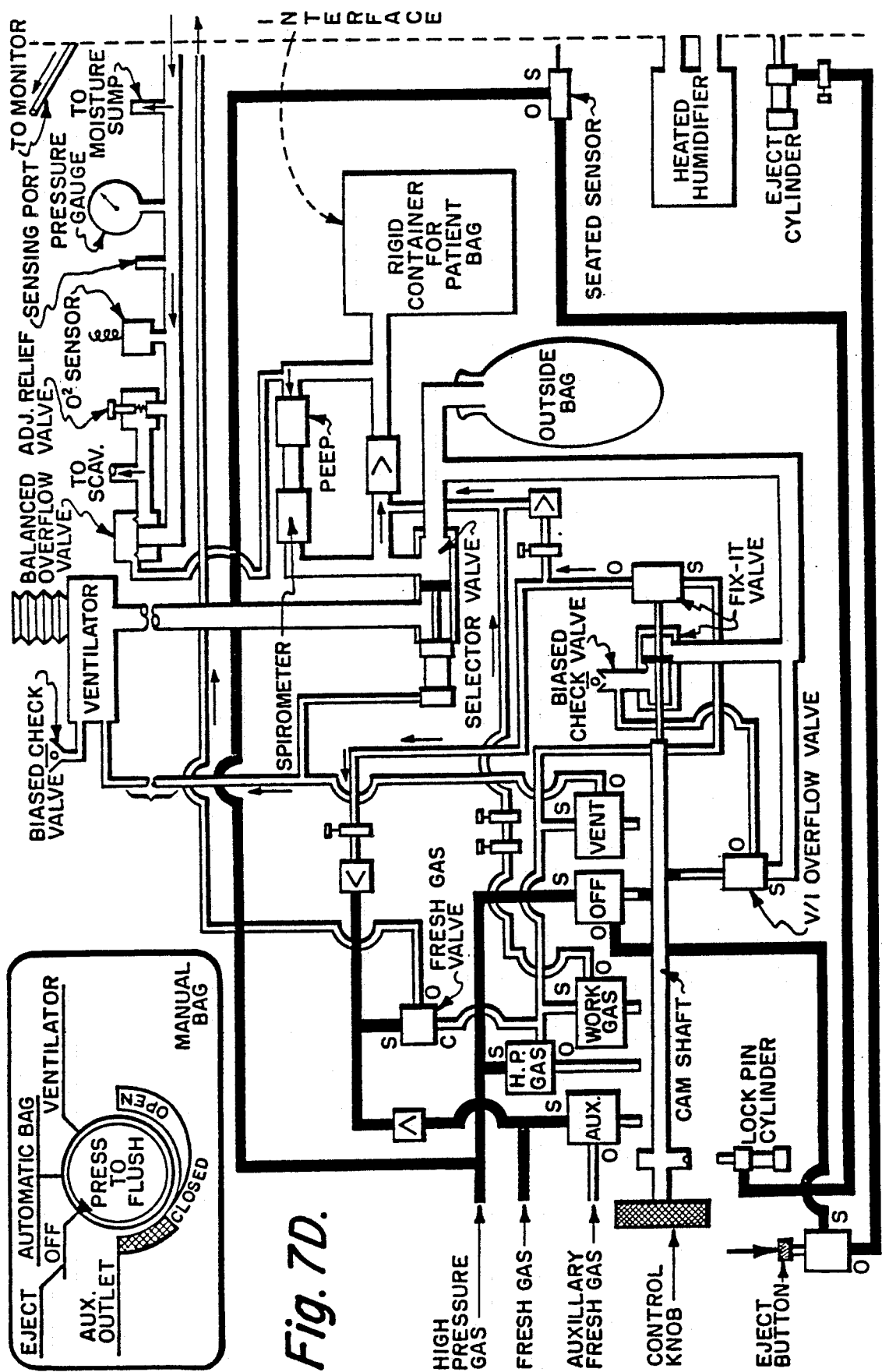

Comparing FIG. 7A to FIG. 6A, certain structural differences should be noted. Initially, in lieu of the check valve 302 in the patient circuit, a balanced overflow valve 500 is used. The balanced overflow valve 500 includes a diaphragm 502 defining an upper chamber 504. The gas pressure in the chamber 504 will be the same as that in the rigid container 312 as a consequence of tube 506. When the pressure in chamber 504 is sufficiently high, it will seal closed the patient overflow tube 210 and connected reusable overflow tube 300. When the pressure in the overflow tube 300 exceeds the pressure in chamber 504, then tube 300 is vented to the scavenging system as depicted in FIG. 7A. FIG. 7A further differs from FIG. 6A in that a cam operated working gas valve 510 is introduced. The supply port of gas valve 510 is derived from the outlet of the high pressure gas valve 338. The outlet of the working gas valve 510 is supplied via tube 512 to the ventilator/isolator circuit, at port 514. A needle valve 516 is preferably included between the working gas valve outlet and port 514. One further structural change to be noted in FIG. 7A is that the outlet of the fill portion 352 of fix-it valve 346 is additionally coupled through needle valve 518 and check valve 520 to the tube 512 and port 514.

The operation of the second system embodiment as depicted in FIGS. 7A-7D is identical to the operation of the first system embodiment depicted in FIGS. 6A-6D. Accordingly, the detailed description of the second embodiment will begin with FIG. 7E.

Figure 7E:
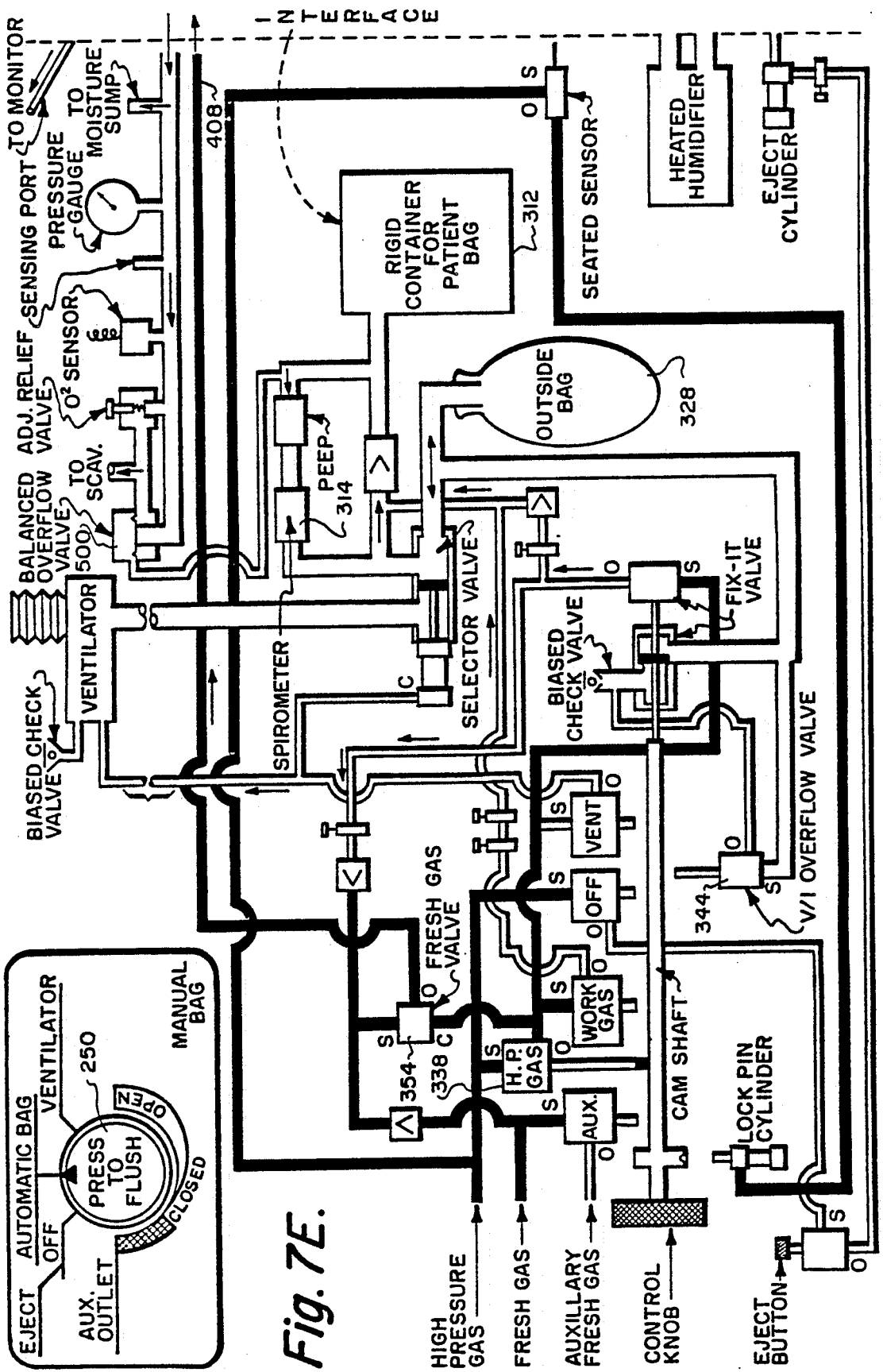
Figure 71:
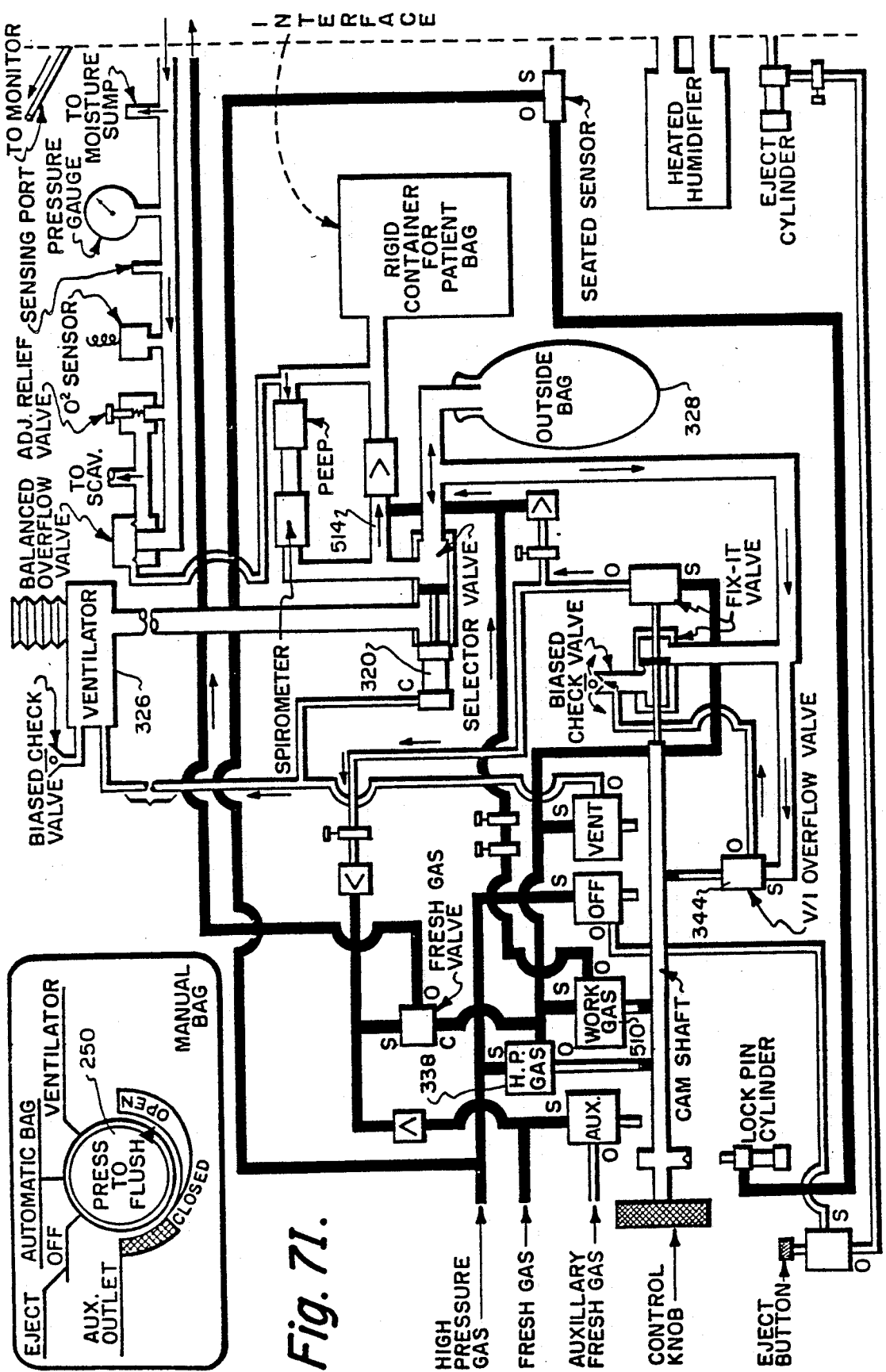

Further note in FIG. 7A that the escutcheon plate 521 around the control knob 250 defines an additional position as contrasted with the embodiment of FIG. 6A; i.e. an automatic bag position. FIG. 7E shows the control knob 250 in the automatic bag position at which high pressure gas valve 338 is cammed open thus supplying high pressure gas to the control port of the fresh gas valve 354 to thereby supply fresh anesthesia gas to the patient circuit via tube 408. In this automatic bag ventilating mode, the anesthetist can squeeze the outside bag 328 to pressurize the rigid container 312 to thus effectively squeeze the patient bag 218. Assuming no leaks in the system, the squeezing pressure applied to the outside bag 328 is correspondingly transferred to the patient bag. Note further that in this automatic bag mode, the overflow valve 344 is closed so that no gas is being vented from the ventilator/isolator circuit. Also note that no gas is being supplied to the ventilator/isolator circuit, i.e. outside bag 328, rigid container 312, etc. Thus, the ventilator/isolator circuit is essentially sealed. Assuming no leaks, the anesthetist will be able to manually squeeze the outside bag to correspondingly affect the patient bag without adjustment of any valves. Excess fresh gas supplied to the patient circuit will be vented via the patient overflow tube 210 and the balanced overflow valve 500 to the scavenging system. The automatic bag mode can be used by the anesthetist for manually assisted, manually controlled, or spontaneous ventilation with the anesthetist monitoring the patient's breathing, both visually and tactually, with reference to the outside bag 328. The spirometer 314 in this mode of operation reads only the displacement of the gas from the rigid container 312 which is exactly equal to the changes in volume of the patient bag 218. Thus, the spirometer will read low by the amount of fresh gas that flows into the patient circuit during inspiration.

FIG. 7F shows the automatic bag mode, as in FIG. 7E but additionally shows that a control knob 250 has been pressed to actuate the fix-it valve 346. Note that this action opens the fill valve 352 to supply high pressure gas to the supply port of the fresh valve 354 to flush the patient breathing circuit. The excess fresh gas supplied to the patient breathing circuit is vented via the balanced overflow valve 500 to the scavenging system. In order to also assure that the ventilator/isolator circuit is filled, note that the high pressure gas flowing out of the fix-it valve portion 356 will also be supplied via needle valve 518 and check valve 520 to the port 514 to fill the outside bag 328 and rigid container 312. Thus, when the control knob is pressed, if the patient circuit and/or ventilator/isolator circuit contained an insufficient gas volume, the high gas flow rate via fill valve 352 will rapidly refill the circuits. Note also that the dump portion of the fix-it valve, that is the communication from port 348 to the biased check valve 350 is also open when the control knob 250 is depressed. Thus, the biased check valve 350 will effectively limit or establish the gas volume and pressure in the ventilator/isolator circuit. It should be appreciated at this point that this gas volume and pressure established by the biased check valve 350 comprises the predetermined level which has sometimes here and before been referred to as the initialized condition. Inasmuch as the ventilator/isolator circuit communicates with the upper chamber 504 of the balanced overflow valve 500, via tube 506, biased check valve 350 will thus also set the initialized condition for the patient circuit. It should be noted that the inclusion of the needle valve 518, as well as the needle valve 412, enables the rate of filling the ventilator/isolator circuit and patient circuit, respectively, can be adjusted. Preferably, this would be a factor for a field technician adjustment.

FIG. 7G shows the control knob 250 in the mechanical ventilator position. In this mode, the working gas valve 510 is cammed on to supply working gas to the ventilator/isolator circuit via needle valve 516 (which is depicted as comprising two needle valve portions in series where it may be desirable to enable one to be factory or field technician adjustable and the other to be user adjustable) and then to port 514 for supply to the ventilator/isolator circuit. Also note in FIG. 7G that the ventilator valve 342 is cammed on to supply power gas to the ventilator and in addition to actuate selector valve 320. Note that actuation of selector valve 320 effectively removes the outside bag 328 from the ventilator/isolator circuit. Accordingly, the gas pressure and volume in the ventilator/isolator circuit will be controlled by the mechanical ventilator 326 and the ventilator biased check valve 410. The pressure in the ventilator/isolator circuit will, of course, be communicated via tube 506 to the upper chamber 504 of the balanced overflow valve 500 and thereby also determine the pressure of the patient circuit. As the ventilator periodically increases and decreases the pressure in the rigid container, the patient bag 218 will be correspondingly squeezed. The spirometer 314 will measure the gas exhausted from the rigid container 312 which will thus be a measure of the volume of gas transferred from the patient bag 218 to the patient. Thus the spirometer will underread the patient inspired gas by the amount of fresh gas supplied via tube 408 during inspiration.

FIG. 7H also shows the control knob in the ventilator position but note that it has now been pressed to open the fill portion 352 of the fix-it valve 346. As aforedescribed, this action will provide a high rate of gas flow via the fresh gas valve 354 to the patient circuit and via the needle valve 518 and port 514 to the ventilator/isolator circuit. As a consequence of the valve 500, the ventilator/isolator circuit pressure will establish the pressure in the patient circuit. The pressure in volume in the ventilator/isolator circuit in FIG. 7H will be determined by the ventilator biased check valve 410.

FIG. 7I shows the control knob 250 moved to the manual bag position. Note here that the high pressure gas valve 338 and working gas valve 510 are still cammed on to the supply working gas to the ventilator/isolator circuit via port 514. Also note that the position of the selector valve 320 removes the ventilator 326 from the ventilator/isolator circuit. Thus, the ventilator/isolator circuit pressure can be controlled by the anesthetist squeezing the outside bag 328. Note also that the overflow valve 344 is also cammed on enabling the user, by rotating control knob 250, to control the overflow out of the ventilator/isolator circuit. Consequently, by squeezing the bag 328 and adjusting the overflow valve 344, the user can readily control the action in the patient circuit, relying on the user's visual and tactile response to the outside bag. The spirometer 314 will function as previously described in connection with FIG. 7G.

Figure 7J:
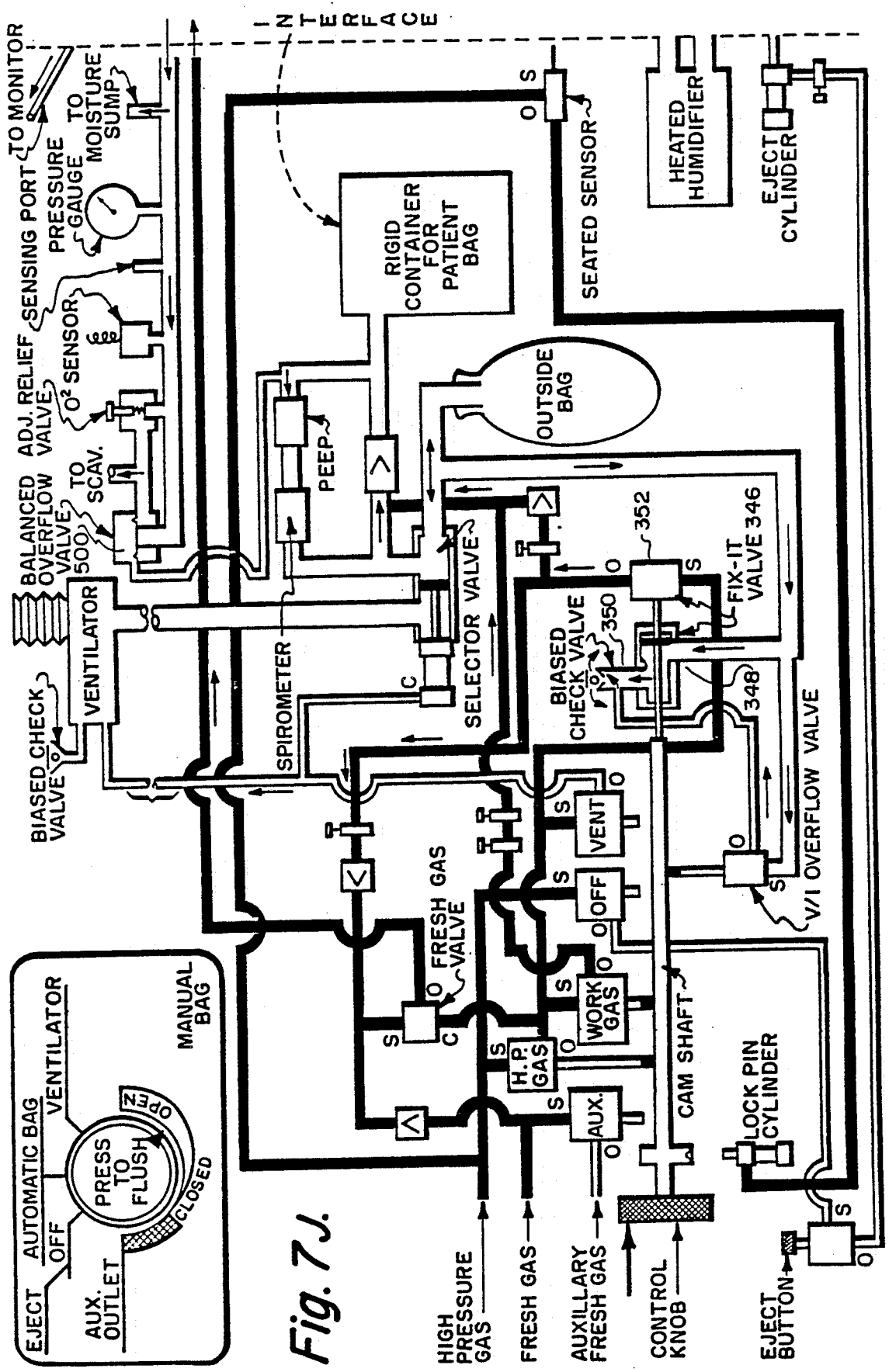
Figure 8:
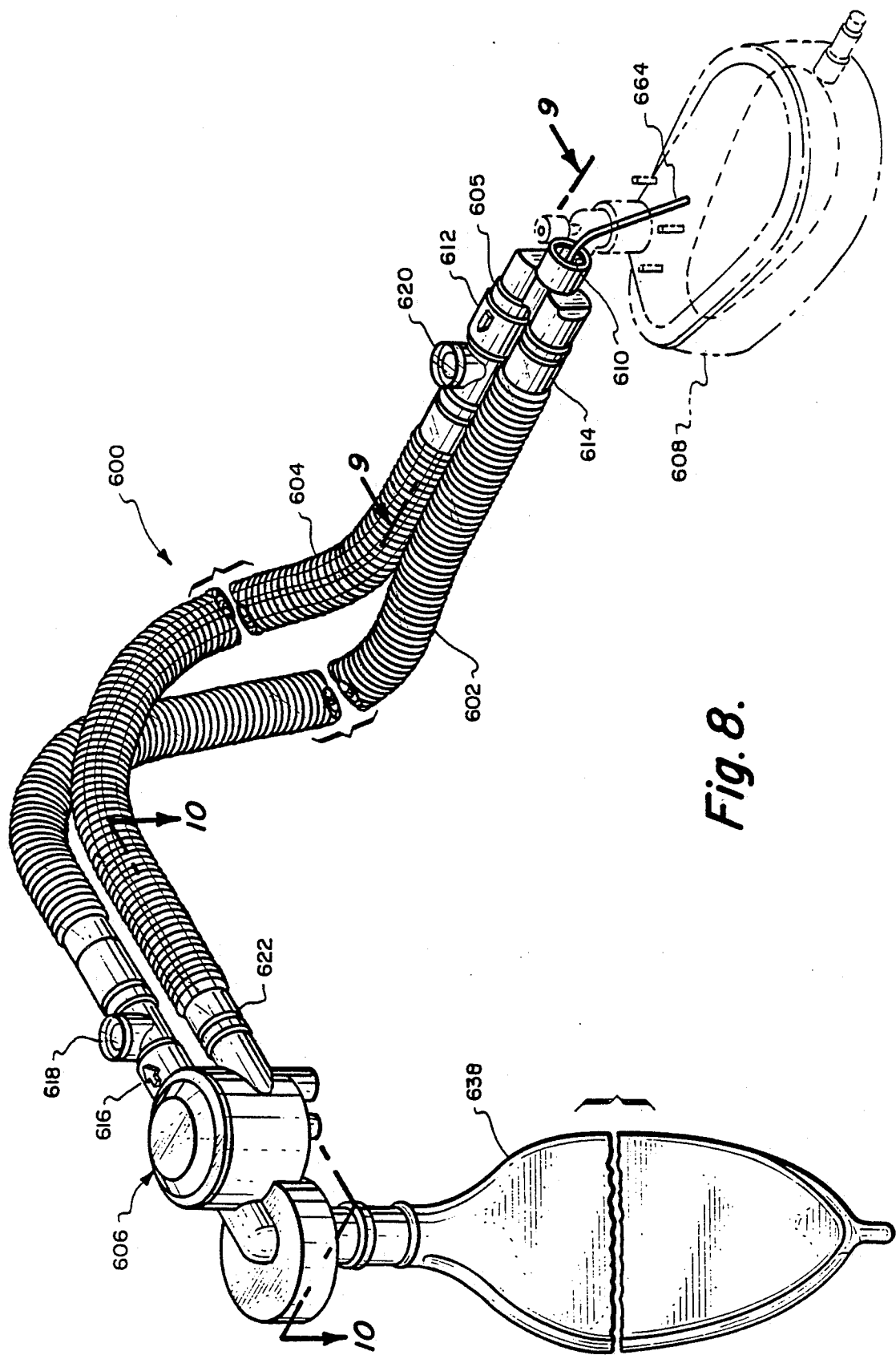
FIG. 8 is an isometric illustration of a preferred single use portion of the patient circuit depicted in FIG. 4.
Figure 9:
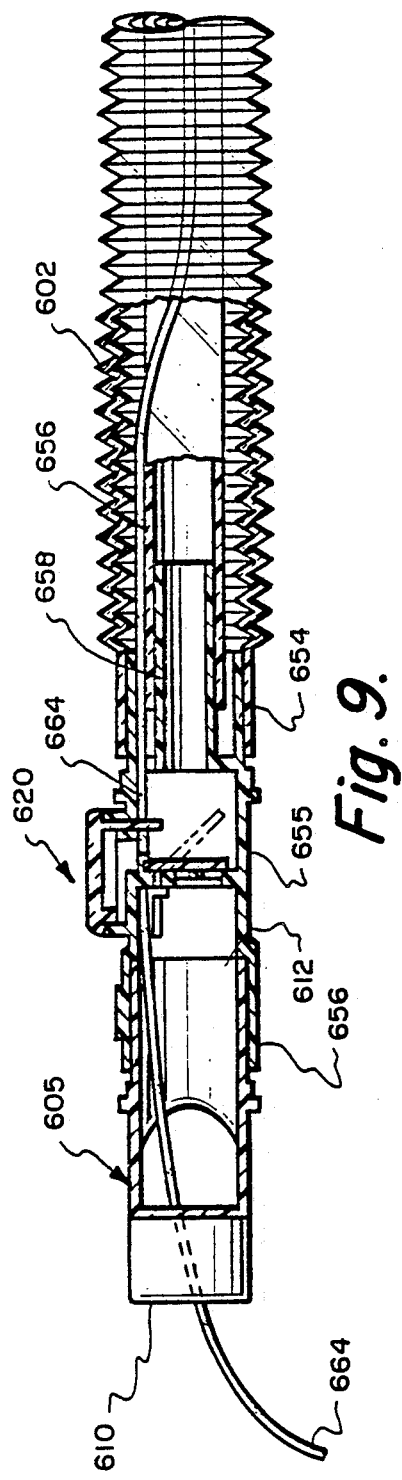
FIG. 9 is a sectional view taken substantially along the plane 9—9 of FIG. 8 showing the patient end of the expiratory tube including both the overflow tube and end expiratory monitoring tube fitted therethrough.

FIG. 7J shows the control knob 250 still in the manual bag position but now with the control knob pressed to actuate the fix-it valve 346, open the fill portion 352, and open the dump pathway via port 348 to the biased check valve 350. From what has previously been said, it should now be recognized that this action supplies a high gas flow rate to both the patient circuit and ventilator/isolator circuit to thus fill both circuits to the predetermined initial condition set by the biased check valve 350. That is, the pressure set by the biased check valve 350 and the ventilator/isolator circuit will be reflected in the patient circuit as a consequence of use of the balanced overflow valve 500.

The following table II summarizes the valve actions of system embodiment two in each of the configurations shown in FIGS. 7A-7J.

TABLE II

VENTILATOR-ISOLATOR

| VALVE AND CYLINDER OPERATION NAME | ACTION | FIG. CONTROL KNOB POSITION DISPOSABLE IN PLACE FLUSH VALVE PRESSED | 7A Auxilliary outlet No | 7B Auxilliary outlet Yes | 7C Off Yes | 7D Off Yes |
|---|---|---|---|---|---|---|
| Seated Sensor 3-Way Valve | When Disposable Circuit is seated, high pressure gas goes to Lockpin Cylinder. | | | * | * | * |
| Lockpin Cylinder Pneumatic Actuation | Lockpin restricts Control Knob to Auxilliary Outlet and Off Positions. | | in (Locked) | Out | Out | Out |
| Off Valve 3-Way-Cam Actuated | Sends high pressure gas to Disposable Circuit Eject Button. | | | | * | * |
| Eject Button 3-Way Valve Manual Actuation | Sends high pressure gas to the Eject Cylinder. | | | | | * |
| Eject Cylinder Pneumatic Actuation | Unlocks and ejects Disposable Circuit. | | | | | * |
| Auxil. Fresh Gas Valve 2-Way-Cam Actuated | Sends Fresh Gas to the Auxilliary Outlet. | | * | * | | |
| High Press. Gas Valve 3-Way-Cam Actuated | Sends high pressure gas to the Ventilator(s), Fresh Gas(c) & Flush(s) Valves | | | | | |
| Fresh Gas Valve 2-Way Pneumatic | Sends Fresh Gas to Disposable Patient Circuit. | | | | | |
| Working Gas Valve 2-Way-Cam Actuated | Sends Working (High Pressure) Gas to V/I Circuit | | | | | |
| Flush(Fix-it)Valve. Plunger Actuated. Outside Bag Dump, Check Valve & 2-Way Valve | Sends high pressure gas to: V/I circuit, Patient Circuit & opens the Outside Bag Dump Path. | | No Gas Supply | No Gas Supply | No Gas Supply | No Gas Supply |
| Ventilator Valve 3-Way-Cam Actuated | Sends high pressure gas to Ventilator & to move Selector Valve from Bag to Ventilator Position. | | | | | |
| Selector Valve & Cylinder. 2-Way, Pneumatic Actuation | Connects either Outside Bag or the Ventilator to the V/I Circuit. | | Bag | Bag | Bag | Bag |
| V/I Overflow Valve & Biased Check Valve Manual Actuation | Vents excess gas from the V/I Circuit. Variable-Open to closed. | | Open | Open | Open | Open |

| VALVE AND CYLINDER OPERATIONAL NAME | ACTION | FIG. CONTROL KNOB POSITION DISPOSABLE IN PLACE FLUSH VALVE PRESSED | 7E Automatic Bag Yes | 7F Automatic Bag Yes * | 7G Ventilator Yes |
|---|---|---|---|---|---|
| Seated Sensor 3-Way Valve | When Disposable Circuit is seated, high pressure gas goes to Lockpin Cylinder. | | * | * | * |
| Lockpin Cylinder Pneumatic Actuation | Lockpin restricts Control Knob to Auxilliary Outlet and Off Positions. | | Out | Out | Out |
| Off Valve 3-Way-Cam Actuated | Sends high pressure gas to Disposable Circuit Eject Button. | | | | |
| Eject Button 3-Way Valve Manual Actuation | Sends high pressure gas to the Eject Cylinder. | | | | |
| Eject Cylinder Pneumatic Actuation | Unlocks and ejects Disposable Circuit. | | | | |
| Auxil. Fresh Gas Valve 2-Way-Cam Actuated | Sends Fresh Gas to the Auxilliary Outlet. | | | | |
| High Press. Gas Valve 3-Way-Cam Actuated | Sends high pressure gas to the Ventilator(s), Fresh Gas(c) & Flush(s) Valves | | * | * | * |
| Fresh Gas Valve 2-Way Pneumatic | Sends Fresh Gas to Disposable Patient Circuit. | | * | * | * |
| Working Gas Valve 2-Way-Cam Actuated | Sends Working (High Pressure) Gas to V/I Circuit | | | | * |
| Flush(Fix-it)Valve. Plunger Actuated. Outside Bag Dump, Check Valve & 2-Way Valve | Sends high pressure gas to: V/I circuit, Patient Circuit & opens the Outside Bag Dump Path. | | | * | Dump Not in Circuit |
| Ventilator Valve 3-Way-Cam Actuated | Sends high pressure gas to Ventilator & to move Selector Valve from Bag to Ventilator Position. | | | | * |
| Selector Valve & Cylinder. 2-Way, Pneumatic Actuation | Connects either Outside Bag or the Ventilator to the V/I Circuit. | | Bag | Bag | Ventilator |
| V/I Overflow Valve & Biased Check Valve | Vents excess gas from the V/I Circuit. Variable-Open to closed. | | Closed | Closed | Open Not in Circuit |

TABLE II-continued
VENTILATOR-ISOLATOR

Manual Actuation

| VALVE AND CYLINDER OPERATION | | FIG. CONTROL KNOB POSITION DISPOSABLE IN PLACE FLUSH VALVE PRESSED | 7H Ventilator Yes * | 7I Manual Bag Yes * | 7J Manual Bag Yes * |
|---|---|---|---|---|---|
| NAME | ACTION | | | | |
| Seated Sensor 3-Way Valve | When Disposable Circuit is seated, high pressure gas goes to Lockpin Cylinder. | | * | * | * |
| Lockpin Cylinder Pneumatic Actuation | Lockpin restricts Control Knob to Auxilliary Outlet and Off Positions. | | Out | Out | Out |
| Off Valve 3-Way-Cam Actuated | Sends high pressure gas to Disposable Circuit Eject Button. | | | | |
| Eject Button 3-Way Valve Manual Actuation | Sends high pressure gas to the Eject Cylinder. | | | | |
| Eject Cylinder Pneumatic Actuation | Unlocks and ejects Disposable Circuit. | | | | |
| Auxil. Fresh Gas Valve 2-Way-Cam Actuated | Sends Fresh Gas to the Auxilliary Outlet. | | | | |
| High Press. Gas Valve 3-Way-Cam Actuated | Sends high pressure gas to the Ventilator(s), Fresh Gas(c) & Flush(s) Valves | | * | * | * |
| Fresh Gas Valve 2-Way Pneumatic | Sends Fresh Gas to Disposable Patient Circuit. | | * | * | * |
| Working Gas Valve 2-Way-Cam Actuated | Sends Working (High Pressure) Gas to V/I Circuit | | * | * | * |
| Flush(Fix-it)Valve. Plunger Actuated. Outside Bag Dump, Check Valve & 2-Way Valve | Sends high pressure gas to:V/I Circuit, Patient Circuit & opens the Outside Bag Dump Path. | | * Dump Not in Circuit | | * |
| Ventilator Valve 3-Way-Cam Actuated | Sends high pressure gas to Ventilator & to move Selector Valve from Bag to Ventilator Position. | | * | | |
| Selector Valve & Cylinder. 2-Way, Pneumatic Actuation | Connects either Outside Bag or the Ventilator to the V/I Circuit. | | Ventilator | Bag | Bag |
| V/I Overflow Valve & Biased Check Valve Manual Actuation | Vents excess gas from the V/I Circuit. Variable-Open to closed. | | Open Not in Circuit | Variable | Variable |

Attention is now directed to FIGS. 8–14 which depict a preferred structural embodiment of the single use portion of the patient circuit, implementing, for example, the circuit schematically shown in FIG. 4A. More particularly, the single use portion 600 is shown as including first and second corrugated tubes 602 and 604 connected between a Y-piece 605 and a connector body 606. The Y-piece 605 is intended to be connected to a mask elbow fitting and then to a mask 608 or endotracheal tube (not shown). The Y-piece is shown as including ports 610, 612, and 614. Tube 602 extends from a fitting 616 on the connector body through a coupling including inspiratory valve 618 and then to the port 614 on Y-piece 605. The tube 604 extends from the port 612 on Y-piece 605 through a coupling including expiratory valve 620 to fitting 622 on the connector body 606.

Figure 10:
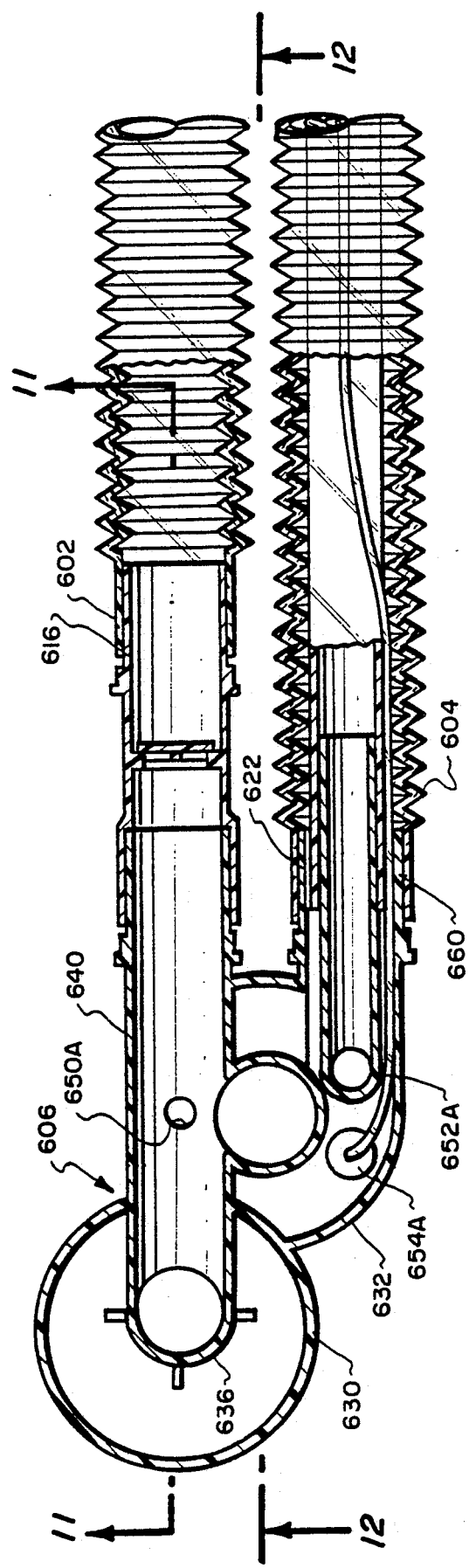
FIG. 10 is a sectional view taken substantially along the plane 10—10 of FIG. 8.

FIG. 10 best shows the structure of connector body 606. Note that it includes two substantially cylindrical structures 630 and 632. When seated in place on the reusable mounting structure (633 in FIGS. 12-14), the cylindrical portion 630 caps the rigid container 634 which, it will be recognized, corresponds to the rigid container 312 referred to in the system diagrams of FIGS. 6A-6H and 7A-7J. The cap portion 630 includes a depending nipple 636 around which the mouth of the patient bag 638 is secured. For enhanced reliability and lower cost, the bag 638 does not require a cuff but instead can be directly bonded to nipple 636. The patient bag 638 corresponds to the patient bag 218 referred to in the schematic diagram of FIG. 4A. Note in FIG. 10 that the nipple 636 communicates via a passageway 640 with the proximal end of inspiratory tube 602.

The cylindrical portion 632 of the connector body 606 defines three depending open nipples 650A, 652A and 654A. Note that nipple 650A communicates with the inspiratory tube 602 via the aforementioned passageway 640.

In accordance with a preferred configuration of the single use patient circuit 600, the patient overflow tube (210 in FIG. 4A) is threaded through the expiratory tube 604. Thus, as can be seen in FIG. 10, a tube 656 is provided extending the full length of tube 604 from the expiratory valve 620 to the connector body 606. More particularly, the valve 620 (FIG. 9) is housed in fitting 655 having a first tubular end 656, preferably bonded to the Y-piece 605. The proximal end of fitting 655 terminates in spaced concentric nipples 657, 658. The distal end of expiratory tube 604 is preferably bonded to the outer nipple 657 providing a gas passageway from tube 604, through the space between nipples 657 and 658, to the valve 620. The overflow tube 656 is fitted on and preferably bonded to inner nipple 658.

The proximal end of expiratory tube 604 is fitted around and preferably bonded to nipple 622 on connector body 606. An inner nipple 660 is concentrically mounted within nipple 622 in communication with nipple 652A. The distal end of overflow tube 656 is mounted on and preferably bonded to nipple 660 to thus communicate it with nipple 652A.

The proximal end of inspiratory tube 602 is preferably removably mounted on nipple 662 of inspiratory valve fitting 663 to enable the tube 602 to be coupled to the heated humidifier apparatus of FIGS. 6A-6H an 7A-7J. The heated humidifier apparatus is of conventional design and includes a single use cartridge.

In accordance with a further aspect of the preferred single use patient circuit 600, an end expiratory monitoring tube 664 is threaded through the expiratory tube 604 extending from beyond the port 610 in the Y-piece 605 to the nipple 654A (FIG. 10) past the expiratory valve 620.

Figure 14:
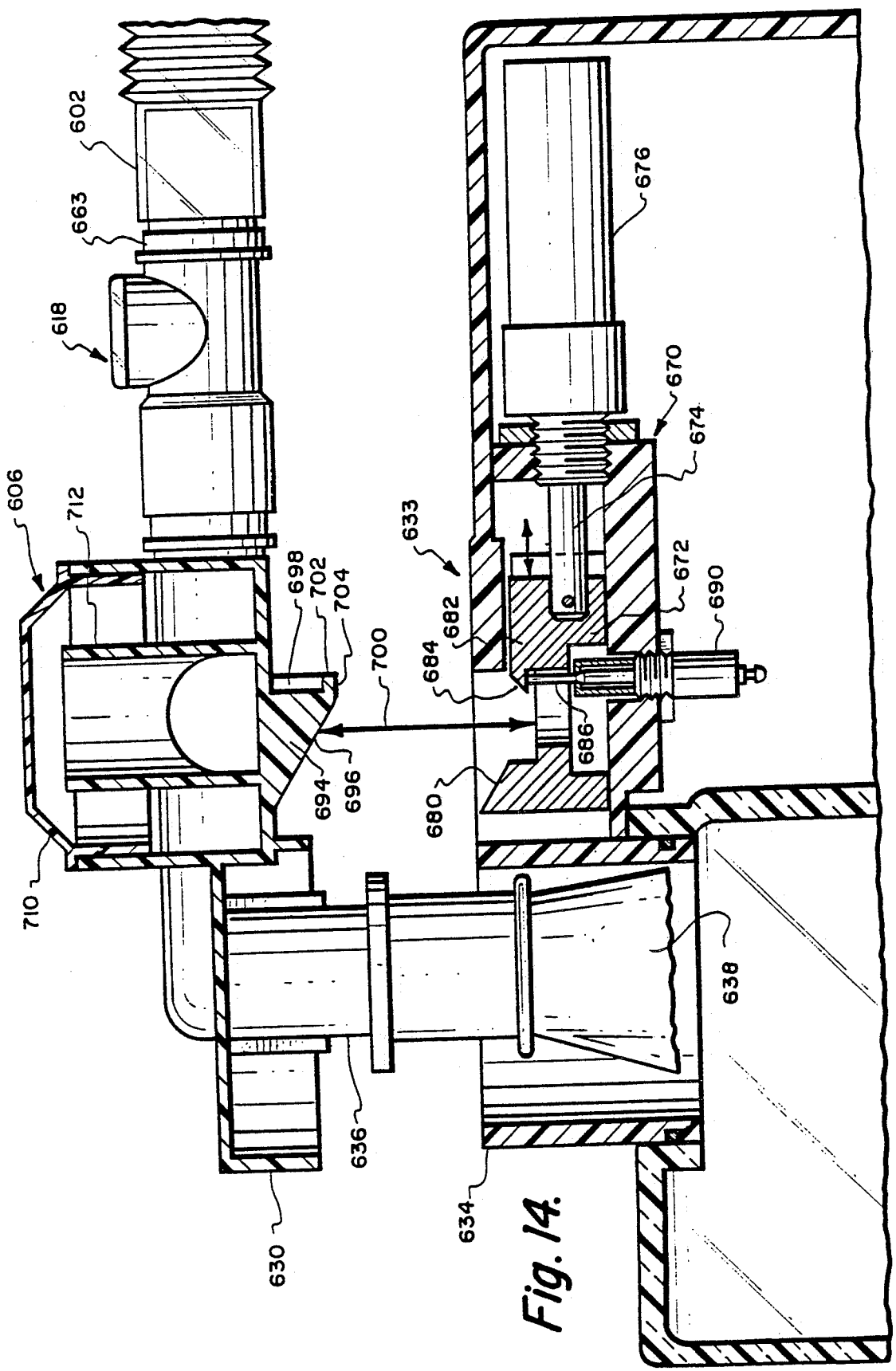
FIG. 14 is a sectional view substantially identical to that of FIG. 12 but however showing the single use connector body displaced from the structural mounting interface of the reusable system portion.

The connector body 606 is configured so that when it is properly seated on the mounting structure of the reusable portion, all of the nipples 650A, 652A, 654A mate with corresponding tubular openings 650B, 652B, 654B in the reusable mounting structure 633 (FIGS. 12-14). Nipple 650B opens to the fresh gas supply, e.g. 408 in FIG. 6A. Nipple 652B opens to the overflow tube 300 in FIG 6A. Nipple 654B communicates with a tube (not shown) extending through the control arm 50 (FIG. 1), emerging therefrom at 46 for coupling to instruments 44.

The connector body 606 is additionally configured so that when placed on the reusable mounting structure, it is automatically latched in place and cannot be removed until the aforementioned eject button 398 is depressed (FIG. 6D).

Attention is particularly directed to FIGS. 12 and 14 which illustrate the structural interface between the connector body 606 and the reusable mounting structure 633. Initially note in FIG. 14 that the reusable mounting structure 633 includes a slide member 672 connected to an axial pin 674 associated with a pneumatic cylinder 676. Note that the pin 674 and cylinder 676 respectively correspond to the pin 401 and cylinder 400 referred to in FIG. 6D. The pin 674 is axially spring urged to the left (as seen in FIG. 14) and is moved to the right when the cylinder 676 is actuated. Note that the slide 672 has a first inclined surface 680. Also note that the slide 672 includes a projecting latch member 682 having an inclined upper surface 684. Note also in FIG. 14 that a pin 686, associated with a valve body 690 is located beneath the latch member 682. The pin 686 and valve body 690 correspond respectively to the pin 390 and seated sensor valve 366 previously discussed in connection with FIG. 6B. When the pin 686 is in the position depicted in FIG. 14, the seated sensor valve 366 is open.

The connector body 606 further includes a depending member 694 having a ramp surface 696. The member 694 is undercut to define a slot 698 for receiving the latch member 682. The member 694 terminates in a projection 702 having a flat surface 704.

With reference to FIG. 14, assume now that the connector body 606 is lowered onto the mounting structure 670, with the nipples 650A, 652A, 654A respectively extending into tubular openings 650B, 652B, 654B, as represented by the arrow 700. As the connector body is lowered, the flat portion 704 of the depending ramp member 694 will contact the inclined surface 684 of the latch member 682 to thus move the slide 672 to the right against its spring urging. After the projection 702 moves past the latch member 682, the spring bias will force the slide 672 to the left moving the latch member 682 into the slot 698 of the connector body as depicted in FIG. 12. With connector body 606 so latched to the mounting structure 670, as a consequence of the interference between the latch member 682 and projection 702, the connector body, once seated, cannot be manually removed. Note also that as a consequence of placing the connector body 606 on the mounting structure 670, the pin 686 is depressed by flat portion 704 to thus open the valve 366 (FIG. 6B). With the connector body 606 so mated to the reusable mounting structure 633, the aforementioned nipples 650A, 652A, and 654A will be automatically mated to the tubular openings 652B, 652B and 654B in the reusable portion.

In order to unlatch the connector body 606, it will be recalled from FIG. 6D that the eject button 398 is depressed to actuate the eject cylinder 400. The schematically illustrated eject cylinder 400 in FIG. 6D corresponds to the structural cylinder 676 illustrated in FIG. 14. Actuation of the cylinder 676 pulls the axial pin 674 to the right (FIG. 14) thus pulling the latch member 682 out of the slot 698 thereby freeing the projection 702 enabling the connector body 606 to be lifted from the reusable mounting structure 670. In addition to unlatching the connector body, in accordance with the preferred embodiment disclosed in FIGS. 8-14, actuation of the cylinder 676 to pull the slide 672 to the right, also pulls inclined surface 680 into contact with ramp surface 692 on the connector body 606. Thus, after the latch member 682 has first been withdrawn from the slot 698, the engagement of inclined surface 680 against the ramp surface 696 will force the connector body 606 upwardly, that is, ejecting it from the reusable mounting structure 633.

It will be recalled from FIGS. 4A and 4B that under some circumstances, it may be desirable to incorporate $CO_2$ absorber material into the patient circuit. In order to permit a $CO_2$ absorber canister to be used in conjunction with the 3-tube patient circuit of FIGS. 8-14, the connector body 606 is provided with a removable cap 710. An open nipple 712, communicating with the passageway 640 (and thus with patient bag nipple 636, fresh gas nipple 650A, an inspiratory tube 602) is located immediately beneath the cage 710 for mounting the $CO_2$ canister.

Figure 15:
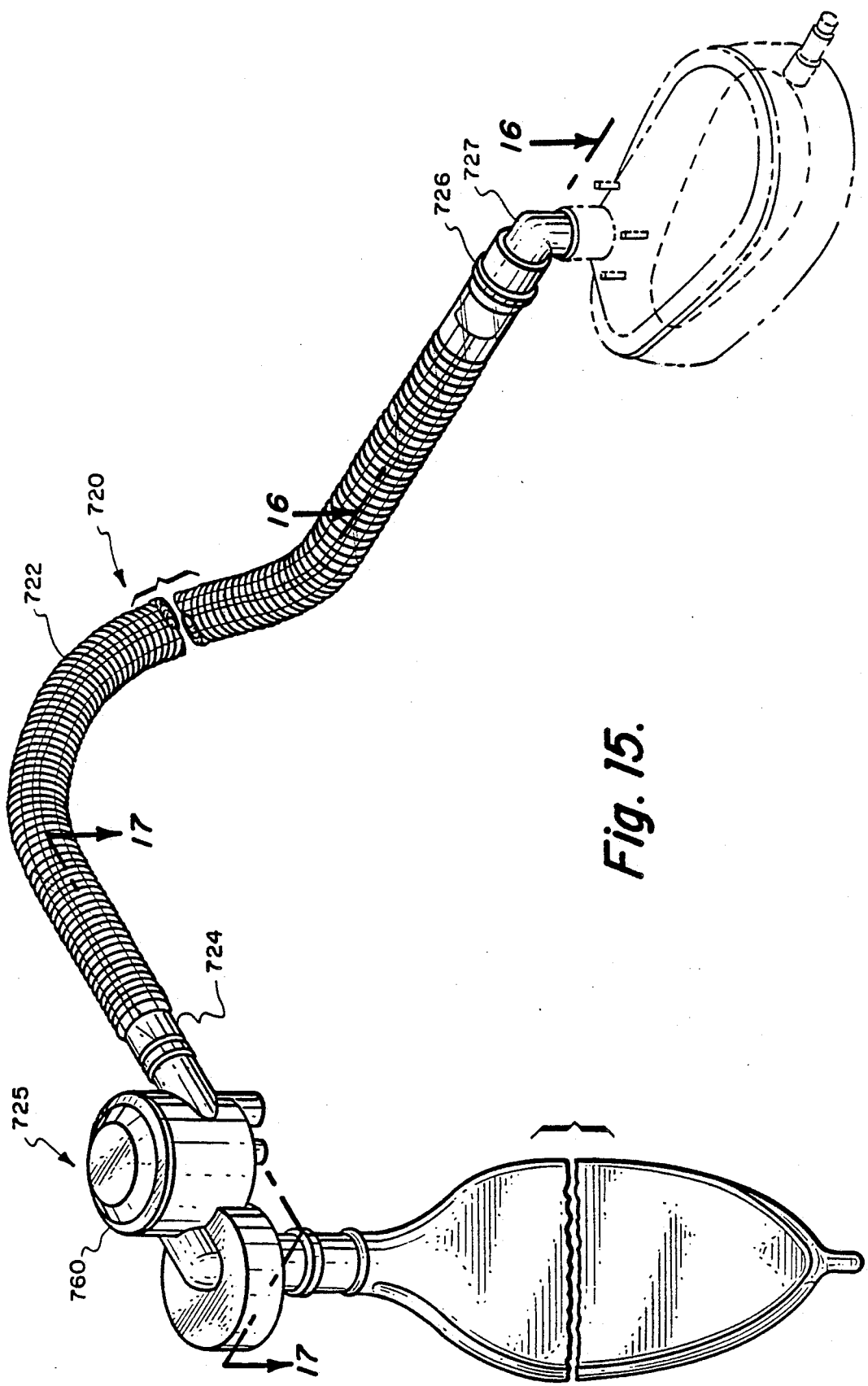
FIG. 15 is a sectional view of the single use portion of a 2-tube patient circuit in accordance with the present invention.
Figure 16:
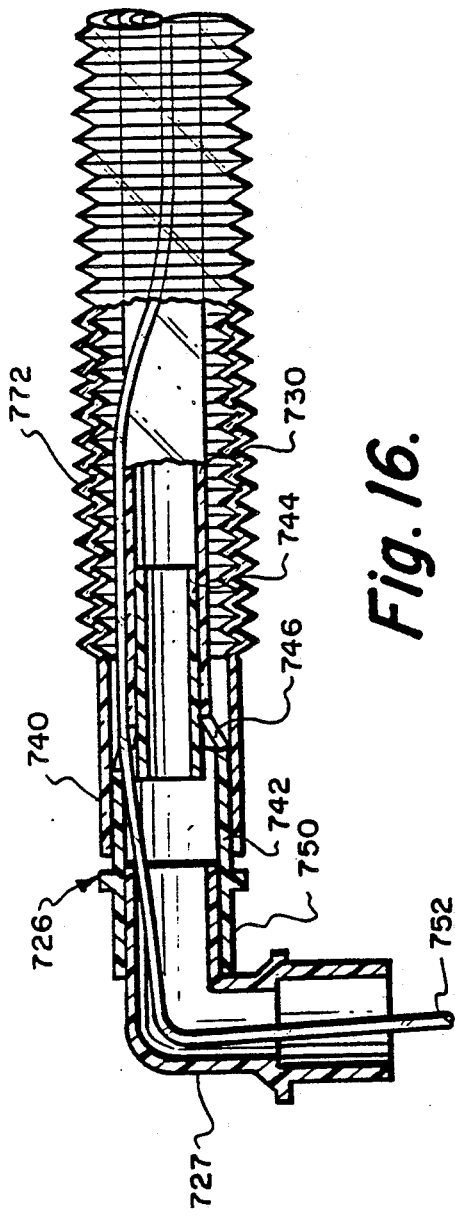
FIG. 16 is a sectional view taken substantially along the plane 16—16 of FIG. 15.
Figure 17:
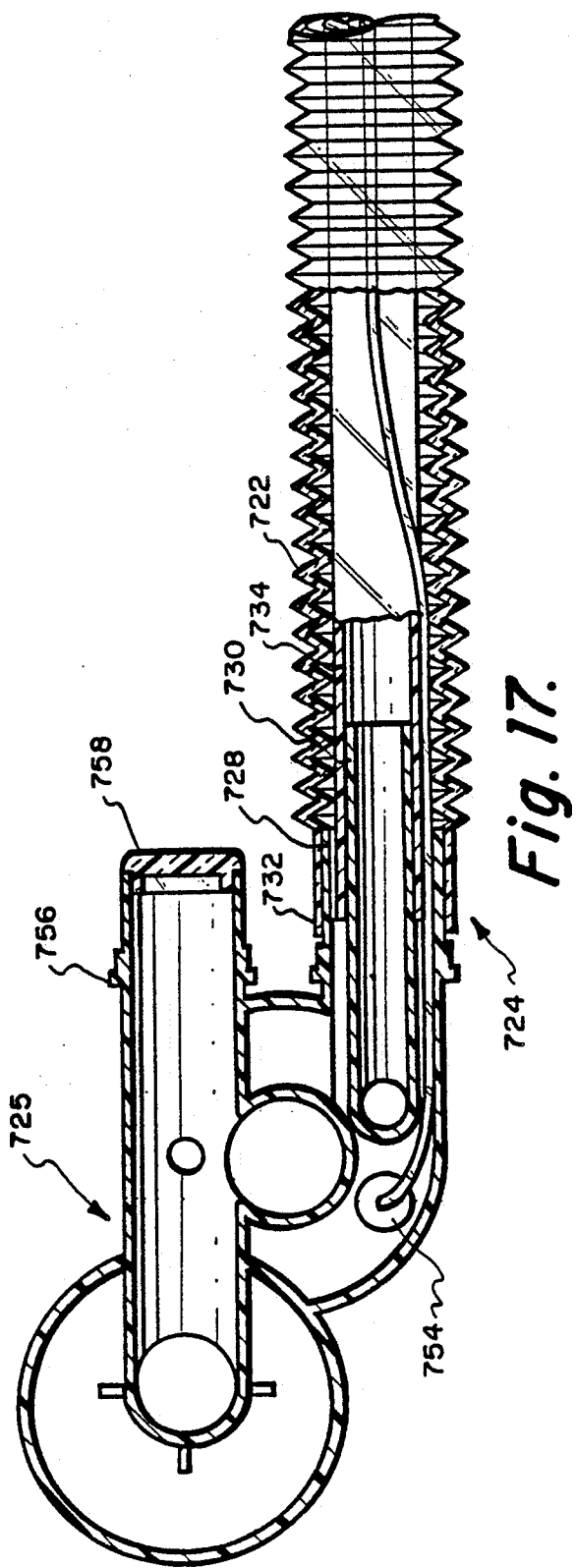
FIG. 17 is a sectional view taken substantially along the plane 17—17 of FIG. 15.

It will be recalled that systems in accordance with the present invention do not require the use of 3-tube patient circuits as shown in FIGS. 8-14 but are readily compatible with 2-tube patient circuits (common inspiratory and expiratory tube) as was previously indicated in connection with FIGS. 2 and 3. FIGS. 15-17 depict a compatible 2-tube structure whose connector body is identical to that shown in FIGS. 8-14 and which differs therefrom in that the connector body nipple 616 is capped and the single breathing tube does not include either an inspiratory or expiratory check valve. The overflow tube and end expiratory monitoring tube are threaded through the single breathing tube as depicted.

Attention is now directed to FIGS. 15-17 which illustrate a preferred implementation of a single use 2-tube patient circuit 720. The 2-tube implementation is very similar in construction to the 3-tube implementation 600 depicted in FIG. 8 except that in lieu of using separate breathing tubes 602, 604 respectively having inspiratory and expiratory valves 618 and 620, the 2-tube implementation 720 includes a single breathing tube 722 which includes no valves. The tube 722 extends between fitting 724 on the connector body 726 and an adaptor 728 (in lieu of the Y-piece shown in FIG. 8) coupled to elbow 730. The fitting 724 of the connector body 726 is identical to that previously described in conjunction with FIG. 10 and includes concentric nipples 728 and 730. The proximal end 732 of the corrugated breathing tube 722 is secured, preferably bonded, to the nipple 728. An inner overflow tube 734 is similarly preferably bonded to the nipple 730.

The distal end 740 of the breathing tube 722 is preferably bonded to an outer nipple 742 formed on adaptor 726. The distal end of overflow tube 730 is preferably bonded to the inner nipple 744 or adaptor 726. The inner and outer nipples 742 and 744 are connected by an open web 746. The distal end of the adaptor 726 defines a tubular portion 750 for receiving the mask elbow 727. With the construction depicted, it should be understood that a substantially free unencumbered communication exists between each of the breathing tube 722, overflow tube 744, and mask elbow 727, via the adaptor 726.

Note also in FIGS. 16 and 17 that an end expiratory monitoring tube 752 is threaded through the mask elbow 727 and then through the web portion 746 of adaptor 726, and through the breathing tube 722 to the nipple 754 in the connector body 725.

The preferred 2-tube implementation of FIGS. 15-17 further differs from the 3-tube implementation of FIGS. 8-14 in that the fitting 756, used for the inspiratory tube in the 3-tube system, is here closed by a cap 758, preferably bonded in place. Additionally, whereas the connector body cap 760 was removable in the 3-tube implementation to accommodate a $CO_2$ canister, it is preferably bonded in place in the 2-tube implementation of FIGS. 15-17 to prevent the inadvertent inclusion of $CO_2$ absorbent material.

From the foregoing, it should now be appreciated that an improved anesthesia rebreathing system has been disclosed herein, characterized by features which considerably enhance safety, reliability, end efficiency as contrasted with prior art systems.

We claim:

1. An anesthesia system for coupling a fresh gas supply means to a patient's airway, said system including:
   a single use structural portion including connector body means defining a fresh gas interface port and a patient overflow interface port;
   a reusable structural portion including mounting structure means defining a fresh gas interface port and a patient overflow interface port;
   means for detachably connecting said connector body means and said mounting structure means for communicating said fresh gas interface ports to one another and said patient overflow interface ports to one another;
   said single use portion including:
   patient airway communication means;
   elongated breathing tube means having a first port coupled to said patient airway communication means and a second port coupled to said single use portion fresh gas interface port;
   overflow means having a first end coupled to said breathing tube means and a second end coupled to said single use portion patient overflow interface port; and
   patient breathing reservoir means having an entrance opening coupled to said breathing tube means proximate to the second port thereof; said reusable portion including:
   patient valve means having an inlet port coupled to said reusable portion patient overflow interface port; and
   control means for establishing the level of pressure at said inlet port for opening said patient valve means;
   said control means including:
   container means;
   means in communication with said container means for varying the pressure therein;
   means mounting said patient breathing reservoir means in said container means whereby pressure variations therein will produce corresponding variations in said reservoir means;
   said means for detachably connecting said connector body means and said mounting structure means including latching means for automatically latching said connector body means to said mounting structure means when said connector body means is seated on said mounting structure means to functionally mate said fresh gas interface ports to one another and said patient overflow ports to one another;
   selectively actuatable unlatching means, said unlatching means being the sole means for unlatching said latching means; and
   sensing means for indicating when said connector body means is seated on said mounting structure means.

2. The system of claim 1 wherein said means for varying the pressure in said container means includes flexible bag means and/or mechanical ventilator means.

3. The system of claim 1 wherein said single use portion further includes $CO_2$ absorber means for removing carbon dioxide from gas flow to said patient airway communication means.

4. An anesthesia system for coupling a fresh gas supply means to a patient's airway, said system including:
   a single use structural portion including connector body means defining a fresh gas interface port and a patient overflow interface port;
   a reusable structural portion including mounting structure means defining a fresh gas interface port and a patient overflow interface port;
   means for detachably connecting said connector body means and said mounting structure means for communicating said fresh gas interface ports to one another and said patient overflow interface ports to one another;
   said single use portion including:
   patient airway communication means;
   elongated breathing tube means having a first port coupled to said patient airway communication means and a second port coupled to said single use portion fresh gas interface port;
   overflow means communicating said patient airway communication means to said single use portion patient overflow interface port; and
   patient breathing reservoir means having an entrance opening coupled to said breathing tube means proximate to the second port thereof; said reusable portion including:
   patient valve means having an inlet port coupled to said reusable portion patient overflow interface port; and
   control means for establishing the level of pressure at said inlet port for opening said patient valve means;
   said control means including:
   container means;
   means in communication with said container means for varying the pressure therein;
   means mounting said patient breathing reservoir means in said container means whereby pressure variations therein will produce corresponding variations in said reservoir means;
said means for detachably connecting said connector body means and said mounting structure means including latching means for automatically latching said connector body means to said mounting structure means when said connector body means is seated on said mounting structure means to functionally mate said fresh gas interface ports to one another and said patient overflow ports to one another;
selectively actuatable unlatching means, said unlatching means being the sole means for unlatching said latching means;
said selectively actuatable unlatching means including means for ejecting said connector body means from said mounting structure means.

5. An anesthesia system for coupling a fresh gas supply means to a patient's airway, said system including:
a single use structural portion including connector body means defining a fresh gas interface port and a patient overflow interface port;
a reusable structural portion including mounting structure means defining a fresh gas interface port and a patient overflow interface port;
means for detachably connecting said connector body means and said mounting structure means for communicating said fresh gas interface ports to one another and said patient overflow interface ports to one another; said single use portion including:
patient airway communication means;
elongated breathing tube means having a first port coupled to said patient airway communication means and a second port coupled to said single use portion fresh gas interface port;
overflow means having a first end coupled to said breathing tube means and a second end coupled to said single use portion patient overflow interface port; and
patient breathing reservoir means having an entrance opening coupled to said breathing tube means proximate to the second port thereof; said reusable portion including:
patient valve means having an inlet port coupled to said reusable portion patient overflow interface port; and
control means for establishing the level of pressure at said inlet port for opening said patient valve means; said control means including:
container means;
means in communication with said container means for varying the pressure therein;
means mounting said patient breathing reservoir means in said container means whereby pressure variations therein will produce corresponding variations in said reservoir means; and wherein
said means for detachably connecting said connector body means and said mounting structure means includes mating means on said connector body means dimensioned to be seated on said mounting structure for mating operatively (1) said fresh gas interface ports to one anotehr to permit gas flow therebetween and (2) patient overflow ports to one another to permit gas flow therebetween;
means for sensing whether said connector body means is seated on said mounting structure; and
means for permitting gas flow out of said mounting structure means fresh gas interface port only when said connector body means is seated.

6. The system of claim 5 wherein said means for detachably connecting further includes latching means for latching said connector body means to said mounting structure means when they are seated together.

7. The system of claim 6 further including manually actuatable means for unlatching said latching means.

8. The system of claim 5 wherein said single use portion further includes $CO_2$ absorber means for removing carbon dioxide from gas flow to said patient airway communication means.

9. An anesthesia system for coupling a fresh gas supply means to a patient's airway, said system including:
patient breathing means defining a fresh gas inlet port;
fresh gas control means defining a fresh gas outlet port;
mating means for detachably mating said patient breathing means and said fresh gas control means with said inlet and outlet ports in communication; and
means for permitting gas flow from said outlet port only when said patient breathing means and said fresh gas control means are mated together;
said means for permitting gas flow including sensor means for sensing when said patient breathing means and said fresh gas control means are mated together; and
means including valve means responsive to said sensor means.

10. The system of claim 9 wherein said mating means includes means for latching said patient breathing means and said fresh gas control means to one another.

11. The system of claim 10 wherein said patient breathing means and said fresh gas control means are respectively configured for relative movement in a first direction; and wherein
said latching means includes a latch member mounted for reciprocal movement in a second direction, substantially perpendicular to said first direction, in response to relative movement between said patient breathing means and said fresh gas control means.

12. The system of claim 11 further including selectively actuatable release means for moving said latch member so as to unlatch said patient breathing means and said fresh gas control means.

13. The system of claim 12 further including selectively actuatable eject means for urging apart said patient breathing means and said fresh gas control means.

14. The system of claim 9 wherein said patient breathing means includes:
connector body means defining said fresh gas inlet port, a breathing tube port, and passageway means for communicating said fresh gas inlet port and said breathing tube port; and
breathing tube means connected to said connector body for communicating with said breathing tube port.

15. The system of claim 14 wherein said fresh gas control means includes mounting means for accommodating said connector body means in a seated position with said inlet and outlet ports in communication; and wherein said mating means includes:
a latch receptacle formed in said connector body; and a latch member supported on said mounting means for extending into said latch receptacle when said connector body means is seated in said mounting means.

16. The system of claim 15 wherein said latch member is mounted for reciprocal movement toward and away from said latch receptacle;
   means responsive to said connector body means moving toward said seated position for moving said latch member away from said latch receptacle; and
   means urging said latch member into said latch receptacle when said connector body means is in said seated position.

17. The system of claim 16 including selectively actuatable pneumatic means for moving said latch member out of said latch receptacle.

18. The system of claim 17 further including eject means responsive to said pneumatic means for forcing said connector body means out of said seated position.

19. The anesthesia system of claim 9 wherein said fresh gas control means further includes:
   control member means mounted for movement between an off position for preventing gas flow from said outlet port to said inlet port, and a ventilating position for allowing gas flow from said outlet port to said inlet port; and
   means responsive to said sensor means for permitting movement of said control member means from said off to said ventilating position only when said patient breathing means and said fresh gas control means are mated together.

20. The system of claim 19 wherein said control member means includes a control member mounted for rotational movement between said off and ventilating positions; and wherein
   said means responsive to said signal includes locking means for normally locking said control member against said rotational movement, said locking means being responsive to said signal for releasing said control member.

21. An anesthesia system for coupling a fresh gas supply means to a patient's airway, said system including:
   patient breathing means defining a fresh gas inlet port;
   fresh gas control means defining a fresh gas outlet port;
   mating means for detachably mating said patient breathing means and said fresh gas control means with said inlet and outlet ports in communication;
   said mating means comprising latching means for latching said patient breathing means and said fresh gas control means to one another in response to relative movement therebetween;
   selectively actuatable unlatching means, said unlatching means being the sole means for unlatching said latching means;
   sensor means for sensing whether said patient breathing means and said fresh gas control means are mated together; and
   means including valve means responsive to said sensor means for coupling said fresh gas supply means to said fresh gas outlet port only when said patient breathing means and said fresh gas control means are mated together.

22. The system of claim 21 wherein said patient breathing means and said fresh gas control means are respectively configured for relative movement in a first direction; and wherein
   said latching means includes a latch member mounted for reciprocal movement in a second direction, substantially perpendicular to said first direction, in response to relative movement between said patient breathing means and said fresh gas control means.

23. The system of claim 21 wherein said patient breathing means includes:
   connector body means defining said fresh gas inlet port, a breathing tube port, and passageway means for communicating said fresh gas inlet and said breathing tube ports; and
   breathing tube means connected to said connector body for communicating with said breathing tube port.

24. The system of claim 23 wherein said fresh gas control means includes mounting means for accommodating said connector body means in a seated position with said inlet and outlet ports in communication; and wherein said latching means includes:
   a latch receptacle formed in said connector body; and
   a latch member supported on said mounting means for extending into said latch receptacle when said connector body means is seated in said mounting means.

25. An anesthesia system for coupling a fresh gas supply means to a patient's airway, said system including:
   breathing tube means including a patient airway communication means and a connector body means defining a fresh gas inlet port and a monitoring outlet port;
   mounting means defining a fresh gas outlet port and a monitoring inlet port;
   said connector body means being configured to mate with said mounting means to concurrently establish communication between said fresh gas inlet and fresh gas outlet ports and said monitoring outlet and monitoring inlet ports
   mating latching means carried by said mounting means and said connector body means for engaging in response to said connector body means being mated to said mounting means; and
   monitoring tube means extending through said breathing tube means for coupling said monitoring outlet port to said patient airway communication means.

26. The system of claim 25 wherein said connector body means further defines an overflow outlet port; and wherein
   said mounting means further defines an overflow inlet port positioned so as to communicate with said overflow outlet port when said connector body means is seated.

27. The system of claim 25 further including means for permitting gas flow from said fresh gas outlet port to said fresh gas inlet port only when said connector body means is seated.

28. An anesthesia system for coupling a fresh gas supply means to a patient's airway, said system including:
   patient breathing means defining a fresh gas inlet port;
   fresh gas control means defining a fresh gas outlet port;

mating means for detachably mating said patient breathing means and said fresh gas control means with said inlet and outlet ports in communication;

control member means mounted for movement between an off position for preventing gas flow from said outlet port to said inlet port and a ventilating position for allowing gas flow from said outlet port to said inlet port;

locking means for normally locking said control member means against movement from said off position to said ventilating position; and sensor means responsive to said patient breathing means and said fresh gas control means being mated together for disabling said locking means to permit movement of said control member means to said ventilating position.

29. An anesthesia system for coupling a fresh gas supply means to a patient's airway, said system including:

patient breathing means defining a fresh gas inlet port;

fresh gas control means defining a fresh gas outlet port;

mating means for detachably mating said patient breathing means and said fresh gas control means with said inlet and outlet ports in communication;

control member means mounted for movement between an off position for preventing gas flow from said outlet port to said inlet port and a ventilating position for allowing gas flow from said outlet port to said inlet port; and sensor means for permitting gas flow from said outlet port to said inlet port only when said patient breathing means and said fresh gas control means are mated together;

including means for latching said patient breathing means and said fresh gas control means to one another; and unlatching means selectively operable only when said control member means defines said off position for unlatching said patient breathing means and said fresh gas control means.

30. Patient circuit means suitable for use with an anesthesia control apparatus having a fresh gas outlet port, and a latch member and inclined surface member each mounted for linear reciprocal movement, said patient circuit means comprising:

patient airway communication means;

a connector body defining a fresh gas inlet port, a breathing tube port, and passageway means communicating said fresh gas inlet and said breathing tube ports;

breathing tube means connecting said breathing tube port to said patient airway communication means;

said connector body including latching means for latching said connector body to said anesthesia control apparatus with said fresh gas inlet port aligned with said fresh gas outlet port, said latching means including a depending member defining a receptacle for accommodating said latch member mounted on said anesthesia control apparatus;

said depending member further defining a terminal surface for engaging said latch member to move it linearly in a first direction when said connector body is moved in a second direction perpendicular to said first direction;

said depending member further defining a ramp surface engagable by said linearly moveable inclined surface on said anesthesia control apparatus for ejecting said connector body from said control apparatus.

31. The circuit means of claim 30 wherein said connector body further includes a patient reservoir port and passageway means communicating said fresh gas inlet to said patient reservoir port; and a flexible patient breathing reservoir communicating with said patient reservoir port.

32. The circuit means of claim 30 further including $CO_2$ absorber means coupled to said connector body for removing carbon dioxide from gas flow to said patient airway communication means.

33. Patient circuit means for use with an anesthesia control apparatus having a fresh gas outlet port, said circuit means comprising:

patient airway communication means;

patient breathing reservoir means adapted to communicate with said fresh gas outlet port;

elongated breathing tube means having an open first end coupled to said patient airway communication means, an open second end coupled to said patient breathing reservoir means, and an overflow port located proximate to said first end;

elongated overflow tube means having an open first end coupled to said overflow port and an open second end adapted to communicate with an overflow valve means;

one way expiratory valve means in said breathing tube means located between said overflow port and said second end for permitting gas flow only in a direction from said overflow port to said second end;

inspiratory tube means having an open first end coupled to said patient breathing reservoir means and an open second end coupled to said breathing tube means between the first end thereof and said expiratory valve means;

said inspiratory tube means including one way inspiratory valve means for permitting gas flow only in a direction from said first to said second end of said inspiratory tube means.

34. The circuit means of claim 33 further including a connector body including a fresh gas inlet port adapted to be coupled to said fresh gas outlet port, a patient breathing port adapted to be coupled to said patient breathing reservoir means, and fresh gas passageway means communicating said fresh gas inlet and patient breathing ports.

35. The circuit means of claim 34 wherein said connector body includes means depending therefrom for engaging a latch member on said anesthesia control apparatus when said connector body is seated onto said control apparatus; and wherein said depending means includes receptacle means for receiving said latch member.

36. The circuit means of claim 34 further including $CO_2$ absorber means coupled to said connector body for removing carbon dioxide from gas flow to said patient airway communication means.

37. The circuit means of claim 34 wherein said connector body further includes a monitoring interface port; and monitoring means coupling said patient airway communication means to said monitoring interface port.

38. Patient circuit means for use with an anesthesia control apparatus having a mounting means defining a fresh gas port and a monitoring port, said circuit means comprising:

patient airway communication means;

connector body means including a mating portion defining a fresh gas interface port and a monitoring interface port, said mating portion being configured to mate with said mounting means to concurrently establish communication of said fresh gas ports to one another and said monitoring ports to one another;

mating latching means carried by said mounting means and said mating portion for engaging in response to said mating portion means being mated to said mounting means;

said connector body means further including a breathing tube port coupled internally through said connector body means to said fresh gas interface port;

breathing tube means coupling said patient airway communication means to said breathing tube port; and monitoring tube means extending substantially coextensive with said breathing tube means for coupling said patient airway communication means to said monitoring interface port.

39. The circuit means of claim 38 wherein said connector body means mating portion further defines an overflow interface port; and wherein said connector body means further includes an overflow tube port coupled internally through said connector body means to said overflow interface port; and overflow tube means coupling said patient airway communication means to said overflow tube port.

40. The circuit means of claim 38 wherein said connector body means further includes a patient reservoir port and passageway means extending internally through said connector body means for coupling said patient reservoir port to said fresh gas interface port; and a flexible patient breathing reservoir communicating with said patient reservoir port.

41. The circuit means of claim 38 wherein said connector body means includes means depending therefrom for engaging a latch member on said anesthesia control apparatus when said connector body means is seated onto said control apparatus.

42. The circuit means of claim 38 further including $CO_2$ absorber means coupled to said connector body means for removing carbon dioxide from gas flow to said patient airway communication means.

43. An anesthesia system for coupling a fresh gas supply means to a patient's airway, said system comprising:

(1) patient circuit means including:
 (a) patient airway communication means;
 (b) patient reservoir means;
 (c) breathing tube means having a first port coupled to said patient airway communication means, a second port coupled to said patient reservoir means, and a third port coupled to said fresh gas supply means;
 (d) patient valve means including means for communicating inlet and outlet ports in response to pressure at said inlet port exceeding a control pressure;
 (e) overflow passageway means having a first end coupled to said breathing tube means and a second end coupled to said patient valve means inlet port; and (2) control circuit means for producing said control pressure, said control circuit means including:
 (a) container means for accomodating said patient reservoir means; and
 (b) means for varying the pressure in said container means to produce corresponding pressure variations in said patient reservoir means, said pressure varying means comprising:
  (b1) working gas source means for supplying gas to said container means;
  (b2) manual means including outside bag means communicating with said container means, adapted to be squeezed by a user, for producing pressure changes in said container means;
  (b3) non-manual means for producing pressure changes;
  (b4) user operable selector means for selectively coupling either said manual means or said non-manual means to said container;
  (b5) overflow means for venting excess working gas from said outside bag and container means, said overflow means including user operable variable means for variably controlling gas flow through said overflow means;
  (b6) said user operable selector means and said user operable variable flow means includes a common manually operable control member.

44. The system of claim 43 wherein said control circuit means further includes:

bias means having inlet and outlet ports;

means communicating said bias means inlet port with the pressure in said container means;

said bias means including means responsive to the pressure in said container means exceeding a predetermined bias for venting gas through said bias means outlet port.

45. The system of claim 43 wherein said patient valve means outlet port is coupled to said manual means for supplying working gas thereto.

46. The system of claim 43 further including:

a high pressure gas source; and user operable means for selectively coupling said high pressure gas source to said manual means for supplying working gas thereto.

47. The system of claim 43 further including:

a high pressure gas source;

fill means actuatable for supplying gas from said high pressure gas source to said container means;

dump means actuatable for venting gas from said container means; and user operable control means for concurrently actuating said fill means and said dump means.

48. The system of claim 47 wherein said dump means includes bias means for venting gas from said container means when the gas pressure therein exceeds a bias defined by said bias means.

49. The system of claim 48 wherein said user operable control means includes means for maintaining said dump means actuated slightly later than said concurrent actuation of said fill means and said dump means whereby gas pressure in said container means will be established by said bias means.

50. The system of claim 48 wherein said user operable control means includes means for actuating said dump means slightly earlier than said concurrent actuation of said fill means and said dump means for venting excess gas from said container means.

51. The system of claim 47 wherein said user operable control means includes a single control member manually operable to actuate both said fill means and said dump means.

52. The system of claim 51 wherein said single control member is mounted for movement between a rest position and an actuated position for actuating said fill means and said dump means.

53. The system of claim 52 wherein said user operable variable flow means includes said single control member; and
 means responsive to rotation of said single control member for variably opening said overflow means.

54. The system of claim 43 further including:
 nonmanual means for producing pressure changes in said container means; and
 user operable selector means for selectively coupling either said manual means or said nonmanual means to said container means.

55. The system of claim 54 further including:
 a high pressure gas source; and
 user operable means for selectively coupling said high pressure gas source to said manual means or said nonmanual means for supplying working gas thereto.

56. The system of claim 54 wherein said user operable selector means and said user operable variable flow means includes a common manually operable control member;
 means mounting said control member for movement between a manual position for coupling said manual means to said container and nonmanual position for coupling said nonmanual means to said container means.

57. The system of claim 54 further including:
 a high pressure gas source;
 fill means actuatable for supplying gas from said high pressure gas source to said container means;
 dump means actuatable for venting gas from said container means; and
 means for concurrently actuating said fill means and said dump means.

58. The system of claim 54 wherein said user operable selector means and said user operable variable flow means includes a common manually operable control member;
 means mounting said control member for movement between a manual position for coupling said manual means to said container means and a nonmanual position for coupling said nonmanual means to said container means.

59. The system of claim 58 further including:
 a high pressure gas source;
 fill means actuatable for supplying gas from said high pressure gas source to said container means;
 dump means actuatable for venting gas from said container means; and
 means responsive to said control member moving into said manual or nonmanual positions for concurrently actuating said fill means and said dump means.

60. An anesthesia system for coupling a fresh gas supply means to a patient's airway, said system comprising:
 (1) patient circuit means including:
  (a) patient airway communication means;
  (b) patient reservoir means;
  (c) breathing tube means having a first end, said first and having a first port coupled to said patient airway communication means, a second port coupled to said patient reservoir means, a second end having a port coupled to said fresh gas supply means, and an overflow port located proximate to said first end;
  (d) patient valve means including means for communicating inlet and outlet ports in response to pressure at said inlet port exceeding a control pressure;
  (e) overflow passageway means having a first end coupled to said breathing tube means and a second end coupled to said patient valve means inlet port;
  (f) one way expiratory valve means in said breathing tube means located between the overflow port and second end thereof for permitting gas flow therein only in a direction from said breathing tube means overflow port to the second end thereof; and
 (2) control circuit means for producing said control pressure, said control circuit means including:
  (a) container means for accommodating said patient reservoir means;
  (b) outside bag means coupled to said container means and adapted to be squeezed by a user therein to produce corresponding pressure variations in said patient reservoir means;
  (c) control means for selectively defining either a first automatic bag mode or a second manual bag mode;
  (d) working gas source means;
  (e) means opeable during said manual bag mode for supplying working gas from said working gas source means to said outside bag means and container means; and
  (f) user opeable variable overflow means operable during said manual bag mode for variably venting excess working gas from said outside bag means and container means.

61. The system of claim 60 further including:
 fill means actuatable for supplying gas from said working gas source means to said container means;
 dump means actuatable for venting gas from said container means; and wherein
 said control means includes means for concurrently actuating said fill means and said dump means.

62. The system of claim 60 further including
 fill means actuatable for supplying gas from said working gas source means to said container means;
 dump means actuatable for venting gas from said container means; and
 means responsive to said control means switching from one mode to the other mode for concurrently actuating said fill means and said dump means.

63. An anesthesia system for coupling a fresh gas supply means to a patient's airway, said system comprising:
 (1) patient circuit means including:
  (a) patient airway communication means;
  (b) patient reservoir means;
  (c) breathing tube means having a first port coupled to said patient airway communication means, a second port coupled to said patient reservoir means, and a third port coupled to said fresh gas supply means;

(d) patient valve means including means for communicating inlet and outlet ports in response to pressure at said inlet port exceeding a control pressure;

(e) overflow passageway means having a first end coupled to said breathing tube means and a second end coupled to said patient valve means inlet port; and (2) control circuit means for producing said control pressure, said control circuit means including:

(a) container means for accommodating said patient reservoir means; and (b) means for varying the pressure in said container means to produce corresponding pressure variations in said patient reservoir means, said pressure varying means comprising:

(b1) manual means, including outside bag means adapted to be squeezed by a user, for producing pressure changes;

(b2) nonmanual means for producing pressure changes;

(b3) user operable selector means for selectively coupling either said manual means or said nonmanual means to said container means;

(b4) bias means having inlet and outlet ports;

(b5) means communicating said bias means inlet port with the pressure in said container means and wherein (b6) said bias means allows gas flow out of said container means only when the pressure therein exceeds a predetermined bias said predetermined bias creating a positive end expiratory pressure on said patent reservoir means.

64. The system of claim 63 further including:
a high pressure gas source;
fill means actuatable for supplying gas from said high pressure gas source to said container means;
dump means actuatable for venting gas from said container means; and
user operable control means for concurrently actuating said fill means and said dump means.

65. The system of claim 64 wherein said dump means includes second bias means for venting gas from said container means when the gas pressure therein exceeds a bias defined by said second bias means.

66. An anesthesia system for coupling a fresh gas supply means to a patient's airway, said system comprising:

(1) patient circuit means including:
   (a) patient airway communication means;
   (b) patient reservoir means;
   (c) breathing tube means having a first port coupled to said patient airway communication means, a second port coupled to said patient reservoir means, and a third port coupled to said fresh gas supply means;
   (d) patient valve means including means for communicating inlet and outlet ports in response to pressure at said inlet port exceeding a control pressure;
   (e) overflow passageway means having a first end coupled to said breathing tube means and a second end coupled to said patient valve means inlet port;

(2) a high pressure gas source; and (3) control circuit means for producing said control pressure, said control circuit means including:

(a) container means for accommodating said patient reservoir means;

(b) outside bag means coupled to said container means and adapted to be squeezed by a user to produce pressure variations in said patient reservoir means;

(c) fill means actuatable for supplying gas from said high pressure gas source to said container means;

(d) dump means actuatable for venting gas from said container means; and (e) user operable control means for concurrently actuating said fill means and said dump means, said user operable control means comprising a single selectively operable control member.

67. The system of claim 66 wherein said fill means additionally supplies gas from said high pressure gas source to said patient circuit means.

68. The system of claim 66 wherein said dump means includes bias means for venting gas from said container means when the gas pressure therein exceeds a bias defined by said bias means.

69. The system of claim 66 wherein said user operable control means includes means for maintaining said dump means actuated slightly later than said concurrent actuation of said fill means and said dump means whereby gas pressure in said container means will be established by said biased check valve means.

70. The system of claim 66 wherein said user operable control means includes means for actuating said dump means slightly earlier than said concurrent actuation of said fill means and said dump means for venting excess gas from said container means.

71. An anesthesia system for coupling a fresh gas supply means to a patient's airway, said system comprising:

(1) patient circuit means including:
   (a) patient airway communication means;
   (b) patient reservoir means;
   (c) breathing tube means having a first port coupled to said patient airway communication means, a second port coupled to said fresh gas supply means;
   (d) patient valve means including means for communicating inlet and outlet ports in response to pressure at said inlet port exceeding a control pressure;
   (e) overflow passageway means having a first end coupled to said breathing tube means and a second end coupled to said patient valve means inlet port;

(2) a high pressure gas source; and (3) control circuit means for producing said control pressure, said control circuit means including:

(a) container means coupled to said patient valve means outlet port for accommodating said patient reservoir means;

(b) outside bag means coupled to said container means and adapted to be squeezed by a user to produce pressure variations in said patient reservoir means;

(c) fill means actuatable for supplying gas from said high pressure gas source to said patient circuit means;

(d) dump means actuatable for venting gas from said container means; and (e) user operable control means for concurrently actuating said fill means and said dump means, said user operable control means comprising a single selectively operable control member.

72. The system of claim 71 wherein said dump means includes bias means for venting gas from said container means when the gas pressure therein exceeds a bias defined by said bias means.

73. In an anesthesia system including:
(1) patient circuit means comprising:
(a) patient airway communication means;
(b) patient reservoir means;
(c) breathing tube means having a first port coupled to said patient airway communication means and a second port coupled to said patient reservoir means;
(d) patient valve means including means for communicating inlet and outlet ports in response to pressure at said inlet port exceeding a control pressure;
(e) overflow passageway means having a first end coupled to said breathing tube means and a second end coupled to said patient valve means inlet port;
(2) a gas source; and
(3) control circuit means for producing said control pressure, said control circuit means including:
(a) container means for accommodating said patient reservoir means; and
(b) outside bag means adapted to be squeezed by a user coupled to said container means for producing pressure variations in said patient reservoir means, the improvement comprising:
fill means actuatable for supplying gas from said gas source to said container means;
dump means actuatable for venting gas from said container means;
a unitary control member mounted for movement between a rest position and an actuated position; and
means responsive to said control member moving to said actuated position for actuating both said fill means and said dump means.

74. The improvement of claim 73 further including flush means actuatable in response to said control member moving to said actuated position for supplying gas from said gas source to said patient circuit means.

75. The combination of claim 73 further including:
overflow valve means for venting excess gas from said outside bag means; and wherein
said control member is mounted for rotational movement; and
means responsive to said control member rotational movement for variably opening said overflow valve means.

76. In an anesthesia system including:
(1) patient circuit means comprising:
(a) patient airway communication means;
(b) patient reservoir means;
(c) breathing tube means having a first port coupled to said patient airway communication means and a second port coupled to said patient reservoir means;
(d) patient valve means including means for communicating inlet and outlet ports in response to pressure at said inlet port exceeding a control pressure;
(e) overflow passageway means having a first end coupled to said breathing tube means and a second end coupled to said patient valve means inlet port;
(2) a gas source; and
(3) control circuit means for producing said control pressure, said control circuit means including:
(a) container means for accommodating said patient reservoir means;
(b) manual means adapted to be squeezed by a user for producing pressure variations; and
(c) nonmanual means for producing pressure variations; the improvement comprising:
a single control member mounted for rotational movement between a first manual position and a second nonmanual position;
means responsive to said control member defining said manual position for coupling said manual means to said container means for producing pressure variations therein;
variable overflow means coupled to said manual means for variably venting gas therefrom;
said control member being capable of limited rotational movement when in said manual position for varying said overflow means; and
means responsive to said control member defining said nonmanual position for coupling said nonmanual means to said container means for producing pressure variations therein.

77. The system of claim 76 further including:
fill means actuatable for supplying gas from said gas source to said container means;
dump means actuatable for venting gas from said container means; and wherein
said single control member is also capable of movement between a rest position and an actuated position; and
means responsive to said control member defining said actuated position for actuating said fill means and said dump means.

78. The system of claim 77 further including:
means for compelling said control member to move into said actuated position in order to switch between said manual and nonmanual positions.

79. Patient circuit means for use in an anesthesia system for delivering fresh anesthesia gas to a patient's airway, said patient circuit means including:
elongated breathing tube means having a first end adapted to communicate with the patient's airway and a second end adapted to communicate with a source of fresh anesthesia gas, said breathing tube means further including an overflow port located proximate to said first end;
elongated overflow tube means, substantially coextensive with said breathing tube means, having open first and second ends, said first end being coupled to said overflow port;
patient overflow valve means coupled to said overflow tube means second end for permitting gas flow in said overflow tube means only in a direction from the first to the second end thereof;
means mounting said overflow valve means in close proximity to said elongated breathing tube means second end;
one way expiratory valve means in said breathing tube means located between the overflow port and second end thereof for permitting gas flow therein only in a direction from said breathing tube means overflow port to the second end thereof;

inspiratory tube means having an open first end coupled to said breathing tube means between said overflow port and second end thereof and an open second end coupled to said breathing tube means proximate to the first end thereof;

said inspiratory tube means including one way inspiratory valve means for permitting gas flow only in a direction from said first to said second end of said inspiratory tube means.

80. The circuit means of claim 79 further including $CO_2$ absorber means for reducing the carbon dioxide content of gas flowing from said inspiratory tube means second end.

81. A method of operating an anesthesia delivery system comprised of a patient circuit portion and a control circuit portion including the concurrent steps of:
supplying high pressure gas to flush said patient circuit portion and fill said control circuit portion; and
venting said control circuit portion through a bias means for establishing a predetermined gas volume and pressure therein.

82. The method of claim 81 including the further step of manually actuating a single control member to cause said selective supplying of high pressure gas to both said patient circuit portion and said control circuit portion.

83. The method of claim 82 wherein said step of actuating said control member also causes said venting of said control circuit portion.

84. The method of claim 83 including the further step of initiating said venting earlier than said supplying of high pressure gas.

85. The method of claim 83 including the further step of terminating said venting after the termination of said supplying of high pressure gas.

86. The method of claim 82 wherein said step of actuating said single control member includes the step of manually depressing said control member to move it substantially linearly along a longitudinal axis.

87. The method of claim 86 including the further step of selectively rotating said control member to variably vent said control circuit portion.

88. A method of operating an anesthesia delivery system including a patient circuit portion comprising the steps of:
selectively supplying high pressure gas to said patient circuit portion while concurrently venting said patient circuit portion through a bias means for establishing a predetermined gas volume and pressure in said patient circuit portion; and
initiating said venting earlier than said supplying of high pressure gas 89. The method of claim 88 including a further step of manually actuating a single control member to cause said selective supplying of high pressure gas and venting of said patient circuit portion.

90. The method of claim 89 wherein said step of actuating said single control member includes the step of manually depressing said control member to move it substantially linearly along a longitudinal axis.

91. The method of claim 90 including a further step of selectively rotating said control member to variably vent said patient circuit portion.

92. The method of claim 89 including the further step of terminating said venting after the termination of said supplying of high pressure gas.

93. An anesthesia system for coupling a fresh gas supply means to a patient's airway, said system comprising:
(1) patient circuit means including:
  (a) patient airway communication means;
  (b) breathing tube means having a first port coupled to said patient airway communication means, a second port coupled to said fresh gas supply means;
  (c) patient valve means including means for communicating inlet and outlet ports in response to pressure at said inlet port exceeding a reference pressure;
  (d) overflow passageway means having a first end coupled to said breathing tube means and a second end coupled to said patient valve means inlet port;
(2) a high pressure gas source;
(3) fill means actuatable for supplying gas from said high pressure gas source to said patient circuit means;
(4) dump means actuatable for venting gas from said patient circuit means; and
(5) user operable control means for concurrently actuating said fill means and said dump means, said user operable control means comprising a single selectively operable control member.

94. The system of claim 93 wherein said dump means includes bias means for venting gas from said patient circuit means when the gas pressure therein exceeds a bias defined by said bias means.

95. The system of claim 93 wherein said user operable control means includes means for maintaining said dump means actuated slightly later than said concurrent actuation of said fill means and said dump means whereby gas pressure in said patient circuit means will be established by said biased means.

96. The system of claim 93 wherein said user operable control means includes means for actuating said dump means slightly earlier than said concurrent actuation of said fill means and said dump means for venting excess gas from said patient circuit means.

97. The system of claim 93 wherein said patient circuit means further includes patient breathing reservoir means for defining a variable gas storage volume.

98. The system of claim 93 wherein said patient circuit means further includes $CO_2$ absorber means for reducing the carbon dioxide content of gas flowing to said patient airway communication means.

99. An anesthesia system for coupling a fresh gas supply means to a patient's airway, said system including:
a single use structural portion including connector body means defining a fresh gas interface port and a patient overflow interface port;
a reusable structural portion including mounting structure means defining a fresh gas interface port and a patient overflow interface port;
means for detachably connecting said connector body means and said mounting structure means for communicating said fresh gas interface ports to one another and said patient overflow interface ports to one another;
said single use portion including:
patient airway communication means;
elongated breathing tube means having a first port coupled to said patient airway communication means and a second port coupled to said single use portion fresh gas interface port;

overflow means communicating said patient airway communication means to said single use portion patient overflow interface port; and patient breathing reservoir means having an entrance opening coupled to said breathing tube means proximate to the second port thereof; said reusable portion including:

patient valve means having an inlet port coupled to said reusable portion patient overflow interface port for venting gas from said single use portion; and control means for controlling the opening of said patient valve means;

said control means including:

container means;

means in communication with said container means for varying the pressure therein;

means mounting said patient breathing reservoir means in said container means whereby pressure variations therein will produce corresponding variations in said reservoir means; and expiratory pressure regulator means for venting gas from said patient valve means only when the pressure in said single use portion exceeds a first positive threshold level and for passing gas displaced from said container means only when the pressure therein exceeds said first positive threshold level to thus establish a positive end expiratory pressure against which a patient can breathe.

100. The system of claim 99 further including spirometer means isolated from gas supplied to said patient airway communication means for measuring the gas flow into and/or out of said container means.

101. In an anesthesia system including a patient circuit for coupling a fresh gas supply to a patient's airway wherein said patient circuit includes valve means for venting gas from the patient circuit and a variable volume reservoir means for alternately (1) receiving gas during patient exhalation and (2) supplying stored gas during patient inhalation, the improvement comprising:

a constant volume container means for accommodating said variable volume reservoir means;

exit path means for passing gas displaced from said container means; and bias means for establishing a positive end expiratory pressure against which a patient breathes, said bias means defining a positive threshold pressure only above which said valve means vents gas from said patient circuit and said exit path means passes gas from said container means.

102. The system of claim 101 further including spirometer means isolated from gas inhaled by said patient for measuring the gas flow into and/or out of said container means.

* * * * *